(12) United States Patent
Ryu et al.

(10) Patent No.: US 12,383,605 B2
(45) Date of Patent: Aug. 12, 2025

(54) EXENATIDE ANALOG AND USE THEREOF

(71) Applicant: ANYGEN CO., LTD., Gwangju (KR)

(72) Inventors: Jae Ha Ryu, Gwangju (KR); Sang Hyun Joo, Gwangju (KR); Ye Ga Park, Gwangju (KR)

(73) Assignee: ANYGEN CO., LTD., Gwangju (KR)

(*) Notice: Subject to any disclaimer, the term of this patent is extended or adjusted under 35 U.S.C. 154(b) by 712 days.

(21) Appl. No.: 17/635,039

(22) PCT Filed: Aug. 13, 2020

(86) PCT No.: PCT/KR2020/010751
§ 371 (c)(1),
(2) Date: Feb. 14, 2022

(87) PCT Pub. No.: WO2021/029698
PCT Pub. Date: Feb. 18, 2021

(65) Prior Publication Data
US 2022/0323548 A1    Oct. 13, 2022

(30) Foreign Application Priority Data

Aug. 13, 2019  (KR) .................. 10-2019-0098911
Aug. 12, 2020  (KR) .................. 10-2020-0101087
Aug. 12, 2020  (KR) .................. 10-2020-0101088

(51) Int. Cl.
| | |
|---|---|
| *A61K 38/26* | (2006.01) |
| *A23L 29/281* | (2016.01) |
| *A61P 3/04* | (2006.01) |
| *A61P 3/10* | (2006.01) |
| *C07K 14/605* | (2006.01) |

(52) U.S. Cl.
CPC ............ *A61K 38/26* (2013.01); *A23L 29/281* (2016.08); *A61P 3/04* (2018.01); *A61P 3/10* (2018.01); *C07K 14/605* (2013.01)

(58) Field of Classification Search
CPC ........ A61K 38/26; A61K 38/00; A61K 47/54; A61P 3/10; C07K 14/605
See application file for complete search history.

(56) References Cited

U.S. PATENT DOCUMENTS

| | | |
|---|---|---|
| 9,365,632 B2 | 6/2016 | Haack et al. |
| 2011/0301084 A1 | 12/2011 | Lau et al. |
| 2016/0137712 A1 | 5/2016 | Lu et al. |

FOREIGN PATENT DOCUMENTS

| | | |
|---|---|---|
| EP | 3121195 A1 | 1/2017 |
| KR | 10-2015-0111297 A | 10/2015 |
| WO | WO-2017/189342 A1 | 11/2017 |

OTHER PUBLICATIONS

Taichi Ueda, Identification of glycosylated exendin-4 analogue with prolonged blood glucose-lowering activity through glycosylation scanning substitution , Bioorganic & Medicinal Chemistry Letters 20 (2010) 4631-4634.*
Yingying Pan, A novel GLP-1 analog, a dimer of GLP-1 via covalent linkage by a lysine, prolongs the action of GLP-1 in the treatment of type 2 diabetes, Peptides 88 (2017) 46-54.*
Jing Han,, Preparation and Pharmaceutical Characterizations of Lipidated Dimeric Xenopus Glucagon-Like Peptide-1 Conjugates, Bioconjugate Chem. 2017, 29, 390-402.*
Tae Hyung Kim, Mono-PEGylated Dimeric Exendin-4 as High Receptor Binding and Long-Acting Conjugates for Type 2 Anti-Diabetes Therapeutics , Bioconjugate Chem. 2011, 22, 625-632.*
Office Action of Korean Patent Application No. 10-2020-0101852 issued on Aug. 29, 2022.
Kim, T. H., et al.; "Mono-PEGylated Dimeric Exendin-4 as High Receptor Binding and Long-Acting Conjugates for Type 2 Anti-Diabetes Therapeutics", Bioconjugate Chemistry, 2011, 22, 625-632.
Office Action from corresponding Canadian Patent Application No. 3147770, issued on Aug. 13 2020.
Office Action from corresponding Japanese Patent Application No. 2022-509115, issued on Feb. 7, 2023.
Office Action from corresponding European Patent Application No. 20852849.7 issued on Aug. 23, 2023.
Yi, L., et al., "Expression and Purification of Exendin-4 Dimer in *Escherichia coli* and Its Interaction with GLP-1 Receptor In Vitro", Protein & Peptide Letters, 2006, 13, 823-827.
Lee, J. G., et al. "Replacement of the C-terminal Trp-cage of exendin-4 with a fatty acid improves therapeutic utility", Biochemical Pharmacology, 151, 2018, pp. 59-68.
Li, Y., et al., "Disulfide bond prolongs the half-life of therapeutic peptide-GLP-1", Peptides, 32, 2011, pp. 1400-1407.
Chae, S. Y., et al., "The fatty acid conjugated exendin-4analogs for type 2 antidiabetic therpeutics", Journal of Controlled Release, 144, 2010, pp. 10-16.

(Continued)

*Primary Examiner* — Lianko G Garyu
*Assistant Examiner* — Erinne R Dabkowski
(74) *Attorney, Agent, or Firm* — Harness, Dickey & Pierce, P.L.C.

(57) ABSTRACT

The present invention pertains to an exenatide analogue glycosylated to a specific residue, and a use thereof. The present invention provides a novel substance for treating diabetes, the novel substance exhibiting improved in vivo stability compared to conventional exenatides and analogues thereof. The present invention pertains to an exenatide dimer analogue and a use thereof. The present invention provides a novel substance for treating diabetes and obesity, the novel substance exhibiting significantly improved in vivo stability compared to conventional exenatides and analogues thereof.

3 Claims, 33 Drawing Sheets

Specification includes a Sequence Listing.

(56) References Cited

OTHER PUBLICATIONS

Moradi, S. V., et al.; Glycosylation, an effective synthetic strategy to imrpove the bioavailability of therapeutic peptides. Chem. Sci. 2016, vol. 7, pp. 2492-2500.

Pan, Y., et al.; A novel GLP-1 analog, a dimer of GLP-1 via covalent linkage by a lysine, prolongs the action of GLP-1 in the treatment of type 2 diabetes. Peptides. 2017, vol. 88, pp. 46-54.

Soni, H., Peptide-based GLP-1/glucagon co-agonists: A double-edged sword to combat diabesity. Medical Hypothesis, 2016, vol. 95, pp. 5-9.

Axelsen, L. N., et al.; Glucagon and a glucagon-GLP-1 dual-agonist increases cardiac performance with different metabolic effects in insulin-resistant hearts. British Journal of Pharmacology. 2012. vol. 165, pp. 2736-2748.

International Search Report from corresponding PCT Application No. PCT/KR2020/010751, dated Dec. 7, 2020.

\* cited by examiner

EXENATIDE ANALOG AND USE THEREOF

This application is a national phase application of PCT Application No. PCT/KR2020/010751, filed on Aug. 13, 2020, which claims priority to Korean Patent Application Nos. 10-2019-0098911, filed on Aug. 13, 2019, 10-2020-0101088, filed on Aug. 12, 2020 and 10-2020-0101087, filed on Aug. 12, 2020. The entire disclosures of the applications identified in this paragraph are incorporated herein by reference.

TECHNICAL FIELD

The present disclosure relates to glycosylated exenatide analogs and uses thereof.

The present disclosure relates to exenatide dimer analogs and uses thereof.

BACKGROUND ART

Glycosylation is the process in which a sugar is attached to a protein expressed in vivo and occurs in a Golgi body as an intracellular organelle. Glycoproteins formed by glycosylation are known to be involved in various biological phenomena, such as intracellular junction, development of tissues, immune response, and hormone action. Research on structures of sugars started in 1880, and sugars and glycosylation have been actively studied until now. Recently, research on drug development using glycosylation techniques is proceeding.

Exenatide, which is a functional analog of glucagon-like peptide-1 (GLP-1) isolated from the salivary glands of *Heloderma suspectum* living in the southwestern region of the United States, is used as a peptide medicine for Type 2 diabetes. In recent years, the development of long-acting analogs with improved in vivo stability of GLP-1 analogs including exenatide is being actively made.

Exenatide, of which the scientific name is "Exendin-4", is a bioactive peptide consisting of 39 amino acids. Exenatide is present in the living human body, but is 53% similar to GLP-1 in terms of amino acids and is stable against a degradation enzyme, such as dipeptidyl peptidase-4 (DPP-4), and thus has a relatively longer in vivo half-life than GLP-1.

Exenatide is administered twice a day, prior to breakfast and dinner. Since exenatide is excreted to the kidney, the use of exenatide for patients with severe impairment of kidney functions or end-stage renal diseases is not recommended.

Exenatide does not interact with a drug metabolized into the liver since the excretion of exenatide is not dependent on the liver functions. However, exenatide may interact with other drugs with respect to the absorption thereof since exenatide influences gastric motility.

Moreover, the synthesis of exenatide peptides requires large quantities of reagents and incurs excessive material costs. Moreover, the number of reaction steps is large, intermediates need to be isolated for each step, and purification is not easy due to a high possibility of generation of isomers.

New diabetes medicines using GLP-1 analogs are being actively studied, but most of the studies are focusing on the development of formulations for improving the sustained effect of drugs, and there are few developments of innovative exenatide analogs and mimetics with improved efficacy and stability.

Meanwhile, exenatide has been reported to have side effects, such as a degradation in drug efficacy due to an in vivo immune response. Therefore, the development of peptide drugs using glycosylation occurring in the body is expected to exhibit improved in vivo stability and improved immunogenicity.

Exenatide is an agonist of glucagon-like peptide-1 receptor (GLP-1R) and is used as a peptide medicine for Type 2 diabetes and, recently, the development of long-acting analogs is being actively conducted by improving in vivo stability and reducing side effects such as hypoglycemia, of GLP-1 analogs including exenatide.

GLP-1R and glucagon receptor (GCGR) bind to GLP-1 and glucagon in the body, respectively, to play an important role in maintaining body homeostasis through blood glucose control. It is known that GLP-1R is activated in the cerebral cortex and intestines to play an important role in weight loss by suppressing appetite and reducing intestinal motility. GCGR is known to contribute to weight loss by breaking down accumulated fat by increasing activity of the lipolytic enzymes HSL and ATGL in white adipose tissue and increasing the thermogenesis in brown adipose tissue (REFERENCE). It was confirmed that in a study of metabolic function in patients with Type 2 diabetes and obesity, by co-administration of glucagon and GLP-1, the risk of hyperglycemia of glucagon was prevented by increasing insulin secretion through GLP-1, leading to stabilization of blood glucose levels and an increase in thermogenesis.

The above results suggest that a dual agonist targeting both GCGR and GLP-1R will retain a blood glucose control effect and an enhanced weight loss effect compared with existing a GLP-1 targeting agonist, and the dual expression agonist is expected to be a novel drug candidate for the treatment of both of two types of metabolic diseases, Type 2 diabetes and obesity.

Glycosylation is the process in which a sugar is attached to a protein expressed in vivo and occurs in a Golgi body as an intracellular organelle. Glycoproteins formed by glycosylation are known to be involved in various biological phenomena, such as intracellular junction, development of tissues, immune response, and hormone action. Research on structures of sugars started in 1880, and sugars and glycosylation have been actively studied until now. Recently, research on drug development using glycosylation techniques is proceeding.

Exenatide, which is a functional analog of glucagon-like peptide-1 (GLP-1) isolated from the salivary glands of *Heloderma suspectum* living in the southwestern region of the United States, is used as a peptide medicine for Type 2 diabetes. In recent years, the development of long-acting analogs with improved in vivo stability of GLP-1 analogs including exenatide is being actively made.

Exenatide, of which the scientific name is "Exendin-4", is a bioactive peptide consisting of 39 amino acids. Exenatide is present in the living human body, but is 53% similar to GLP-1 in terms of amino acids and is stable against a degradation enzyme, such as dipeptidyl peptidase-4 (DPP-4), and thus has a relatively longer in vivo half-life than GLP-1.

Exenatide is administered twice a day, prior to breakfast and dinner. Since exenatide is excreted to the kidney, the use of exenatide for patients with severe impairment of kidney functions or end-stage renal diseases is not recommended.

Exenatide does not interact with a drug metabolized into the liver since the excretion of exenatide is not dependent on the liver functions. However, exenatide may interact with other drugs with respect to the absorption thereof since exenatide influences gastric motility.

Moreover, the synthesis of exenatide peptides requires large quantities of reagents and incurs excessive material costs. Moreover, the number of reaction steps is large, intermediates need to be isolated for each step, and purification is not easy due to a high possibility of generation of isomers.

New diabetes medicines using GLP-1 analogs are being actively studied, but most of the studies are focusing on the development of formulations for improving the sustained effect of drugs, and there are few developments of innovative exenatide analogs and mimetics with improved efficacy and stability.

Meanwhile, exenatide has been reported to have side effects, such as a degradation in drug efficacy due to an in vivo immune response. Therefore, the development of peptide drugs using glycosylation occurring in the body is expected to exhibit improved in vivo stability and improved immunogenicity.

SUMMARY

Technical Problem

In the present disclosure, an attempt has been made to develop novel diabetes medicine candidates with improved enhanced drug efficacies and in vivo stability by establishing exenatide analogs in combination with glycosylation.

Accordingly, an aspect of the present disclosure is to provide a glycosylated exenatide analog.

Another aspect of the present disclosure is to provide a pharmaceutical composition containing a glycosylated exenatide analog for alleviation, prevention, or treatment of diabetes.

Still another aspect of the present disclosure is to provide a pharmaceutical composition containing a glycosylated exenatide analog for alleviation, prevention, or treatment of obesity.

Still another aspect of the present disclosure is to provide a food composition containing a glycosylated exenatide analog for alleviation or mitigation of diabetes.

Still another aspect of the present disclosure is to provide a food composition containing a glycosylated exenatide analog for alleviation or mitigation of obesity.

Still another aspect of the present disclosure is to provide a food composition containing a glycosylated exenatide analog for suppression of appetite.

Still another aspect of the present disclosure is to provide a method for alleviating, preventing, or treating diabetes, the method including administering to a subject in need thereof a glycosylated exenatide analog in an amount effective to alleviate, prevent, or treat diabetes.

Still another aspect of the present disclosure is to provide a method for alleviating, preventing, or treating obesity, the method including administering to a subject in need thereof a glycosylated exenatide analog in an amount effective to alleviate, prevent, or treat obesity.

Still another aspect of the present disclosure is to provide use of a glycosylated exenatide analog for alleviating, preventing, or treating diabetes.

Still another aspect of the present disclosure is to provide use of a glycosylated exenatide analog for alleviating, preventing, or treating obesity.

Still another aspect of the present disclosure is to provide use of a glycosylated exenatide analog for suppressing appetite.

The present inventors have attempted to develop novel medicine candidates for diabetes and obesity by establishing, through the application of multiple antigenic peptide (MAP), exenatide dimer analogs with improved blood glucose control ability and in vivo stability developed on the basis of exenatide, a GLP-1R agonist.

An aspect of the present disclosure is to provide an exenatide dimer analog.

Another aspect of the present disclosure is to provide a pharmaceutical composition containing an exenatide dimer analog for alleviation, prevention, or treatment of diabetes.

Another aspect of the present disclosure is to provide a pharmaceutical composition containing an exenatide dimer analog for alleviation, prevention, or treatment of obesity.

Still another aspect of the present disclosure is to provide a food composition containing an exenatide dimer analog for alleviation or mitigation of diabetes.

Still another aspect of the present disclosure is to provide a food composition containing an exenatide dimer analog for alleviation or mitigation of obesity.

Still another aspect of the present disclosure is to provide a food composition containing an exenatide dimer analog for suppression of appetite.

Still another aspect of the present disclosure is to provide a method for alleviating, preventing, or treating diabetes, the method including administering to a subject in need thereof an exenatide dimer analog in an amount effective to alleviate, prevent, or treat diabetes.

Still another aspect of the present disclosure is to provide a method for alleviating, preventing, or treating obesity, the method including administering to a subject in need thereof an exenatide dimer analog in an amount effective to alleviate, prevent, or treat obesity.

Still another aspect of the present disclosure is to provide use of an exenatide dimer analog for alleviating, preventing, or treating diabetes.

Still another aspect of the present disclosure is to provide use of an exenatide dimer analog for alleviating, preventing, or treating obesity.

Still another aspect of the present disclosure is to provide use of an exenatide dimer analog for suppressing appetite.

Solution to Problem

The present disclosure is directed to glycosylated exenatide analogs and uses thereof.

Hereinafter, the present disclosure will be described in more detail.

An embodiment of the present disclosure is directed to a glycosylated exenatide analog.

In the present disclosure, exenatide, which is a GLP-1 receptor agonist, is an analog mimicking GLP-1 (GLP-1 mimetic) that is quickly degraded by dipeptidyl peptidase-IV (DPP-IV). Exenatide is a drug that exhibits the effects of GLP-1 of promoting the secretion of sugar-dependent insulin, suppressing glucagon secretion, gastric emptying, and appetite, and showing β-cell protection effect but is not quickly degraded by DPP-IV.

In the present disclosure, exenatide includes exenatide containing the amino acid sequence of SEQ ID NO: 1 or an exenatide analog having a homology of at least 80%, 90%, or 95% with the amino acid sequence of SEQ ID NO: 1.

In an embodiment of the present disclosure, exenatide may contain the amino acid sequence of SEQ ID NO: 1 and, for example, may consist of the amino acid sequence of SEQ ID NO: 1.

In the present disclosure, in the exenatide analog, some amino acids may be deleted in the amino acid sequence of exenatide and a fatty acid may be conjugated.

In the present disclosure, the deletion may be a deletion of 1 to 15, 1 to 14, 1 to 13, 1 to 12, 1 to 11, 1 to 10, 1 to 9, 4 to 15, 4 to 14, 4 to 13, 4 to 12, 4 to 11, 4 to 10, 4 to 9, 7 to 15, 7 to 14, 7 to 13, 7 to 12, 7 to 11, or 7 to 10, for example, 7 to 9 amino acids in the amino acid sequence of exenatide.

In the present disclosure, the deletion may be a deletion of an amino acid in the N-terminus or C-terminus of the amino acid sequence of exenatide, for example, a deletion of an amino acid in the C-terminus of the amino acid sequence of exenatide.

In an embodiment of the present disclosure, the deletion may be a deletion of 1 to 15, 1 to 14, 1 to 13, 1 to 12, 1 to 11, 1 to 10, 1 to 9, 4 to 15, 4 to 14, 4 to 13, 4 to 12, 4 to 11, 4 to 10, 4 to 9, 7 to 15, 7 to 14, 7 to 13, 7 to 12, 7 to 11, or 7 to 10, for example, 7 to 9 amino acids in the C-terminus of the amino acid sequence of exenatide.

In the exenatide analog of the present disclosure, the fatty acid may be conjugated to various locations of exenatide in which some amino acids are deleted in the amino acid sequence.

In the present disclosure, the fatty acid includes various saturated fatty acids and unsaturated fatty acids known in the art.

In the present disclosure, the fatty acid may be a fatty acid having carbon atoms of $C_3$ to $C_{36}$ and, for example, may be at least one selected from the group consisting of propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, and hexatriacontylic acid, but is not limited thereto.

In an embodiment of the present disclosure, the fatty acid may be conjugated to the N-terminus, the C-terminus, or a Lys residue of the C-terminus of the amino acid sequence of exenatide with a deletion of some amino acids, and for example, the fatty acid may be conjugated to the C-terminus.

In the present disclosure, the conjugation of the fatty acid and exenatide with a deletion of some amino acids in the amino acid sequence includes a direct linkage and/or an indirect linkage.

In the present disclosure, as for the direct linkage, a deleted exenatide-fatty acid conjugation may be made by reacting a functional group, such as a carboxyl group, of the fatty acid with a functional group (e.g., —$NH_2$) of exenatide with a deletion of some amino acids to form a covalent linkage.

In the present disclosure, as for the indirect linkage, a deleted exenatide-fatty acid conjugation may be made by the mediation of a compound commonly used as a linker in the art.

Any compound used as a linker in the art can be used as the linker used in the present disclosure, and an appropriate linker may be selected according to the type of functional group of the deleted exenatide. Examples of the linker may include N-succinimidyl iodoacetate, N-hydroxysuccinimidyl bromoacetate, m-maleimidobenzoyl-N-hydroxysuccinimide ester, m-maleimidobenzoyl-N-hydroxysulfosuccinimide ester, N-maleimidobutyryloxysuccinamide ester, and Lys, but is not limited thereto.

Specifically, the linker may be additionally attached to the C-terminus of exenatide with a deletion of amino acids, and the fatty acid is conjugated to the linker attached to the C-terminus. For example, Lys, as a linker, is attached to the C-terminus of exenatide with a deletion of amino acids, and the fatty acid may be conjugated to the Lys. In such a case, the —$NH_2$ functional group of the additional Lys may react with a carboxyl group of the fatty acid to form a conjugate.

In the present disclosure, the glycosylated exenatide analog may be one in which a sugar is linked to at least one amino acid of an exenatide analog, and a sugar-linked amino acid may be one in which an amino acid is substituted with another amino acid and then a sugar is linked to the another amino acid.

In an embodiment of the present disclosure, the linkage of a sugar may be made at least one position selected from the group consisting of the 17th, 24th, and 28th positions of exenatide consisting of the amino acid sequence of SEQ ID NO: 1, but is not limited thereto.

In an embodiment of the present disclosure, the substitution may be at least one selected from the group consisting of: a substitution of Glu, the 17th amino acid, with Cys in exenatide consisting of the amino acid sequence of SEQ ID NO: 1; a substitution of Glu, the 24th amino acid, with Cys in exenatide consisting of the amino acid sequence of SEQ ID NO: 1; and a substitution of Asn, the 28th amino acid, with Cys in exenatide consisting of the amino acid sequence of SEQ ID NO: 1, but is not limited thereto.

In the present disclosure, the sugar may be mono- to undeca-saccharides, di- to undeca-saccharides, tri- to undeca-saccharides, tetra- to undeca-saccharides, penta- to undeca-saccharides, hexa- to undeca-saccharides, hepta- to undeca-saccharides, octa- to undeca-saccharides, nona- to undeca-saccharides, deca- to undeca-saccharides, and for example, an undeca-sugar, and specifically, the sugar may be bromoacetyl glycan of Structural Formula 1 below and/or 11NC-Asn-Fmoc of Structural Formula 2 below, but is not limited thereto.

[Structural Formula 1]
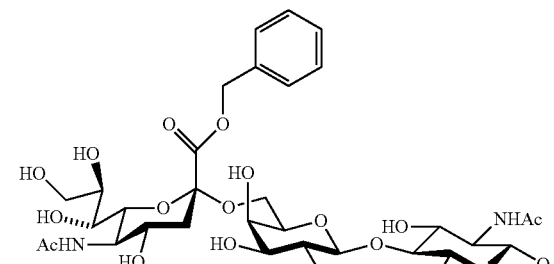
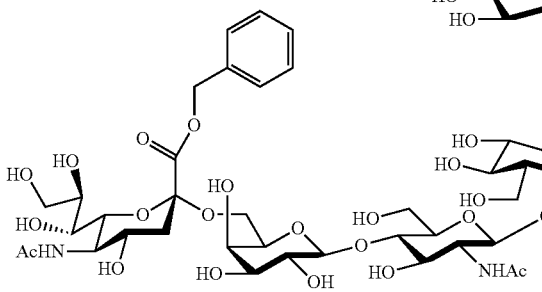
Bromoacetyl glycan
[Structural Formula 2]
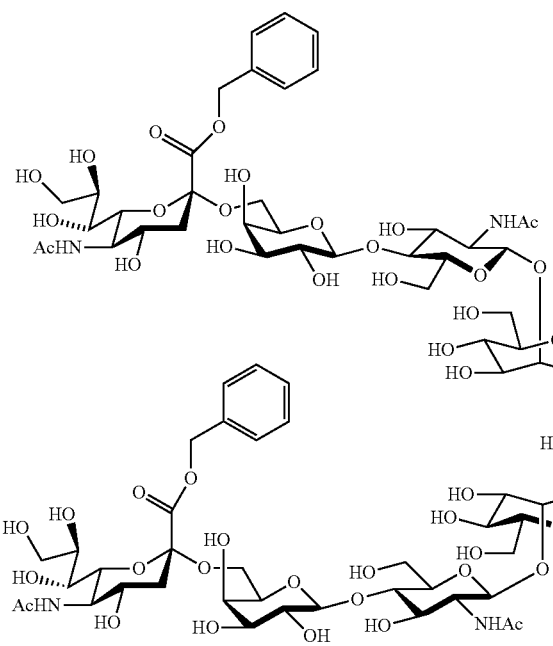
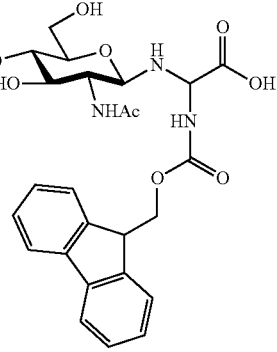
11NC-Asn-Fmoc As used herein, the term "AGM-212" refers to a sequence of positions 1 to 32 in the exenatide sequence consisting of SEQ ID NO: 1, wherein lysine having a side chain to which capric acid is linked is conjugated to the C-terminus of the sequence, and is stated as Ex4(1-32)K-cap.

As used herein, the term "AGM-212(E17C-11 sugar)" refers to a sequence in which glutamic acid (Glu, E) at position 17 is substituted with Cys and a sugar having a structure of undeca-saccharide is linked to the substituted amino acid in the sequence of Ex4(1-32)-cap.

As used herein, the term "AGM-212(N28C-11 sugar)" refers to a sequence in which asparagine (Asn, N) at position 28 is substituted with Cys and a sugar having a structure of undeca-saccharide is linked to the substituted amino acid in the sequence of Ex4(1-32)-cap.

As used herein, the term "AGM-212(N28-11 sugar)" refers to a sequence in which a sugar having a structure of undeca-saccharide is linked to asparagine at position 28 in the sequence of Ex4(1-32)-cap.

As used herein, the term "AGM-212(E24-11 sugar)" refers to a sequence in which glutamic acid at position 24 is substituted with Cys and a sugar having a structure of undeca-saccharide is linked to the substituted amino acid in the sequence of Ex4(1-32)-cap.

As used herein, the term "AGM-212(E17C-11 sugar & E24C-11 sugar)" refers to a sequence in which glutamic acid at position 17 is substituted with Cys and glutamic acid at position 24 is substituted and a sugar having a structure of undeca-saccharide is linked to each of the substituted amino acids in the sequence of Ex4(1-32)-cap.

As used herein, the term "AGM-212(E17C-11 sugar & N28C-11 sugar)" refers to a sequence in which glutamic acid at position 17 is substituted with Cys and asparagine at position 28 is substituted and a sugar having a structure of undeca-saccharide is linked to each of the substituted amino acids in the sequence of Ex4(1-32)-cap.

Another embodiment of the present disclosure is directed to a pharmaceutical composition containing a glycosylated exenatide analog for alleviation, prevention, or treatment of diabetes.

Still another embodiment of the present disclosure is directed to a pharmaceutical composition containing a glycosylated exenatide analog for alleviation, prevention, or treatment of obesity.

Since the description of the glycosylated exenatide analog in the pharmaceutical composition of the present disclosure is as described above, the description thereof is omitted.

The pharmaceutical composition of the present disclosure may contain a pharmaceutically acceptable carrier.

The pharmaceutically acceptable carrier in the present disclosure is commonly used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oils, and the like.

The pharmaceutical composition of the present disclosure may further contain, in addition to the above ingredients, a lubricant, a wetting agent, a sweetening agent, a flavoring agent, an emulsifier, a suspending agent, a preservative, and the like. Appropriate pharmaceutically acceptable carriers and agents are described in detail in Remington's Pharmaceutical Sciences (19th ed., 1995).

The pharmaceutical composition of the present disclosure may be orally or parenterally administered, and examples of parenteral administration may include intravenous injection, subcutaneous injection, intramuscular injection, intraperitoneal injection, percutaneous administration, and the like.

The appropriate dose of the pharmaceutical composition of the present disclosure varies depending on factors, such as formulation method, administration method, patient's age, body weight, and sex, pathological condition, diet, administration time, administration route, excretion rate, and response sensitivity. An ordinarily skilled practitioner can easily determine and prescribe a dose that is effective for desired treatment or prevention.

According to a preferable embodiment of the present disclosure, the daily dose of the pharmaceutical composition of the present disclosure is 0.001-10000 mg/kg.

The pharmaceutical composition of the present disclosure may be prepared into a unit dosage form or in the form of being contained in a multi-dose container by using a pharmaceutically acceptable carrier and/or excipient according to a method that can be easily performed by a person skilled in the art to which the present disclosure pertains. The formulation may be in the form of a solution in an oily or aqueous medium, a suspension, or an emulsion, or in the form of an extract, a powder, granules, a tablet, or a capsule, and may further contain a dispersant or a stabilizer.

As used herein, the term "containing as an active ingredient" refers to the inclusion of an amount that is sufficient to attain the efficacy or activity of the following exenatide analog. The quantitative upper limit in the composition of the present disclosure may be selected within an appropriate range by a person skilled in the art.

Still another embodiment of the present disclosure is directed to a food composition containing a glycosylated exenatide analog for alleviation or mitigation of diabetes.

Still another embodiment of the present disclosure is directed to a food composition containing a glycosylated exenatide analog for alleviation or mitigation of obesity.

Still another embodiment of the present disclosure is directed to a food composition containing a glycosylated exenatide analog for suppression of appetite.

Since the description of the glycosylated exenatide analog in the food composition of the present disclosure is as described above, the description thereof is omitted.

When the composition of the present disclosure is a food composition, the food composition may be prepared in the form of a powder, granules, a tablet, a capsule, or a drink. Examples thereof are various foods such as candies, drinks, chewing gums, teas, vitamin complexes, health supplement foods, and the like.

The food composition of the present disclosure may contain as an active ingredient an ingredient that is commonly added during food manufacturing, and examples thereof include proteins, carbohydrates, fats, nutrients, seasonings, and flavoring agents.

Examples of the carbohydrates are: common saccharides, such as monosaccharides (e.g., glucose and fructose), disaccharides (e.g., maltose, sucrose, and oligosaccharides), and polysaccharides (e.g., dextrin and cyclodextrin); and sugar alcohols, such as xylitol, sorbitol, and erythritol. As flavoring agents, natural flavoring agents (thaumatin, stevia extracts (e.g., rebaudioside A, glycyrrhizin, etc.)) and synthetic flavoring agents (saccharin, aspartame, etc.) may be used. For example, the food composition of the present disclosure, when prepared as a drink, may contain citric acid, liquefied fructose, sugar, glucose, acetic acid, malic acid, fruit juice, an *Eucommia ulmoides* extract, a jujube extract, a licorice extract, and the like, in addition to the compound of the present disclosure.

Still another aspect of the present disclosure is to provide a method for alleviating, preventing, or treating diabetes, the method including administering to a subject in need thereof an exenatide analog in an amount effective to alleviate, prevent, or treat diabetes.

Still another aspect of the present disclosure is to provide a method for alleviating, preventing, or treating obesity, the method including administering to a subject in need thereof an exenatide analog in an amount effective to alleviate, prevent, or treat obesity.

Still another aspect of the present disclosure is to provide use of an exenatide analog for alleviating, preventing, or treating diabetes.

Still another aspect of the present disclosure is to provide use of an exenatide analog for alleviating, preventing, or treating obesity.

Still another aspect of the present disclosure is to provide use of an exenatide analog for suppressing appetite.

The present disclosure is directed to exenatide dimer analogs and uses thereof.

Hereinafter, the present disclosure will be described in more detail.

An embodiment of the present disclosure is directed to an exenatide dimer analog.

In the present disclosure, an exenatide dimer analog may include: a first body composed of an exenatide analog including a deletion of 1 to 15 amino acids in the amino acid sequence of exenatide and a conjugation of a fatty acid thereto; and a second body composed of glucagon or an exenatide analog including a deletion of 1 to 15 amino acids in the amino acid sequence of exenatide and a conjugation of a fatty acid thereto, wherein the first body and the second body may be linked to form a dimer analog.

In the present disclosure, exenatide, which is a GLP-1 receptor agonist, is an analog mimicking GLP-1 (GLP-1 mimetic) that is quickly degraded by dipeptidyl peptidase-IV (DPP-IV). Exenatide is a drug that exhibits the effects of GLP-1 of promoting the secretion of sugar-dependent insulin, suppressing glucagon secretion, gastric emptying, and appetite, and showing β-cell protection effect but is not quickly degraded by DPP-IV.

In the present disclosure, exenatide includes exenatide containing the amino acid sequence of SEQ ID NO: 1 or an exenatide analog having a homology of at least 80%, 90%, or 95% with the amino acid sequence of SEQ ID NO: 1.

In an embodiment of the present disclosure, exenatide may contain the amino acid sequence of SEQ ID NO: 1 and, for example, may consist of the amino acid sequence of SEQ ID NO: 1.

In the present disclosure, glucagon includes glucagon containing the amino acid sequence of SEQ ID NO: 2 or a glucagon analog having a homology of at least 80%, 90%, or 95% with the amino acid sequence of SEQ ID NO: 2.

In an embodiment of the present disclosure, glucagon may contain the amino acid sequence of SEQ ID NO: 2 and, for example, may consist of the amino acid sequence of SEQ ID NO: 2.

In the present disclosure, when the second body is an exenatide analog, the first body and the second body may be linked via a disulfide linkage, but is not limited thereto.

In the present disclosure, when the second body is glucagon, the first body and the second body may be linked by adding a Lys residue to the C-terminus of the first body and linking the second boy composed of glucagon to a side chain thereof or via a disulfide linkage, but is not limited thereto.

In the present disclosure, in the exenatide analog, some amino acids may be deleted in the amino acid sequence of exenatide and a fatty acid may be conjugated.

In the present disclosure, the deletion may be a deletion of 1 to 15, 1 to 14, 1 to 13, 1 to 12, 1 to 11, 1 to 10, 1 to 9, 4 to 15, 4 to 14, 4 to 13, 4 to 12, 4 to 11, 4 to 10, 4 to 9, 7 to 15, 7 to 14, 7 to 13, 7 to 12, 7 to 11, or 7 to 10, for example, 7 to 9 amino acids in the amino acid sequence of exenatide.

In the present disclosure, the deletion may be a deletion of an amino acid in the N-terminus or C-terminus of the amino acid sequence of exenatide, for example, a deletion of an amino acid in the C-terminus of the amino acid sequence of exenatide.

In an embodiment of the present disclosure, the deletion may be a deletion of 1 to 15, 1 to 14, 1 to 13, 1 to 12, 1 to 11, 1 to 10, 1 to 9, 4 to 15, 4 to 14, 4 to 13, 4 to 12, 4 to 11, 4 to 10, 4 to 9, 7 to 15, 7 to 14, 7 to 13, 7 to 12, 7 to 11, or 7 to 10, for example, 7 to 9 amino acids in the C-terminus of the amino acid sequence of exenatide.

In the exenatide analog of the present disclosure, the fatty acid may be conjugated to various locations of exenatide in which some amino acids are deleted in the amino acid sequence.

In the present disclosure, the fatty acid includes various saturated fatty acids and unsaturated fatty acids known in the art.

In the present disclosure, the fatty acid may be a fatty acid having carbon atoms of $C_3$ to $C_{36}$ and, for example, may be at least one selected from the group consisting of propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, and hexatriacontylic acid, but is not limited thereto.

In an embodiment of the present disclosure, the fatty acid may be conjugated to the N-terminus, the C-terminus, or a Lys residue of the C-terminus of the amino acid sequence of exenatide with a deletion of some amino acids, and for example, the fatty acid may be conjugated to the C-terminus.

In the present disclosure, the conjugation of the fatty acid and exenatide with a deletion of some amino acids in the amino acid sequence includes a direct linkage and/or an indirect linkage.

In the present disclosure, as for the direct linkage, a deleted exenatide-fatty acid conjugation may be made by reacting a functional group, such as a carboxyl group, of the fatty acid with a functional group (e.g., —NH$_2$) of exenatide with a deletion of some amino acids to form a covalent linkage.

In the present disclosure, as for the indirect linkage, a deleted exenatide-fatty acid conjugation may be made by the mediation of a compound commonly used as a linker in the art.

Any compound used as a linker in the art can be used as the linker used in the present disclosure, and an appropriate linker may be selected according to the type of functional group of the deleted exenatide. Examples of the linker may include N-succinimidyl iodoacetate, N-hydroxysuccinimidyl bromoacetate, m-maleimidobenzoyl-N-hydroxysuccinimide ester, m-maleimidobenzoyl-N-hydroxysulfosuccinimide ester, N-maleimidobutyryloxysuccinamide ester, and Lys, but is not limited thereto.

Specifically, the linker may be additionally attached to the C-terminus of exenatide with a deletion of amino acids, and the fatty acid is conjugated to the linker attached to the C-terminus. For example, Lys, as a linker, is attached to the C-terminus of exenatide with a deletion of amino acids, and the fatty acid may be conjugated to the Lys. In such a case, the —NH$_2$ functional group of the additional Lys may react with a carboxyl group of the fatty acid to form a conjugate.

In the present disclosure, the exenatide dimer analog may include a first body and a second body, wherein a sugar may be linked to one amino acid of each of the bodies.

In the present disclosure, the exenatide dimer analog may include a first body and a second body, wherein one amino acid may be substituted with another amino acid in each of the bodies and a sugar may be linked to the substituted amino acid.

In an embodiment of the present disclosure, the linkage of a sugar may be made at at least one position selected from the group consisting of the 17th, 24th, and 28th positions of exenatide consisting of the amino acid sequence of SEQ ID NO: 1, but is not limited thereto.

In an embodiment of the present disclosure, the substitution may be at least one selected from the group consisting of: a substitution of Glu, the 17th amino acid, with Cys in exenatide consisting of the amino acid sequence of SEQ ID NO: 1; a substitution of Glu, the 24th amino acid, with Cys in exenatide consisting of the amino acid sequence of SEQ ID NO: 1; and a substitution of Asn, the 28th amino acid, with Cys in exenatide consisting of the amino acid sequence of SEQ ID NO: 1, but is not limited thereto.

In an embodiment of the present disclosure, the linkage of a sugar may be made at at least one position selected from the group consisting of the 16th and 24th positions of glucagon consisting of the amino acid sequence of SEQ ID NO: 2, but is not limited thereto.

In an embodiment of the present disclosure, the substitution may be at least one selected from the group consisting of: a substitution of Ser, the 16th amino acid, with Cys or Asn in glucagon consisting of the amino acid sequence of SEQ ID NO: 2; and a substitution of Gln, the 24th amino acid, with Cys or Asn in glucagon consisting of the amino acid sequence of SEQ ID NO: 2, but is not limited thereto.

In the present disclosure, the sugar may be mono- to undeca-saccharides, di- to undeca-saccharides, tri- to undeca-saccharides, tetra- to undeca-saccharides, penta- to undeca-saccharides, hexa- to undeca-saccharides, hepta- to undeca-saccharides, octa- to undeca-saccharides, nona- to undeca-saccharides, deca- to undeca-saccharides, and for example, an undeca-saccharide, and specifically, the sugar may be bromoacetyl glycan of Structural Formula 1 below and/or 11NC-Asn-Fmoc of Structural Formula 2 below, but is not limited thereto.

[Structural Formula 1]

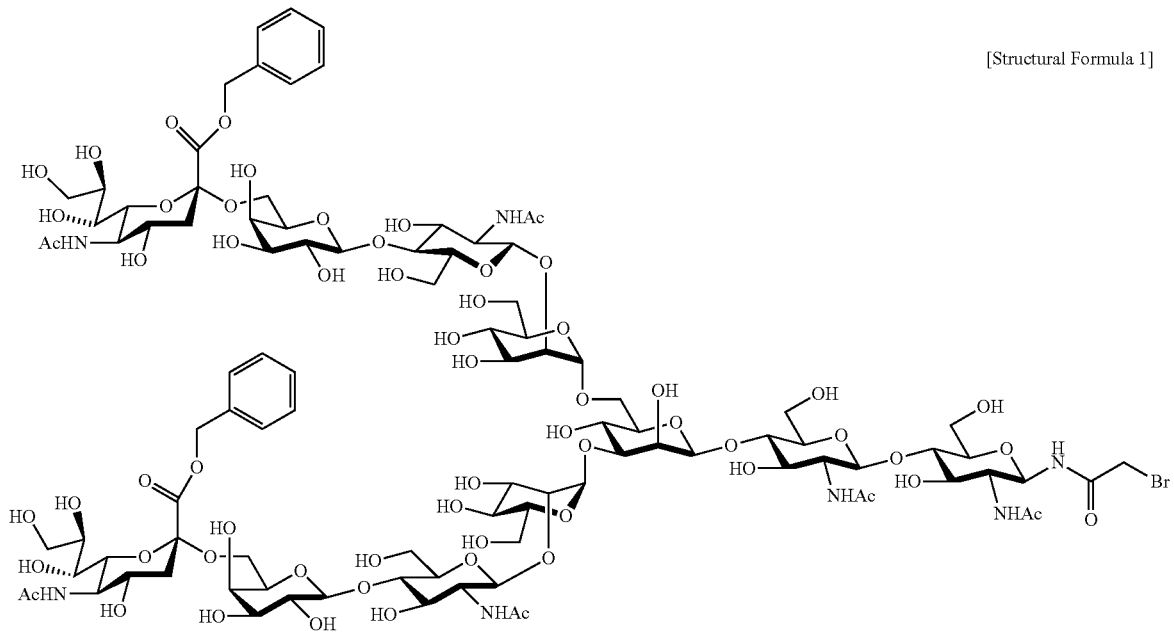

Bromoacetyl glycan

-continued

[Structural Formula 2]

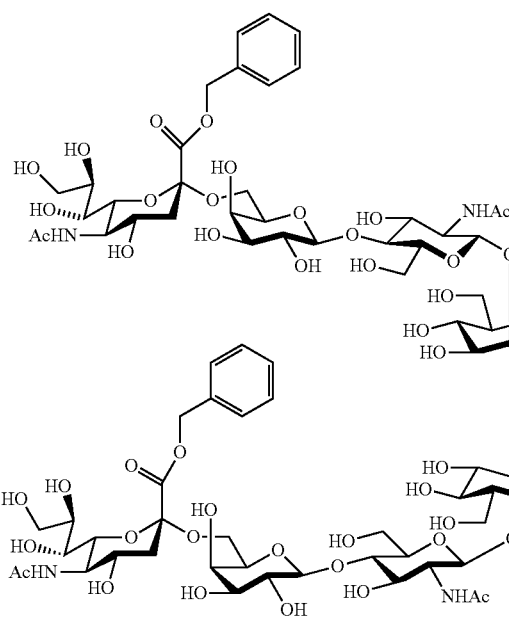

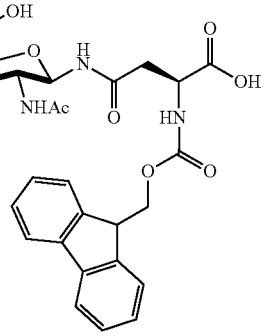

11NC-Asn-Fmoc

As used herein, the term "AGM-212" refers to a sequence of positions 1 to 32 in the exenatide sequence consisting of SEQ ID NO: 1, wherein lysine having a side chain to which capric acid is linked is conjugated to the C-terminus of the sequence, and is stated as Ex4(1-32)K-cap.

As used herein, the term "AGM-212-1" refers a sequence of a dimer of two sequences linked via a disulfide linkage, each of which has a substitution of glutamic acid (Glu, E) at position 17 with Cys in the sequence of AGM-212, wherein in each of the two sequences, glutamic acid at position 24 is substituted with Cys and an undeca-saccharide is linked to the amino acid.

As used herein, the term "AGM-212-2" refers a sequence of a dimer of two sequences linked via a disulfide linkage, each of which has a substitution of glutamic acid at position 17 with Cys in the sequence of AGM-212, wherein in each of the two sequences, asparagine at position 28 is substituted with Cys and an undeca-saccharide is linked to the amino acid.

As used herein, the term "AGM-212-3" refers to a sequence in which Lys is added to the C-terminus and glucagon is linked to a side chain thereof in the sequence of AGM-212.

As used herein, the term "AGM-212-4" refers to a sequence in which an undeca-saccharide is linked to asparagine at position 28, Lys is added to the C-terminus, and glucagon is linked to a side chain thereof in the sequence of AGM-212.

As used herein, the term "AGM-212-5" refers to a sequence in which an undeca-saccharide is linked to asparagine at position 28, Lys is added to the C-terminus, and glucagon is linked to a side chain thereof in the sequence of AGM-212, wherein in the sequence of glucagon, serine (Ser, S) at position 16 is substituted with 11NC-Asn and an undeca-saccharide is linked thereto.

As used herein, the term "AGM-212-6" refers to a sequence in which an undeca-saccharide is linked to asparagine at position 28, Lys is added to the C-terminus, and glucagon is linked to a side chain thereof in the sequence of AGM-212, wherein in the sequence of glucagon, glutamine (Gln, Q) at position 24 is substituted with 11NC-Asn and an undeca-saccharide is linked thereto.

As used herein, the term "AGM-212-7" is a dimer formed, via a disulfide linkage, of: a sequence in which glutamic acid (Glu, E) at position 17 is substituted with Cys, glutamic acid at position 24 is substituted with Cys, and an undeca-saccharide is linked thereto in the sequence AGM-212; and a sequence in which serine (Ser, S) at position 16 is substituted with Cys and an undeca-saccharide is linked thereto and glutamine (Gln, Q) at position 24 is substituted with Cys in the sequence of glucagon.

As used herein, the term "AGM-212-8" is a dimer formed, via a disulfide linkage, of: a sequence in which glutamic acid (Glu, E) at position 17 is substituted with Cys, and glutamic acid at position 24 is substituted with Cys, and an undeca-saccharide is linked thereto in the sequence AGM-212; and a sequence in which glutamine (Gln, Q) at position 24 is substituted with Cys and an undeca-saccharide is linked thereto and serine at position 16 is substituted with Cys in the sequence of glucagon.

As used herein, the term "disulfide linkage" refers to a disulfide linkage of C17-C17 of two AGM-212 after E17 is substituted with C17 in each of the two AGM-212, but is not limited thereto.

Another embodiment of the present disclosure is directed to a pharmaceutical composition containing an exenatide dimer analog for alleviation, prevention, or treatment of diabetes.

Still another embodiment of the present disclosure is directed to a pharmaceutical composition containing an exenatide dimer analog for alleviation, prevention, or treatment of obesity.

Since the description of the exenatide dimer analog in the pharmaceutical composition of the present disclosure is as described above, the description thereof is omitted.

The pharmaceutical composition of the present disclosure may contain a pharmaceutically acceptable carrier.

The pharmaceutically acceptable carrier in the present disclosure is commonly used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oils, and the like.

The pharmaceutical composition of the present disclosure may further contain, in addition to the above ingredients, a lubricant, a wetting agent, a sweetening agent, a flavoring agent, an emulsifier, a suspending agent, a preservative, and the like. Appropriate pharmaceutically acceptable carriers and agents are described in detail in Remington's Pharmaceutical Sciences (19th ed., 1995).

The pharmaceutical composition of the present disclosure may be orally or parenterally administered, and examples of parenteral administration may include intravenous injection, subcutaneous injection, intramuscular injection, intraperitoneal injection, percutaneous administration, and the like.

The appropriate dose of the pharmaceutical composition of the present disclosure varies depending on factors, such as formulation method, administration method, patient's age, body weight, and sex, pathological condition, diet, administration time, administration route, excretion rate, and response sensitivity. An ordinarily skilled practitioner can easily determine and prescribe a dose that is effective for desired treatment or prevention.

According to a preferable embodiment of the present disclosure, the daily dose of the pharmaceutical composition of the present disclosure is 0.001-10000 mg/kg.

The pharmaceutical composition of the present disclosure may be prepared into a unit dosage form or in the form of being contained in a multi-dose container by using a pharmaceutically acceptable carrier and/or excipient according to a method that can be easily performed by a person skilled in the art to which the present disclosure pertains. The formulation may be in the form of a solution in an oily or aqueous medium, a suspension, or an emulsion, or in the form of an extract, a powder, granules, a tablet, or a capsule, and may further contain a dispersant or a stabilizer.

As used herein, the term "containing as an active ingredient" refers to the inclusion of an amount that is sufficient to attain the efficacy or activity of the following exenatide analog. The quantitative upper limit in the composition of the present disclosure may be selected within an appropriate range by a person skilled in the art.

Still another embodiment of the present disclosure is directed to a food composition containing an exenatide dimer analog for alleviation or mitigation of diabetes.

Still another embodiment of the present disclosure is directed to a food composition containing an exenatide dimer analog for alleviation or mitigation of obesity.

Still another embodiment of the present disclosure is directed to a food composition containing an exenatide dimer analog for suppression of appetite.

Since the description of the exenatide dimer analog in the food composition of the present disclosure is as described above, the description thereof is omitted.

When the composition of the present disclosure is a food composition, the food composition may be prepared in the form of a powder, granules, a tablet, a capsule, or a drink. Examples thereof are various foods such as candies, drinks, chewing gums, teas, vitamin complexes, health supplement foods, and the like.

The food composition of the present disclosure may contain as an active ingredient an ingredient that is commonly added during food manufacturing, and examples thereof include proteins, carbohydrates, fats, nutrients, seasonings, and flavoring agents.

Examples of the carbohydrates are: common saccharides, such as monosaccharides (e.g., glucose and fructose), disaccharides (e.g., maltose, sucrose, and oligosaccharides), and polysaccharides (e.g., dextrin and cyclodextrin); and sugar alcohols, such as xylitol, sorbitol, and erythritol. As flavoring agents, natural flavoring agents (thaumatin, stevia extracts (e.g., rebaudioside A, glycyrrhizin, etc.)) and synthetic flavoring agents (saccharin, aspartame, etc.) may be used. For example, the food composition of the present disclosure, when prepared as a drink, may contain citric acid, liquefied fructose, sugar, glucose, acetic acid, malic acid, fruit juice, an *Eucommia ulmoides* extract, a jujube extract, a licorice extract, and the like, in addition to the compound of the present disclosure.

Still another aspect of the present disclosure is to provide a method for alleviating, preventing, or treating diabetes, the method including administering to a subject in need thereof an exenatide analog in an amount effective to alleviate, prevent, or treat diabetes.

Still another aspect of the present disclosure is to provide a method for alleviating, preventing, or treating obesity, the method including administering to a subject in need thereof an exenatide analog in an amount effective to alleviate, prevent, or treat obesity.

Still another aspect of the present disclosure is to provide use of an exenatide analog for alleviating, preventing, or treating diabetes.

Still another aspect of the present disclosure is to provide use of an exenatide analog for alleviating, preventing, or treating obesity.

Still another aspect of the present disclosure is to provide use of an exenatide analog for suppressing appetite.

As used herein, the term "diabetes" refers to a chronic disease characterized by a relative or absolute deficiency of insulin, causing glucose-intolerance. The term "diabetes" includes all types of diabetes, for example, Type 1 diabetes, Type 2 diabetes, or hereditary diabetes. Type 1 diabetes is the insulin-dependent diabetes, which is mainly caused by β-cell disruption. Type 2 diabetes is the insulin-independent diabetes, which is caused by an insufficient secretion of insulin after eating or by insulin resistance.

As used herein, the term "obesity" refers to a condition in which adipose tissues are excessively accumulated in the body so as to cause health disorders.

As used herein, the term "suppressing appetite" refers to the suppression of a desire to consume food.

Advantageous Effects of Invention

The present disclosure is directed to exenatide analogs with a particular residue glycosylated and uses thereof, and the present disclosure provides a novel diabetes medicine showing an improved in-vivo stability compared with conventional exenatide and analogs thereof.

The present disclosure is directed to exenatide dimer analogs and uses thereof, and the present disclosure provides a novel diabetes medicine showing an improved in-vivo stability compared with conventional exenatide and analogs thereof.

BEST MODE FOR CARRYING OUT THE INVENTION

Figure 1:
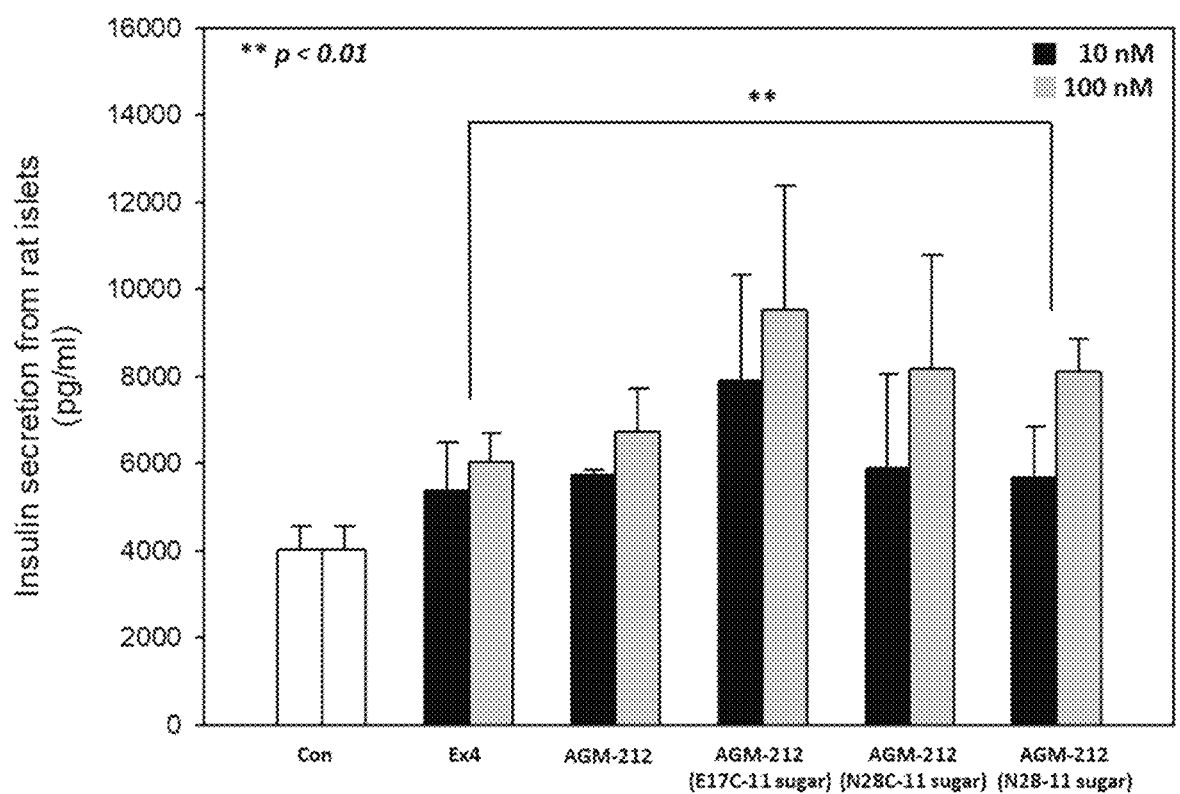
FIG. 1 shows the results of analyzing insulin secretion ability of glycosylated AGM-212 analogs (Examples 1, 2, and 4) from rat islets through rat insulin ELISA according to an exemplary embodiment of the present disclosure.

An exenatide dimer analog including: a first body composed of an exenatide analog including a deletion of 1 to 15 amino acids in the amino acid sequence of exenatide and a conjugation of a fatty acid thereto; and a second body composed of glucagon or an exenatide analog including a deletion of 1 to 15 amino acids in the amino acid sequence of exenatide and a conjugation of a fatty acid thereto, wherein the first body and the second body may be linked to form a dimer analog.

DETAILED DESCRIPTION

Hereinafter, the present disclosure will be described in more detail by the following examples. However, these examples are used only for illustration, and the scope of the present disclosure is not limited by these examples.

I. Glycosylated Exenatide Analog

Example 1: Preparation of AGM-212 (E17C-11 Sugar)

1-1. Chemical Formula 1

To prepare Ex4(1-32)K-cap, which was the sequence of AGM-212, Fmoc-Lys(dde)-OH and DMF were added to trityl resin to prepare Fmoc-Lys(dde) trityl resin. DMF containing 20% piperidine, Fmoc-Ser(tBu)-OH, and hydroxyl-benzo triazole (HOBt) were added to the Fmoc-Lys(dde) trityl resin to prepare Fmoc-Ser(tBu)-Lys(dde) trityl resin. By the same preparation method as above, Fmoc-Pro-OH, Fmoc-Gly-OH, Fmoc-Gly-OH, Fmoc-Asn(trt)-OH, Fmoc-Lys(boc)-OH, Fmoc-Leu-OH, Fmoc-Trp(Boc)-OH, Fmoc-Glu(tBu)-OH, Fmoc-Ile-OH, Fmoc-Phe-OH, Fmoc-Leu-OH, Fmoc-Arg(pbf)-OH, Fmoc-Val-OH, Fmoc-Ala-OH, Fmoc-Glu(tBu)-OH, Fmoc-Glu(tBu)-OH, Fmoc-Glu(tBu)-OH, Fmoc-Met-OH, Fmoc-Gln(trt)-OH, Fmoc-Lys(boc)-OH, Fmoc-Ser(tBu)-OH, Fmoc-Le-OH, Fmoc-Asp(tBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(tBu)-OH, Fmoc-Gly-OH, and Fmoc-His(trt)-OH were sequentially added to the Fmoc-Ser(tBu)-Lys(dde) trityl resin to prepare Chemical Formula 1 below.

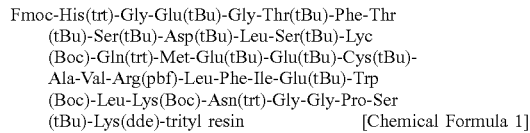

Fmoc-His(trt)-Gly-Glu(tBu)-Gly-Thr(tBu)-Phe-Thr(tBu)-Ser(tBu)-Asp(tBu)-Leu-Ser(tBu)-Lyc(Boc)-Gln(trt)-Met-Glu(tBu)-Glu(tBu)-Cys(tBu)-Ala-Val-Arg(pbf)-Leu-Phe-Ile-Glu(tBu)-Trp(Boc)-Leu-Lys(Boc)-Asn(trt)-Gly-Gly-Pro-Ser(tBu)-Lys(dde)-trityl resin    [Chemical Formula 1]

1-2. Chemical Formula 2

DMF containing 2% $NH_2NH_2 \cdot H_2O$ was added to Chemical Formula 1, followed by removal of dde, thereby preparing Chemical Formula 2.

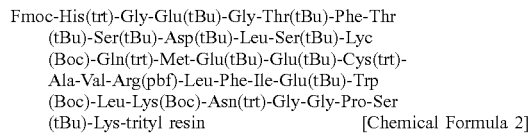

Fmoc-His(trt)-Gly-Glu(tBu)-Gly-Thr(tBu)-Phe-Thr(tBu)-Ser(tBu)-Asp(tBu)-Leu-Ser(tBu)-Lyc(Boc)-Gln(trt)-Met-Glu(tBu)-Glu(tBu)-Cys(trt)-Ala-Val-Arg(pbf)-Leu-Phe-Ile-Glu(tBu)-Trp(Boc)-Leu-Lys(Boc)-Asn(trt)-Gly-Gly-Pro-Ser(tBu)-Lys-trityl resin    [Chemical Formula 2]

1-3. Chemical Formula 3

Capric acid and DMF containing HOBt and DIC were added to Chemical Formula 2 to prepare Chemical Formula 3.

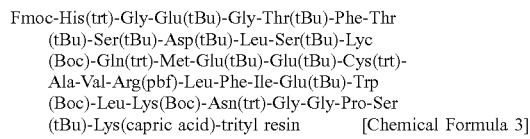

Fmoc-His(trt)-Gly-Glu(tBu)-Gly-Thr(tBu)-Phe-Thr(tBu)-Ser(tBu)-Asp(tBu)-Leu-Ser(tBu)-Lyc(Boc)-Gln(trt)-Met-Glu(tBu)-Glu(tBu)-Cys(trt)-Ala-Val-Arg(pbf)-Leu-Phe-Ile-Glu(tBu)-Trp(Boc)-Leu-Lys(Boc)-Asn(trt)-Gly-Gly-Pro-Ser(tBu)-Lys(capric acid)-trityl resin    [Chemical Formula 3]

1.4. Chemical Formula 4

The protective group of Chemical Formula 3 was cleaved, followed by purification, thereby preparing Chemical Formula 4.

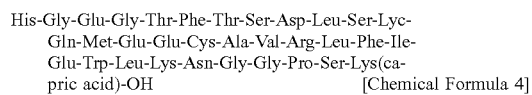

His-Gly-Glu-Gly-Thr-Phe-Thr-Ser-Asp-Leu-Ser-Lyc-Gln-Met-Glu-Glu-Cys-Ala-Val-Arg-Leu-Phe-Ile-Glu-Trp-Leu-Lys-Asn-Gly-Gly-Pro-Ser-Lys(capric acid)-OH    [Chemical Formula 4]

1-5. Chemical Formula 5

Bromoacetyl glycan (11 sugar) having a structure of undeca-saccharide, NaOH, and a phosphate buffer were added to Chemical Formula 4, thereby preparing Chemical Formula 5.

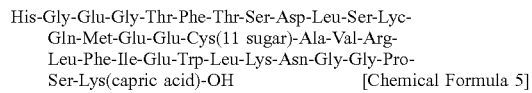

His-Gly-Glu-Gly-Thr-Phe-Thr-Ser-Asp-Leu-Ser-Lyc-Gln-Met-Glu-Glu-Cys(11 sugar)-Ala-Val-Arg-Leu-Phe-Ile-Glu-Trp-Leu-Lys-Asn-Gly-Gly-Pro-Ser-Lys(capric acid)-OH    [Chemical Formula 5]

Example 2: Preparation of AGM-212 (N28C-11 Sugar)

Chemical Formula 6 was prepared by the same method as in the preparation procedure of Example 1 while Fmoc-Asn(tBu)-OH, the 28th amino acid, was replaced with Fmoc-Cys(trt)-OH.

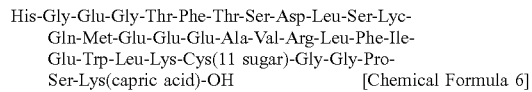

His-Gly-Glu-Gly-Thr-Phe-Thr-Ser-Asp-Leu-Ser-Lyc-Gln-Met-Glu-Glu-Glu-Ala-Val-Arg-Leu-Phe-Ile-Glu-Trp-Leu-Lys-Cys(11 sugar)-Gly-Gly-Pro-Ser-Lys(capric acid)-OH    [Chemical Formula 6]

Example 3: Preparation of AGM-212 (N28-11 Sugar)

Chemical Formula 7 was prepared by the same method as in the preparation procedure of Example 1 while Fmoc-Asn(tBu)-OH, the 28th amino acid, was replaced with Fmoc-Cys(trt)-OH in Chemical Formula 2.

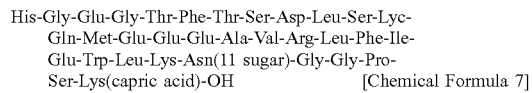

His-Gly-Glu-Gly-Thr-Phe-Thr-Ser-Asp-Leu-Ser-Lyc-Gln-Met-Glu-Glu-Glu-Ala-Val-Arg-Leu-Phe-Ile-Glu-Trp-Leu-Lys-Asn(11 sugar)-Gly-Gly-Pro-Ser-Lys(capric acid)-OH    [Chemical Formula 7]

TABLE 1

| Name | Sequence |
|---|---|
| Ex4 | HGEGTFTSDL SKQMEEEAVR LFIEWLKNGG PSSGAPPPS |
| AGM-212 | HGEGTFTSDL SKQMEEEAVR LFIEWLKNGG PSK-capric acid |
| AGM-212 (E17C-11 sugar) | HGEGTFTSDL SKQMEEC (11 sugar)AVR LFIEWLKNGG PSK-capric acid |
| AGM-212 (E24C-11 sugar) | HGEGTFTSDL SKQMEEEAVR LFIC(11 sugar)WLKNGG PSK-capric acid |
| AGM-212 (N28C-11 sugar) | HGEGTFTSDL SKQMEEEAVR LFIEWLKC(11 sugar)GG PSK-capric acid |
| AGM-212 (N28-11 sugar) | HGEGTFTSDL SKQMEEEAVR LFIEWLKN(11 sugar)GG PSK-capric acid |
| AGM-212 (E17C-11 sugar & E24C-11 sugar | HGEGTFTSDL SKQMEEC (11 sugar)AVR LFIC (11 sugar)WLKNGG PSK-capric acid |

TABLE 1-continued

| Name | Sequence |
| --- | --- |
| AGM-212<br>(E17C-11 sugar &<br>N28C-11 sugar | HGEGTFTSDL SKQMEEC<br>(11 sugar)AVR LFICWLC<br>(11 sugar)NGG PSK-capric<br>acid |

Example 4: Preparation of AGM-212 (E24C-11 Sugar)

Chemical Formula 8 was prepared by the same method as in the preparation procedure of Example 1 while Fmoc-Glu (tBu)-OH, the 24th amino acid, was replaced with Fmoc-Cys(trt)-OH.

His-Gly-Glu-Gly-Thr-Phe-Thr-Ser-Asp-Leu-Ser-Lyc-
Gln-Met-Glu-Glu-Glu-Ala-Val-Arg-Leu-Phe-Ile-
Cys(11 sugar)-Trp-Leu-Lys-Asn-Gly-Gly-Pro-
Ser-Lys(capric acid)-OH   [Chemical Formula 8]

Example 5: Preparation of AGM-212(E17C-11 Sugar & E24C-11 Sugar)

5-1. Chemical Formula 9

Chemical Formula 9 was prepared by the same method as in the preparation procedure of Example 1 while Fmoc-Glu (tBu)-OH, the 24th amino acid, was replaced with Fmoc-Cys(trt)-OH.

His-Gly-Glu-Gly-Thr-Phe-Thr-Ser-Asp-Leu-Ser-Lyc-
Gln-Met-Glu-Glu-Cys-Ala-Val-Arg-Leu-Phe-Ile-
Cys-Trp-Leu-Lys-Asn-Gly-Gly-Pro-Ser-Lys(ca-
pric acid)-OH   [Chemical Formula 9]

5-2. Chemical Formula 11

Bromoacetyl glycan (11 sugar) having a structure of undeca-saccharide, NaOH, and a phosphate buffer were added to Chemical Formula 9, thereby preparing Chemical Formula 10.

His-Gly-Glu-Gly-Thr-Phe-Thr-Ser-Asp-Leu-Ser-Lyc-
Gln-Met-Glu-Glu-Cys(11 sugar)-Ala-Val-Arg-
Leu-Phe-Ile-Cys(11 sugar)-Trp-Leu-Lys-Asn-
Gly-Gly-Pro-Ser-Lys(capric acid)-OH   [Chemical Formula 10]

Example 6: Preparation of AGM-212(E17C-11 Sugar & N28C-11 Sugar)

6-1. Chemical Formula 11

Chemical Formula 11 was prepared by the same method as in the preparation procedure of Example 1 while Fmoc-Asn(tBu)-OH, the 28th amino acid, was replaced with Fmoc-Cys(trt)-OH.

His-Gly-Glu-Gly-Thr-Phe-Thr-Ser-Asp-Leu-Ser-Lyc-
Gln-Met-Glu-Glu-Cys-Ala-Val-Arg-Leu-Phe-Ile-
Glu-Trp-Leu-Lys-Cys-Gly-Gly-Pro-Ser-Lys(ca-
pric acid)-OH   [Chemical Formula 11]

6-2. Chemical Formula 12

Bromoacetyl glycan (11 sugar) having a structure of undeca-saccharide, NaOH, and a phosphate buffer were added to Chemical Formula 11, thereby preparing Chemical Formula 12.

His-Gly-Glu-Gly-Thr-Phe-Thr-Ser-Asp-Leu-Ser-Lyc-
Gln-Met-Glu-Glu-Cys(11 sugar)-Ala-Val-Arg-
Leu-Phe-Ile-Glu-Trp-Leu-Lys-Cys(11 sugar)-
Gly-Gly-Pro-Ser-Lys(capric acid)-OH   [Chemical Formula 12]

Experimental Example 1: Investigation on GLP-1 Receptor Binding Affinity of Analogs To investigate the binding affinity of analogs prepared in Examples 1 to 6 for GLP-1 receptor, the luciferase assay system was used. The Luciferase assay system is a method that can investigating the activity level of a receptor by measuring the binding affinity of a ligand for a specific receptor of cells.

Specifically, the fibroblast cell line CV-1 ($1 \times 10^4$ cells/ml, Korea Cell Line Bank) was cultured on a 96-well white cell culture plate for 24 hours, and then human GLP-1R (pcDNA3.1_hGLP-1R) and cAMP response element (CRE, pcDNA3.1_hCRE) were added to perform transfection. After 24 hours, the medium was exchanged with a serum-free medium, followed by culture for 16 hours, and then each analog was treated for 6 hours. The expression level of luciferase, a reporter gene, by activated GLP-1R, was quantified by a luminometer, and the results are shown in Table 2.

TABLE 2

| Listing | $EC_{50}$ (nM) | Emax (fold induction over basal) |
| --- | --- | --- |
| Ex4 | 12 ± 0.12 | 10.6 ± 1.5 |
| AGM-212 | 11 ± 0.21 | 10.4 ± 1.4 |
| AGM-212(E17C-11 sugar) | 18.4 ± 0.4 | 10.1 ± 1.2 |
| AGM-212(N28C-11 sugar) | 35.6 ± 0.8 | 10.2 ± 1.3 |
| AGM-212(N28-11 sugar) | 58.5 ± 0.7 | 10.3 ± 1.4 |
| AGM-212(E24C-11 sugar) | 73.6 ± 0.4 | 10.1 ± 1.4 |
| AGM-212(E17C-11 sugar & E24C-11 sugar) | 80 ± 0.4 | 9.7 ± 1.2 |
| AGM-212(E17C-11 sugar & N28C-11 sugar) | 40 ± 0.5 | 9.8 ± 1.3 |

As can be confirmed in Table 2, AGM-212 showed the equivalent activity for GLP-1R to Ex4, and AGM-212 analogs with the undeca-saccharide linked thereto showed slightly reduced activity than Ex4 and AGM-212. It could be seen that each analog had reduced activity due to glycosylation but still had a nM level of binding affinity.

Experimental Example 2: Investigation on Insulin Secretion Ability of Analogs To investigate the insulin secretion ability of the analogs prepared in Examples 1 to 6, the glucose-dependent insulin secretion ability of the analogs from rat islets was investigated.

Figure 2:
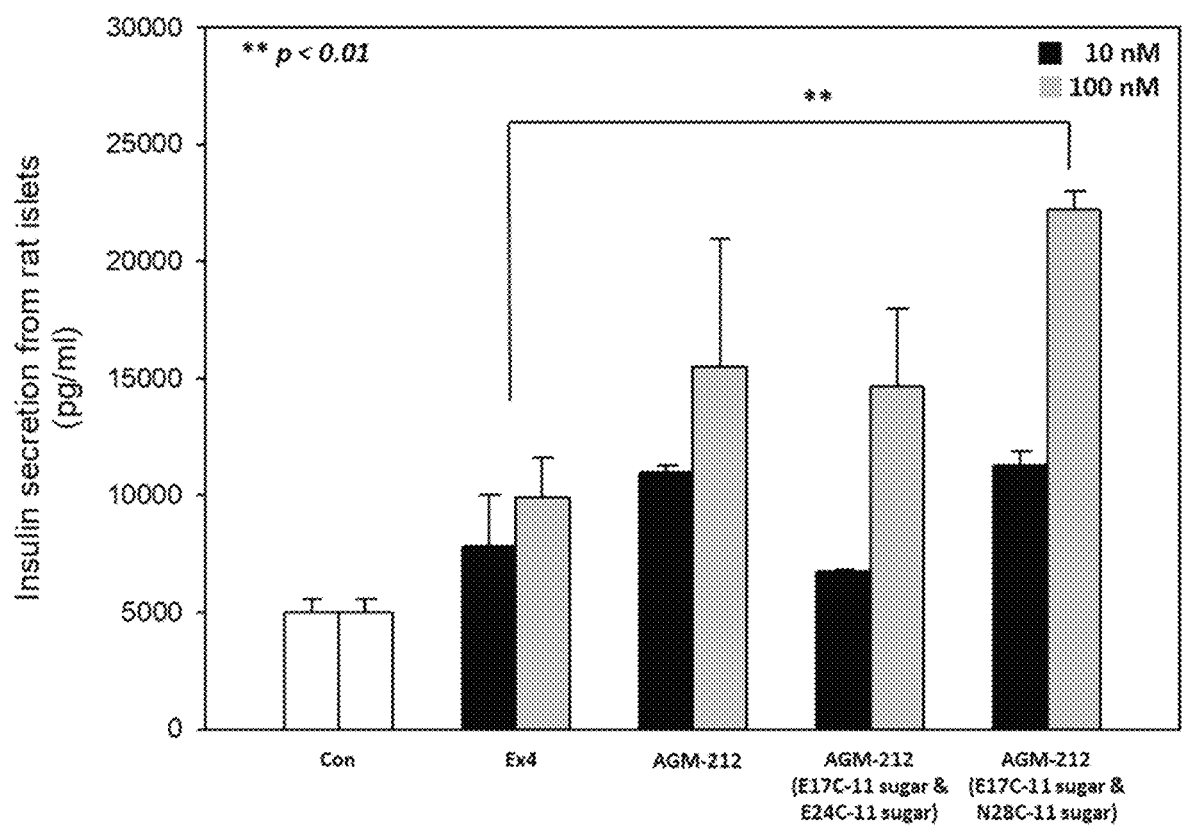
FIG. 2 shows the results of analyzing insulin secretion ability of glycosylated AGM-212 analogs (Examples 5 and 6) from rat islets through rat insulin ELISA according to an exemplary embodiment of the present disclosure.

Specifically, the pancreas of 8-week-old SD rats (Damul Science) was extracted, and islets were isolated. The isolated islets were treated with each analog in the 28 mM glucose at different concentrations (10 nM and 100 nM), and then the amount of insulin secreted was measured using the rat insulin ELISA kit, and the results are shown in FIGS. 1 and 2 and Tables 3 and 4.

TABLE 3

| | Insulin secretion from rat islets pg/ml) | |
| --- | --- | --- |
| Listing | 10 nM | 100 nM |
| Control | 4018.30 ± 536.4 | 4018.30 ± 536.4 |
| Ex4 | 5379.62 ± 1120 | 6038.49 ± 656.60 |
| AGM-212 | 5740.38 ± 111.7 | 6725.28 ± 988.68 |
| AGM-212(E17C-11 sugar) | 7895.09 ± 2457.36 | 9523.02 ± 2852.08 |

TABLE 3-continued

| Listing | Insulin secretion from rat islets pg/ml | |
|---|---|---|
| | 10 nM | 100 nM |
| AGM-212(N28C-11 sugar) | 5879.25 ± 2162.26 | 8168.68 ± 2623.02 |
| AGM-212(N28-11 sugar) | 5676.60 ± 1180.76 | 8128.68 ± 732.45 |

TABLE 4

| Listing | Insulin secretion from rat islets (pg/ml) | |
|---|---|---|
| | 10 nM | 100 nM |
| Control | 5018.30 ± 536.4 | 5020.30 ± 536.4 |
| Ex4 | 7803.40 ± 2216.2 | 9928.68 ± 1638.11 |
| AGM-212 | 10978.11 ± 268.68 | 15476.60 ± 5468.30 |
| AGM-212(E17C-11 sugar & E24C-11 sugar) | 6763.40 ± 32.83 | 14650.94 ± 3305.28 |
| AGM-212(E17C-11 sugar &N28C-11 sugar) | 11250.94 ± 624.53 | 22183.40 ± 830.19 |

As can be confirmed in FIGS. 1 and 2 and Tables 3 and 4, all the analogs with the undeca-saccharide linked thereto increased the insulin secretion in a dose-dependent manner and showed enhanced insulin secretion ability compared with Ex4 and AGM-212.

Experimental Example 3: Investigation on Sugar Load Effect of Analogs

To investigate the sugar load effect of analogs prepared in Examples 1 to 4, C57BKS/J dbdb mice (5-7 weeks old, Central Experimental Animal), Type 2 diabetes mouse models, were fasted for 16 hours, and each analog was subcutaneously administered at 10 nmole/kg, and after 30 minutes, glucose (1.5 g/kg) was administered intraperitoneally. The blood glucose was measured for 120 minutes by a blood glucose meter (accu-check, Roche, Germany) for blood extracted from the tail vein of the mice at 0, 15, 30, 45, 60, 90, and 120 minutes. The results are shown in FIGS. 3A to 3B.

Figure 3A:
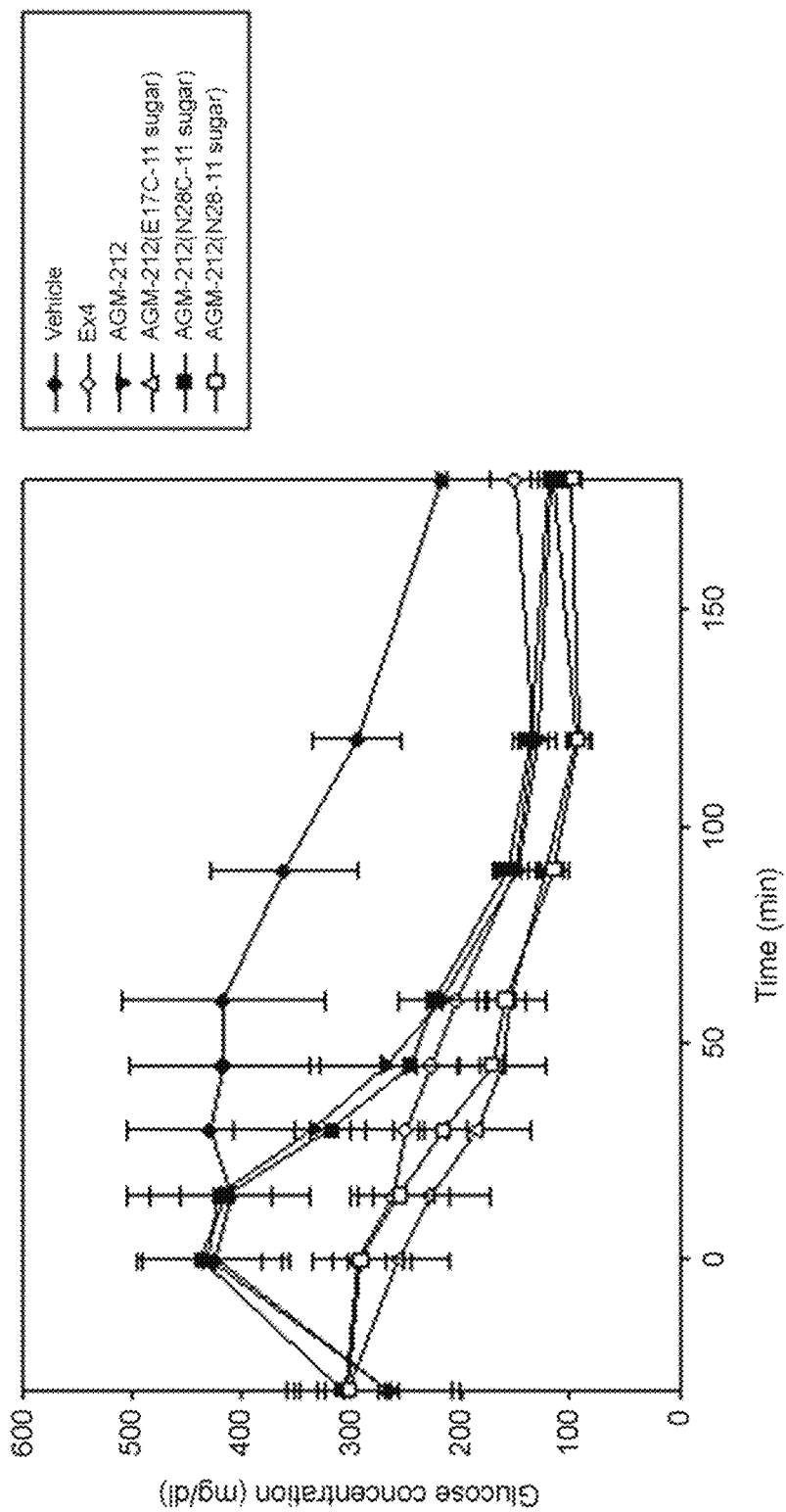
FIGS. 3A and 3B show the results of analyzing glucose load degrees through a glucose meter in Type 2 diabetes mouse animal models by subcutaneous administration of the glycosylated AGM-212 analogs according to an exemplary embodiment of the present disclosure.
Figure 3B:
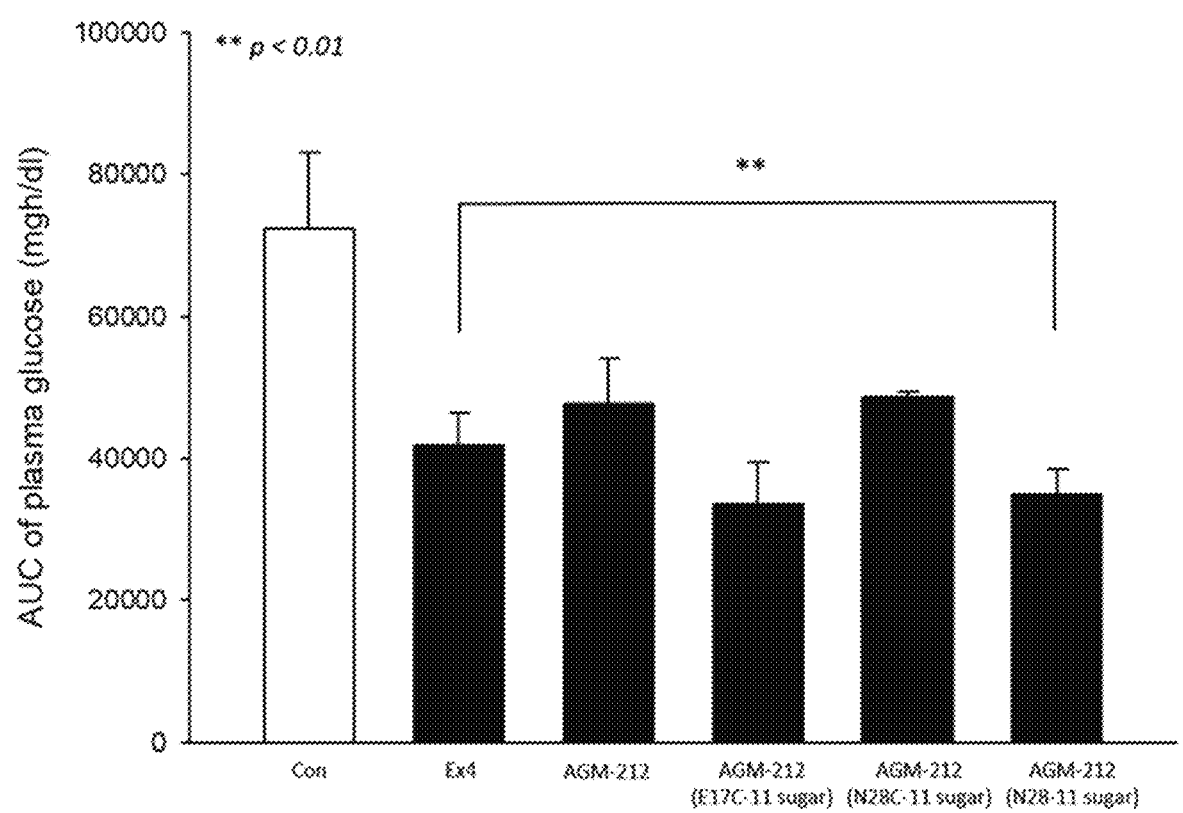

As can be confirmed in FIGS. 3A to 3B, all the AGM-212 analogs showed an equivalent sugar load effect to Ex4 and AGM-212 These results indicate that the glycosylated AGM-212 analogs have biological activity of Ex4.

Experimental Example 4: Test on Pharmacokinetics of Analogs

The analogs prepared in Examples 2 and 3 were tested for pharmacokinetics. After each analog at 50 nmole/kg was subcutaneously administered to wild-type C57BL/6J mice (male, 5-6 weeks old, n=5), blood was extracted 0, 0.5, 1, 2, 4, 8, 10, 12, 14, 24 hours, respectively. The plasma was separated from the extracted blood, and subjected to quantitative analysis using Exendin-4 EIA. As for the result analysis, the pharmacokinetics parameters were determined using the winnonlin program, and the results are shown in FIG. 4 and Table 5.

TABLE 5

| Parameter | Ex4 | AGM-212 | AGM-212 (N28C-11 sugar) | AGM-212 (N28-11 sugar) |
|---|---|---|---|---|
| t1/2 (h) | 0.56 ± 0.03 | 3.68 ± 0.35 | 2.3 ± 0.16 | 3.33 ± 0.74 |
| Tmax (h) | 0.5 | 4 | 4 | 5 ± 1 |
| Cmax (ng/mL) | 107.38 ± 12.48 | 750.67 ± 107.7 | 856.9 ± 103.4 | 762.9 ± 197.05 |
| AUC (ng h/mL) | 171.5 ± 7.15 | 6698.8 ± 621 | 4913.1 ± 380.5 | 5584.9 ± 968.5 |
| Vd (mL/kg) | 1004.9 ± 81.51 | 334.8 ± 38.35 | 416.7 ± 62.5 | 256.9 ± 37.8 |
| Cl (mL/h/kg) | 1236.9 ± 52.4 | 63.36 ± 5.93 | 123.3 ± 10.3 | 57.7 ± 8.98 |

Figure 4:
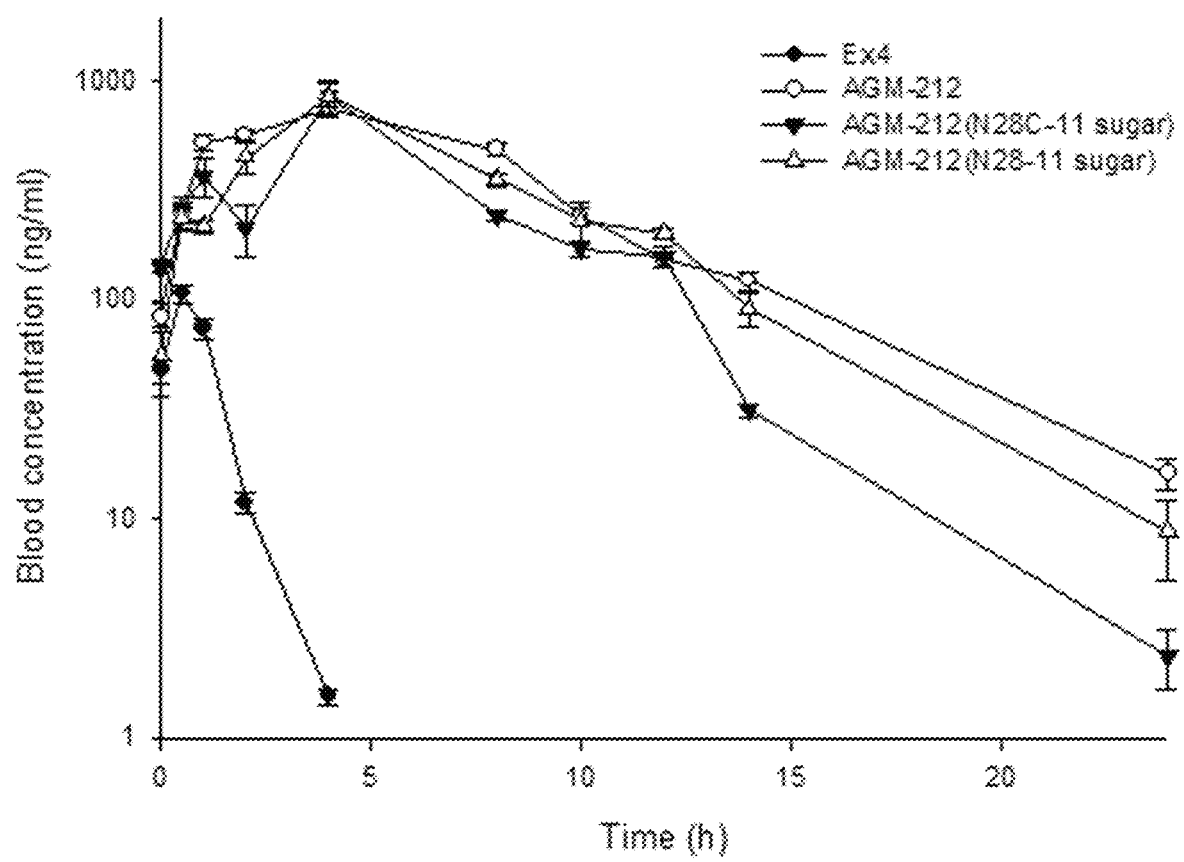
FIG. 4 shows the results of analyzing the pharmacokinetics evaluation test in wild-type mouse animal models by subcutaneous administration of the glycosylated AGM-212 analogs according to an exemplary embodiment of the present disclosure.

As shown in FIG. 4 and Table 5, AGM-212 (N28-11 sugar) showed a similar half-life to AGM-212, and the half-life of AGM-212 (N28C-11 sugar) was observed to be improved compared with Ex4 but showed a slightly reduced level compared with AGM-212 (N28-11 sugar). The results indicate that glycosylation does not influence the in-vivo half-time.

Experimental Example 5: Test on Immunogenicity of Analogs

For an immunogenicity test on glycosylated AGM-212 analogs, wild-type C57BL/6J mice (male, 6 weeks old) were subcutaneously administered Ex4 and AGM-212 (N28C-11 sugar) at 1 mg/kg together with Freund's complete adjuvant (sigma) once a week for a total of three times. Blood was extracted, and the produced antibodies were quantitatively analyzed using the antidrug antibody assay kit, and the results are shown in FIG. 5.

Figure 5:
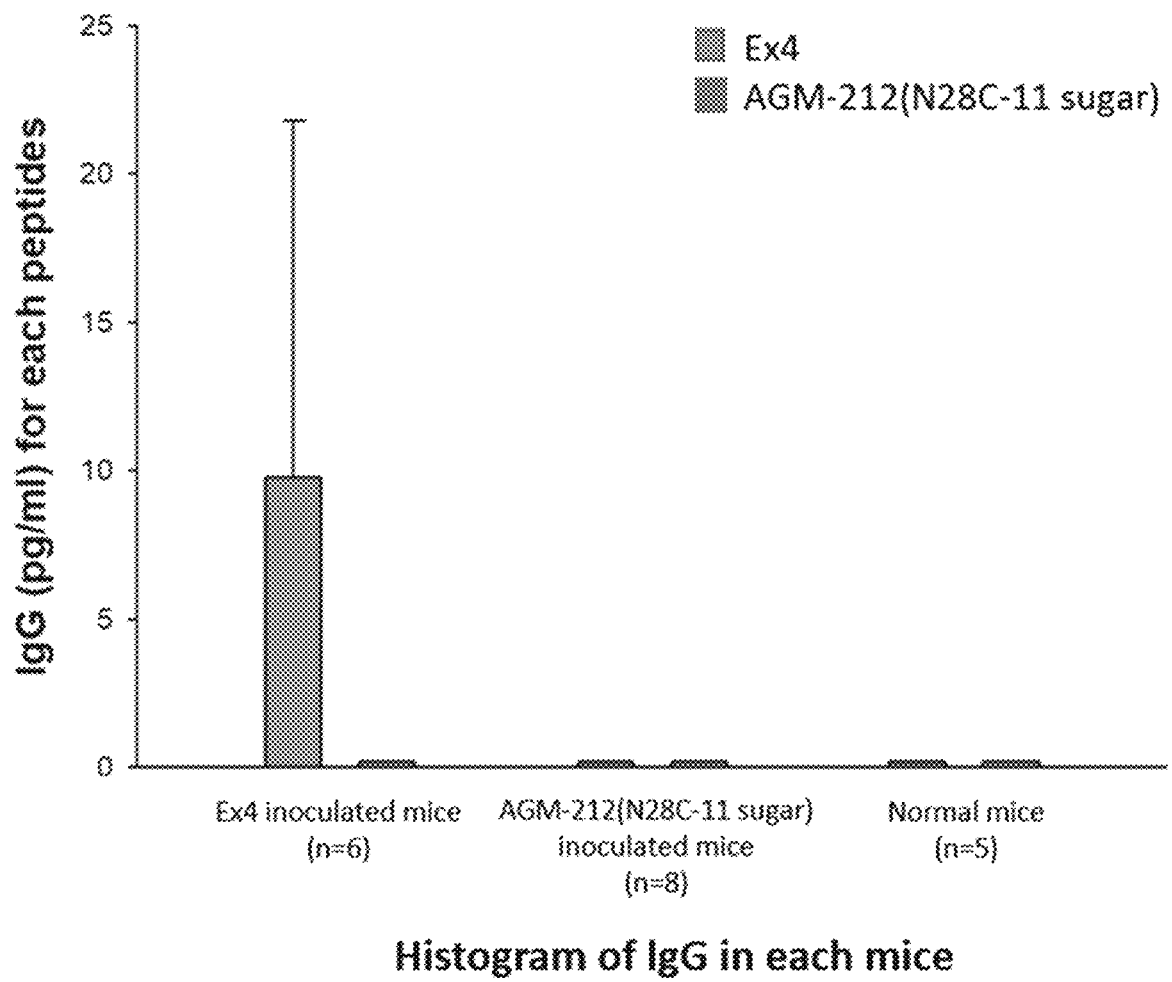
FIG. 5 shows the test results of immunogenicity of glycosylated AGM-212 analogs according to an exemplary embodiment of the present disclosure.

As can be confirmed in FIG. 5, the IgG antibody to Ex4 was formed at approximately 10 pg/ml in the group administered Ex4, but no antibody was detected in the group administered the glycosylated AGM-212 analogs. These results indicate that the glycosylated AGM-212 analogs showed improved immunogenicity thereof due to glycosylation.

Experimental Example 6: Test on Solubility of Analogs

Glycosylated analogs have increased solubility through the linkage of a sugar, and thus the solubility of the glycosylated AGM 212 analogs was tested. The solubility of AGM-212(N28C-11 sugar) and AGM-212(E17C-11 sugar & N28C-11 sugar) at 10 mg/ml in $H_2O$ and phosphate buffered saline (PBS) was obtained by using HPLC, and the results are shown in Table 6.

TABLE 6

| Solvent | Name | Solubility |
| --- | --- | --- |
| $H_2O$ | Ex4 | >10 mg/ml |
|  | AGM-212 | <2.5 mg/ml |
|  | AGM-212(N28C-11 sugar) | <6.1 mg/ml |
|  | AGM-212(E17C-11 sugar & N28C-11 sugar) | <8.3 mg/ml |
| PBS | Ex4 | >10 mg/ml |
|  | AGM-212 | <5.4 mg/ml |
|  | AGM-212(N28C-11 sugar) | <7.8 mg/ml |
|  | AGM-212(E17C-11 sugar & N28C-11 sugar) | <9.5 mg/ml |

As can be confirmed in Table 6, Ex4 had a solubility of 10 mg/ml in all the solvents, but AGM-212 had a slightly reduced solubility in $H_2O$ and showed approximately 0.5-fold solubility in PBS compared with Ex4. The glycosylated analogs showed an improved solubility compared with AGM-212 in all the solvents, and when comparing AGM-212 and the analogs with one and two 11 sugar linked thereto, a more increased solubility was found due to an increase in the number of sugars linked.

II. Exenatide Dimer Analogs

Example 1: Preparation of AGM-212-1

1-1. Chemical Formula 1

Fmoc-Lys(dde)-OH and DMF were added to trityl resin to prepare Fmoc-Lys(dde) trityl resin. DMF containing 20% piperidine, Fmoc-Ser(tBu)-OH, and hydroxyl-benzo triazole (HOBt) were added to the␣Fmoc-Lys(dde) trityl resin to prepare Fmoc-Ser(tBu)-Lys(dde) trityl resin. By the same preparation method as above, Fmoc-Pro-OH, Fmoc-Gly-OH, Fmoc-Gly-OH, Fmoc-Asn(trt)-OH, Fmoc-Lys(boc)-OH, Fmoc-Leu-OH, Fmoc-Trp(Boc)-OH, Fmoc-Cys(trt)-OH, Fmoc-Ile-OH, Fmoc-Phe-OH, Fmoc-Leu-OH, Fmoc-Arg(pbf)-OH, Fmoc-Val-OH, Fmoc-Ala-OH, Fmoc-Cys(Acm)-OH, Fmoc-Glu(tBu)-OH, Fmoc-Glu(tBu)-OH, Fmoc-Met-OH, Fmoc-Gln(trt)-OH, Fmoc-Lys(boc)-OH, Fmoc-Ser(tBu)-OH, Fmoc-Le)-OH, Fmoc-Asp(tBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(tBu)-OH, and Fmoc-Gly-OH, Fmoc-His(trt)-OH were sequentially added to the Fmoc-Ser(tBu)-Lys(dde) trityl resin to prepare Chemical Formula 1 below.

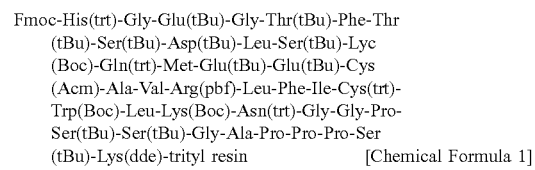
[Chemical Formula 1]

1-2. Chemical Formula 2

DMF containing 2% $NH_2NH_2 \cdot H_2O$ was added to Chemical Formula 1, followed by removal of dde, thereby preparing Chemical Formula 2.

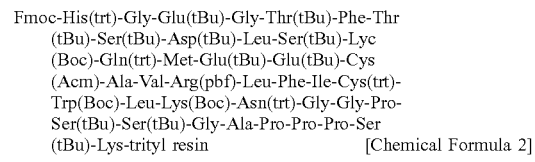
[Chemical Formula 2]

1-3. Chemical Formula 3

Capric acid and DMF containing HOBt and DIC were added to Chemical Formula 2 to prepare Chemical Formula 3.

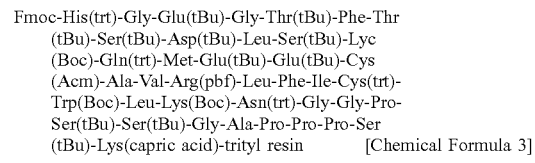
[Chemical Formula 3]

1-4. Chemical Formula 4

The protective group of Chemical Formula 3 was cleaved, followed by purification, thereby preparing Chemical Formula 4.

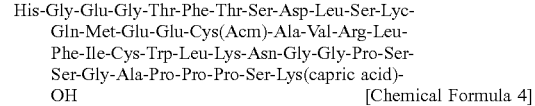
[Chemical Formula 4]

1-5. Chemical Formula 5

Bromoacetyl glycan (11 sugar) having a structure of undeca-saccharide, NaOH, and a phosphate buffer were added to Chemical Formula 4, thereby preparing Chemical Formula 5.

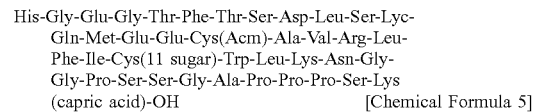
[Chemical Formula 5]

1-6. AGM-212-1

Silver acetate, iodine, and 50% acetic acid were added to Chemical Formula 5 to prepare AGM-212-1 of Table 7.

Example 2: Preparation of AGM-212-2

AGM-212-2 of Table 1 was prepared by the same method as in the preparation procedure of Example 1 while Fmoc-Asn(tBu)-OH, the 28th amino acid, was replaced with Fmoc-Cys(trt)-OH.

Example 3: Preparation of AGM-212-3

3-1. Chemical Formula 6

Fmoc-Lys-OH and DMF were added to trityl resin to prepare Fmoc-Lys trityl resin. Chemical Formula 6 was prepared by the same method as in the preparation procedure of Example 1 except that Fmoc-Cys(Acm)-OH at position 17 was substituted with Fmoc-Glu(tBu)-OH.

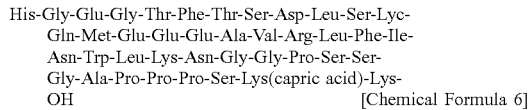

His-Gly-Glu-Gly-Thr-Phe-Thr-Ser-Asp-Leu-Ser-Lyc-Gln-Met-Glu-Glu-Glu-Ala-Val-Arg-Leu-Phe-Ile-Asn-Trp-Leu-Lys-Asn-Gly-Gly-Pro-Ser-Ser-Gly-Ala-Pro-Pro-Pro-Ser-Lys(capric acid)-Lys-OH [Chemical Formula 6]

3-2. Chemical Formula 7

To prepare glucagon, Fmoc-Thr(tBu)-OH and DMF were added to trityl resin to prepare Fmoc-Thr(tBu) trityl resin. DMF containing 20% piperidine, Fmoc-Asn(trt)-OH, and hydroxyl-benzo triazole (HOBt) were added to the Fmoc-Thr(tBu) trityl resin to prepare Fmoc-Asn(trt)-Thr(tBu) trityl resin. By the same preparation method as above, Fmoc-Met-OH, Fmoc-Leu-OH, Fmoc-Trp(Boc)-OH, Fmoc-Gln(trt)-OH, Fmoc-Val-OH, Fmoc-Phe-OH, Fmoc-Asp(tBu)-OH, Fmoc-Gln(trt)-OH, Fmoc-Ala-OH, Fmoc-Arg(pbf)-OH, Fmoc-Arg(pbf)-OH, Fmoc-Ser(tBu)-OH, Fmoc-Asp(tBu)-OH, Fmoc-Leu-OH, Fmoc-Tyr(tBu)-OH, Fmoc-Lys(trt)-OH, Fmoc-Ser(tBu)-OH, Fmoc-Tyr(tBu)-OH, Fmoc-Asp(tBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Gln(trt)-OH, Fmoc-Ser(tBu)-OH, and Fmoc-His(trt)-OH were sequentially added to the Fmoc-Asn(trt)-Thr(tBu) trityl resin to prepare Chemical Formula 7 below.

Fmoc-His(trt)-Ser(tBu)-Gln(trt)-Gly-Thr(tBu)-Phe-Thr(tBu)-Ser(tBu)-Asp(tBu)-Tyr(tBu)-Ser(tBu)-Lys(trt)-Tyr(tBu)-Leu-Asp(tBu)-Ser(tBu)-Arg(pbf)-Arg(pbf)-Ala-Gln(trt)-Asp(tBu)-Phe-Val-Gln(trt)-Trp(Boc)-Leu-Met-Asn(trt)-Thr(tBu)-trityl resin [Chemical Formula 7]

3-3. Chemical Formula 8

The protective group of Chemical Formula 7 was cleaved, followed by purification, thereby preparing Chemical Formula 8.

His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH [Chemical Formula 8]

3-4. AGM-212-3

DMA containing 20% piperidine and hydroxyl-benzo triazole (HOBt) were added to Chemical Formula 6 and Chemical Formula 8 to prepare AGM-212-3 of Table 7 in which Thr at position 30 in Chemical Formula 8 was linked to a side chain of Lys at position 34 of Chemical Formula 8.

Example 4: Preparation of AGM-212-4

A product was prepared by substituting Asn at position 28 with 11NC-Asn-Fmoc in the sequence of Chemical Formula 6 in Example 3, and DMF containing 20% piperidine and hydroxyl-benzo triazole (HOBt) were added thereto, thereby preparing AGM-212-4 of Table 7 in which the substance of Chemical Formula 8 is linked to a side chain of Lys at position 34 in Chemical Formula 6.

Example 5: Preparation of AGM-212-5

AGM-212-5 of Table 7 was prepared by the same preparation method as in the preparation procedure of Example 4 while Ser at position 16 was substituted with 11NC-Asn-Fmoc in the sequence of Chemical Formula 6.

Example 6: Preparation of AGM-212-6

AGM-212-6 of Table 7 was prepared by the same preparation method as in the preparation procedure of Example 4 while Gln at position 24 was substituted with 11NC-Asn-Fmoc in the sequence of Chemical Formula 6.

Example 7: Preparation of AGM-212-7

7-1. Chemical Formula 9

Ser at position 16 was substituted with Cys (Acm) and glutamine at position 24 was substituted with Cys in the preparation procedure of Example 5, thereby preparing Chemical Formula 10.

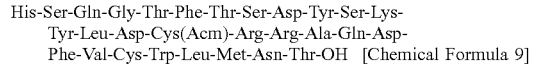

His-Ser-Gln-Gly-Thr-Phe-Thr-Ser-Asp-Tyr-Ser-Lys-Tyr-Leu-Asp-Cys(Acm)-Arg-Arg-Ala-Gln-Asp-Phe-Val-Cys-Trp-Leu-Met-Asn-Thr-OH [Chemical Formula 9]

7-1. Chemical Formula 10

Bromoacetyl glycan (11 sugar) having a structure of undeca-saccharide, NaOH, and a phosphate buffer were added to Chemical Formula 9, thereby preparing Chemical Formula 10.

His-Ser-Gln-Gly-Thr-Phe-Thr-Ser-Asp-Tyr-Ser-Lys-Tyr-Leu-Asp-Cys(Acm)-Arg-Arg-Ala-Gln-Asp-Phe-Val-Cys(11 sugar)-Trp-Leu-Met-Asn-Thr-OH [Chemical Formula 10]

7-2. AGM-212-7

Silver acetate, iodine, and 50% acetic acid were added to Chemical Formula 5 and Chemical Formula 10 to prepare AGM-212-7 of Table 7.

Example 8: Preparation of AGM-212-8

8-1. Chemical Formula 11

Ser at position 16 was substituted with Cys and Gln at position 24 was substituted with Cys (Acm) in the preparation procedure of Example 5, thereby preparing Chemical Formula 11.

His-Ser-Gln-Gly-Thr-Phe-Thr-Ser-Asp-Tyr-Ser-Lys-Tyr-Leu-Asp-Cys-Arg-Arg-Ala-Gln-Asp-Phe-Val-Cys(Acm)-Trp-Leu-Met-Asn-Thr-OH [Chemical Formula 11]

8-2. Chemical Formula 12

Bromoacetyl glycan (11 sugar) having a structure of undeca-saccharide, NaOH, and a phosphate buffer were added to Chemical Formula 11, thereby preparing Chemical Formula 12.

His-Ser-Gln-Gly-Thr-Phe-Thr-Ser-Asp-Tyr-Ser-Lys-Tyr-Leu-Asp-Cys(11 sugar)-Arg-Arg-Ala-Gln-Asp-Phe-Val-Cys(Acm)-Trp-Leu-Met-Asn-Thr-OH [Chemical Formula 12]

8-3. AGM-212-8

Silver acetate, iodine, and 50% acetic acid were added to Chemical Formulas 6 and 12 to prepare AGM-212-8 of Table 7.

TABLE 7

| Name | SEQ ID NO: |
|---|---|
| Ex4 | HGEGTFTSDL SKQMEEEAVR LFIEWLKNGG PSSGAPPPS |
| Glucagon | HSQGTFTSDY SKYLDSRRAQ DFVQWLMNT |
| AGM-212 | HGEGTFTSDL SKQMEEEAVR LFIEWLKNGG PSK-capric acid |
| AGM-212-1 | AGM-212 (E17C & E24C-11 sugar)-S-S-AGM-212 (E17C & E24C-11 sugar) |
| AGM-212-2 | AGM-212 (E17C & N28C-11 sugar)-S-S-AGM-212 (E17C & N28C-11 sugar) |
| AGM-212-3 | AGM-212-Lys(s.c)-glucagon |
| AGM-212-4 | AGM-212(N28-11 sugar)-Lys(s.c)-glucagon |
| AGM-212-5 | AGM-212(N28-11 sugar)-Lys(s.c)-glucagon(S16N-11 sugar) |
| AGM-212-6 | AGM-212(N28-11 sugar)-Lys(s.c)-glucagon(Q24N-11 sugar) |
| AGM-212-7 | AGM-212(E17C & E24C-11 sugar)-S-S-glucagon(S16C-11 sugar & Q24C) |
| AGM-212-8 | AGM-212(E17C & E24C-11 sugar)-S-S-glucagon(S16C & Q24C-11 sugar) |

Experimental Example 1: Investigation on GLP-1 Receptor Binding Affinity of Analogs To investigate the binding affinity of analogs prepared in Examples 1 to 6 for GLP-1 receptor, the luciferase assay system was used. The Luciferase assay system is a method that can investigating the activity level of a receptor by measuring the binding affinity of a ligand for a specific receptor of cells.

Specifically, the fibroblast cell line CV-1 ($1\times10^4$ cells/ml, Korea Cell Line Bank) was cultured on a 96-well white cell culture plate for 24 hours, and then human GLP-1R (pcDNA3.1_hGLP-1R) and cAMP response element (CRE, pcDNA3.1_hCRE) were added to perform transfection. After 24 hours, the medium was exchanged with a serum-free medium, followed by culture for 16 hours, and then each analog was treated for 6 hours. The expression level of luciferase, a reporter gene, by activated GLP-1R, was quantified by a luminometer, and the results are shown in Table 8.

TABLE 8

| Name | $EC_{50}$ (nM) | $E_{max}$ (fold induction over basal) |
|---|---|---|
| Ex4 | 0.8 ± 0.12 | 10.6 ± 1.5 |
| AGM-212 | 0.91 ± 0.21 | 10.4 ± 1.4 |
| AGM-212-1 | 0.13 ± 0.4 | 10.1 ± 1.2 |
| AGM-212-2 | 0.11 ± 0.8 | 10.2 ± 1.3 |
| AGM-212-3 | 8 ± 0.7 | 10.1 ± 1.4 |
| AGM-212-4 | 32 ± 1.7 | 10.2 ± 1.2 |
| AGM-212-5 | 25 ± 1.2 | 10.4 ± 1.1 |
| AGM-212-6 | 34 ± 1.5 | 7.2 ± 1.3 |
| AGM-212-7 | 16 ± 1.5 | 10.2 ± 1.3 |
| AGM-212-8 | 25 ± 1.5 | 10.3 ± 1.5 |

As can be confirmed in Table 8, AGM-212-1 and AGM-212-2 showed an approximately at least 6-fold increase in EC50 level compared with Ex4. It can be seen from these results that glycosylated exenatide homologue analogs composed by a disulfide linkage have higher activity for GLP-1 receptor than existing Ex4 and AGM-212. AGM-212-3 was observed to have an approximately 10-fold decreased EC50 level, and AGM-212-4, AGM-212-5, and AGM-212-6 were observed to have approximately 4- to 5-fold decreased activity compared with AGM-212-3. It can be seen from these results that the linkage of glucagon and exenatide analogs via a disulfide linkage somewhat reduced the activity for GLP-1 receptor, and the glycosylation of glucagon in the heterogeneous analog structure reduced the activity of GLP-1 receptor. However, all the analogs showed high binding affinity (nM level) for GLP-1 receptor, indicating that the analogs have selective and specific functions of an agonist.

The results confirmed that AGM-212 showed the equivalent activity for GLP-1R to Ex4, and AGM-212 analogs with the undeca-saccharide linked thereto showed somewhat reduced activity than Ex4 and AGM-212. It can be seen that each analog had reduced activity due to 11 sugar, but still had a nM level of binding affinity.

Experimental Example 2: Investigation on Insulin Secretion Ability of Analogs To determine the insulin secretion ability of the analogs prepared in Examples 1 and 2, the glucose-dependent insulin secretion ability of the analogs from rat islets was investigated. The pancreas of 8-week-old SD rats (Damul Science) was extracted, and islets were isolated. The isolated islets were treated with each analog in the 28 mM glucose at different concentrations (10 nM and 100 nM), and then the amount of insulin secreted was measured using the rat insulin ELISA kit, and the results are shown in FIG. 6 and Table 9.

TABLE 9

| | Insulin secretion from rat islets (pg/ml) | |
|---|---|---|
| Listing | 10 nM | 100 nM |
| Control | 5018.30 ± 534.4 | 5020.30 ± 533.4 |
| Ex4 | 7803.40 ± 2216.2 | 9928.68 ± 1638.11 |
| AGM-212 | 10978.11 ± 268.7 | 15476.60 ± 5468.3 |
| AGM-212-1 | 14506.04 ± 3493.9 | 20080 ± 8384.9 |
| AGM-212-2 | 14446.79 ± 654.34 | 24954.72 ± 2741.89 |

Figure 6:
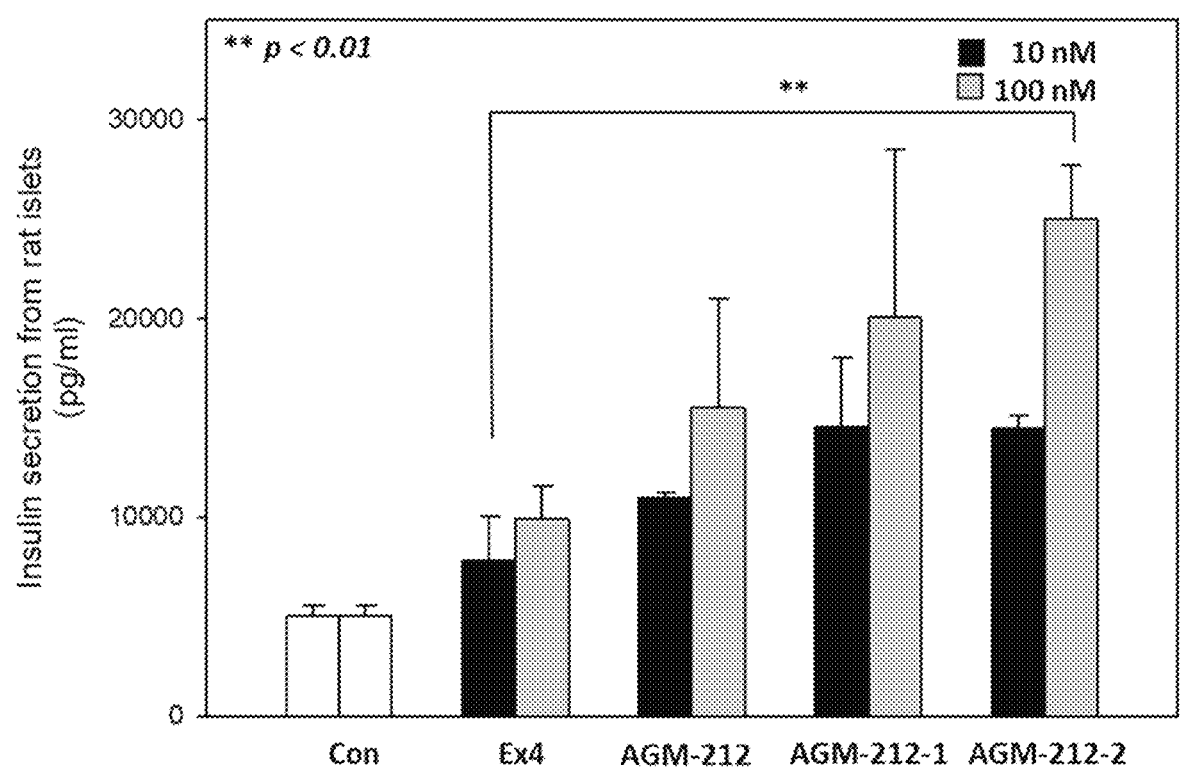
FIG. 6 shows the results of analyzing insulin secretion ability of analogs from rat islets through rat insulin ELISA according to an exemplary embodiment of the present disclosure.

As can be confirmed in FIG. 6 and Table 9, glycosylated exenatide homologous analogs showed insulin secretion ability increased in a dose-dependent manner compared with exenatide and AGM-212.

Experimental Example 3: Investigation on Anti-Diabetic Effect of Analogs

To investigate the anti-diabetic effect of analogs prepared in Examples 1 to 6, the blood glucose lowering effect was investigated in C57BKS/J dbdb mice (5-7 weeks old, Central Experimental Animal), Type 2 diabetes mouse models.

Specifically, each analog was subcutaneously administered at 20 nmole/kg, and after 0, 1, 2, 4, 6, 8, 12, 18, 24, 44, and 48 hours, the blood was extracted from the tail vein of the mice to measure the level of blood glucose. The results are shown in FIGS. 7A to 8B.

Figure 7A:
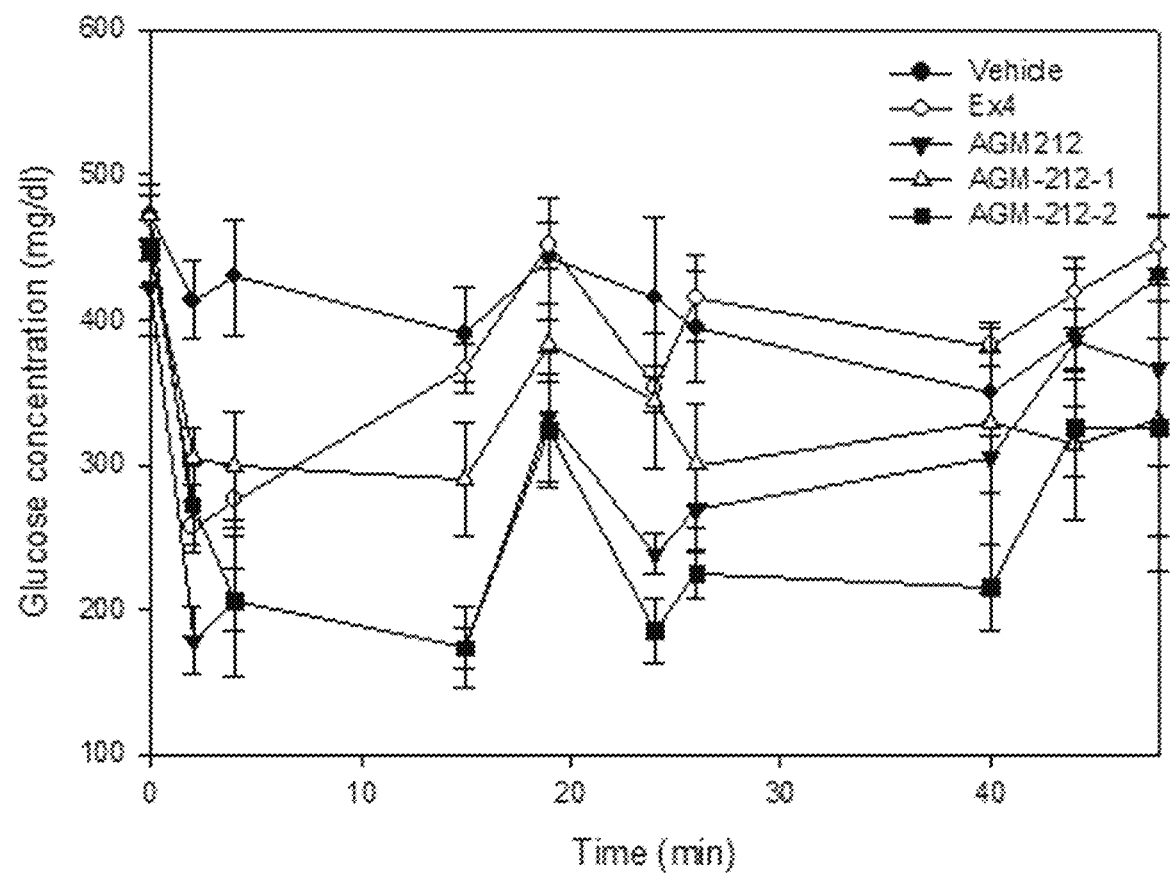
FIG. 7A shows the results of analyzing anti-diabetic effects in Type 2 diabetes disease mouse animal models through a glucose meter by subcutaneous administration of analogs including AGM-212-1 and AGM-212-2 according to an exemplary embodiment of the present disclosure.
Figure 7B:
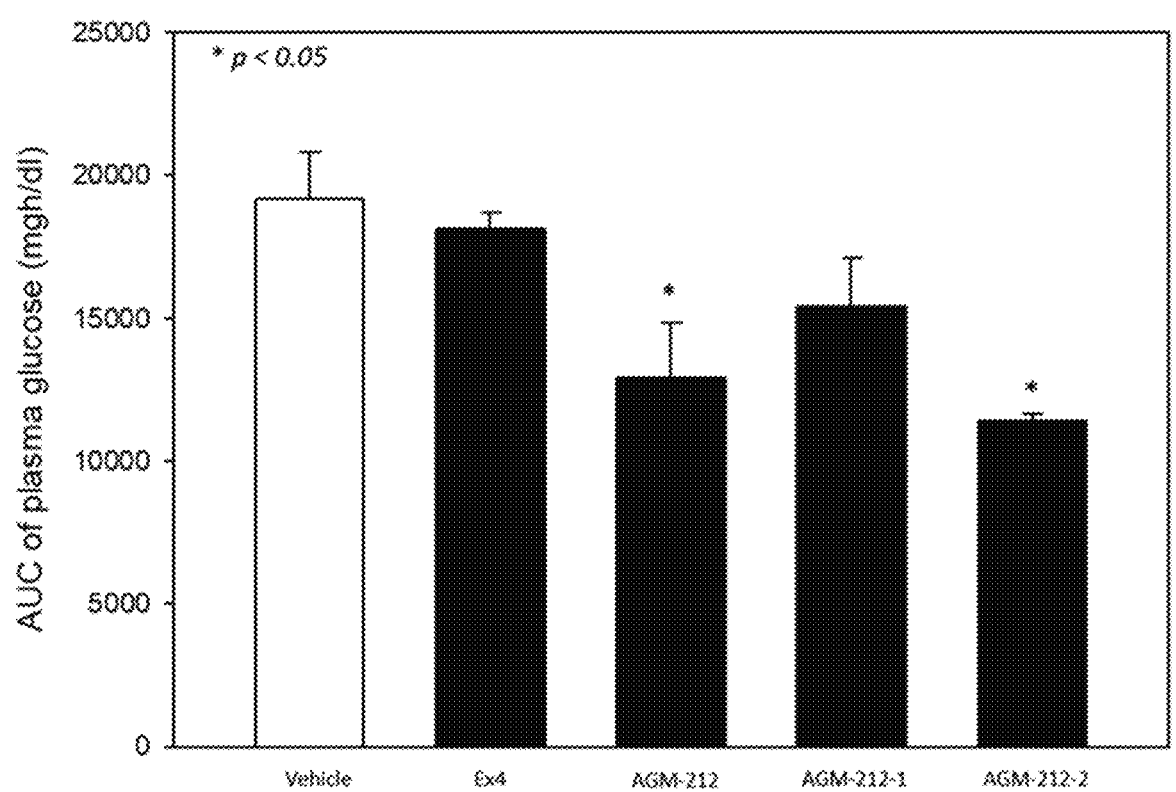
FIG. 7B shows the results of analyzing anti-diabetic effects in Type 2 diabetes disease mouse animal models through a glucose meter by subcutaneous administration of analogs including AGM-212-1 and AGM-212-2 according to an exemplary embodiment of the present disclosure.

As can be conformed from FIGS. 7A and 7B, AGM-212-2 showed an increased degree of blood glucose lowering compared with Ex4 and AGM-212. Though the comparison with the activity results of AGM-212-1, it can be seen that the glycosylation of Cys at position 24 in AGM-212-1 exhibited a reduced anti-diabetic effect.

Figure 8A:
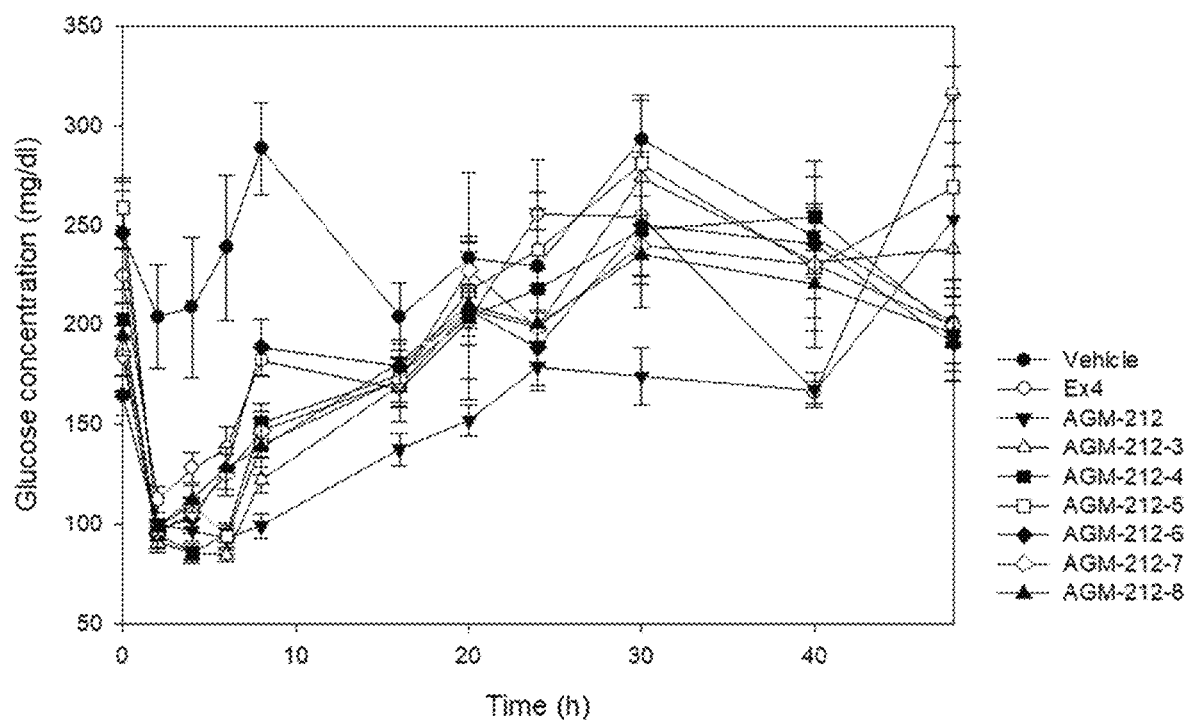
FIG. 8A shows the results of analyzing anti-diabetic effects in Type 2 diabetes disease mouse animal models through a glucose meter by subcutaneous administration of analogs including AGM-212-3, AGM-212-4, AGM-212-5, and AGM-212-6 according to an exemplary embodiment of the present disclosure.
Figure 8B:
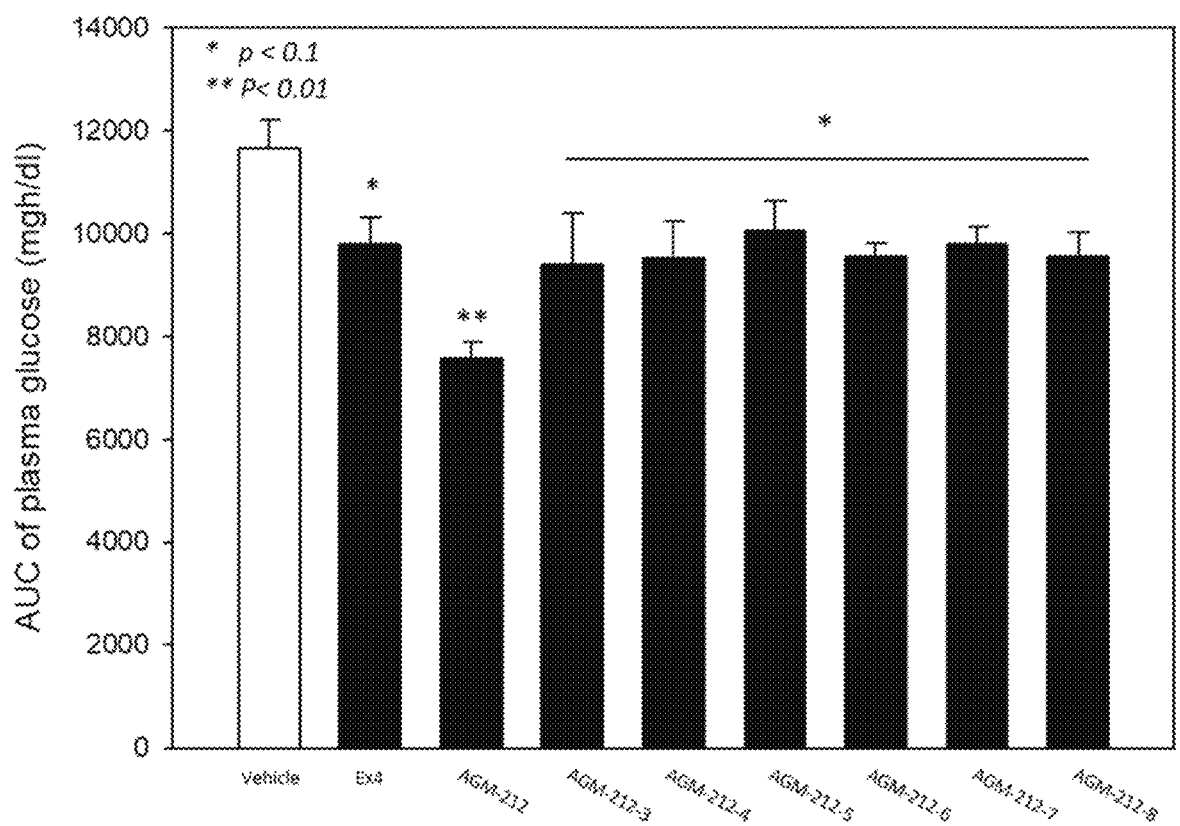
FIG. 8B shows the results of analyzing anti-diabetic effects in Type 2 diabetes disease mouse animal models through a glucose meter by subcutaneous administration of analogs including AGM-212-3, AGM-212-4, AGM-212-5, and AGM-212-6 according to an exemplary embodiment of the present disclosure.

As can be confirmed in FIGS. 8A and 8B, all of AGM-212-3, AGM-212-4, and AGM-212-5 showed a significant anti-diabetic effect, but a somewhat reduced effect compared with AGM-212. AGM-212-4, AGM-212-5, and AGM-212-6 had structures in which sugars were linked to constituent residues of glucagon in the sequence of AGM-212-3, but there was no significant activity difference resulting from each residue in terms of the anti-diabetic effect. AGM-212-7 and AGM-212-8 were configured by disulfide linkages of AGM-212 with glucagon moieties having different residues glycosylated, respectively, and showed similar anti-diabetic effects to Ex4.

Experimental Example 4: Test on Pharmacokinetics of Analogs

Figure 9A:
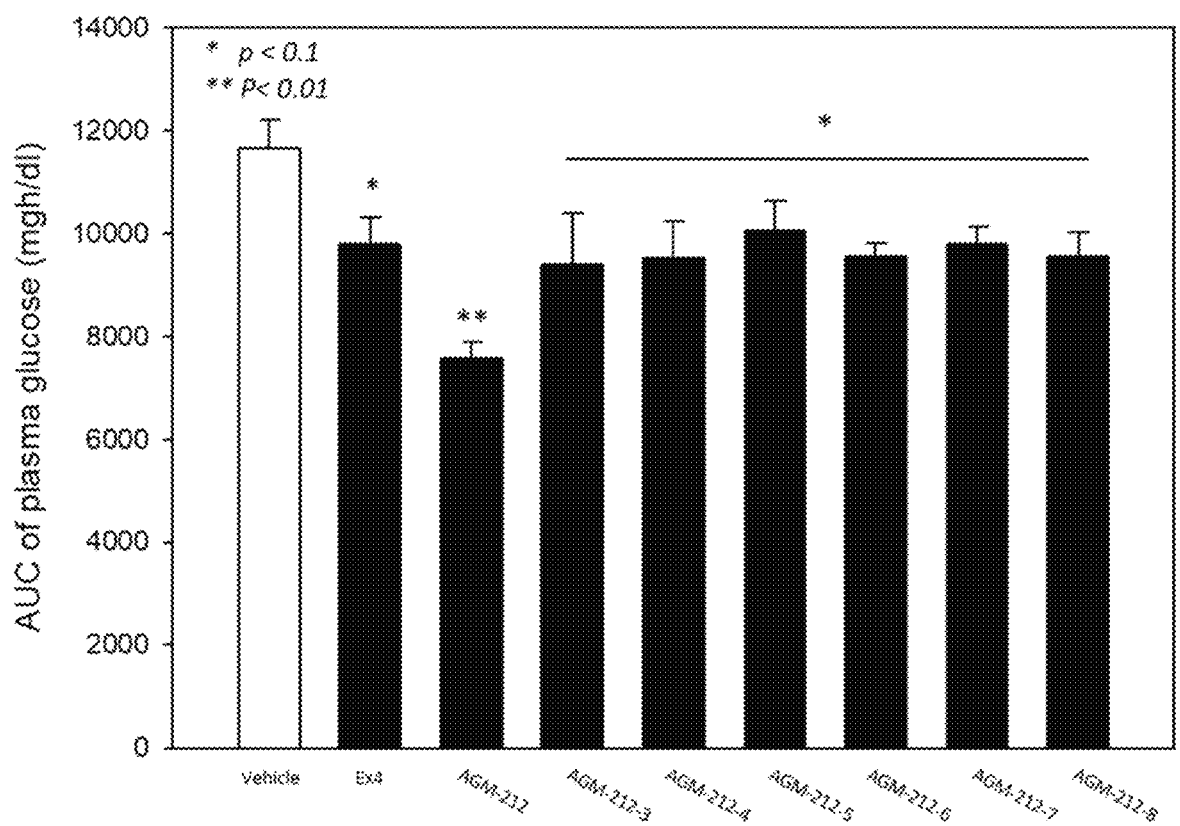
FIG. 9A shows the results of analyzing the pharmacokinetics evaluation test in wild-type mouse animal models by subcutaneous administration of analogs according to an exemplary embodiment of the present disclosure.
Figure 9B:
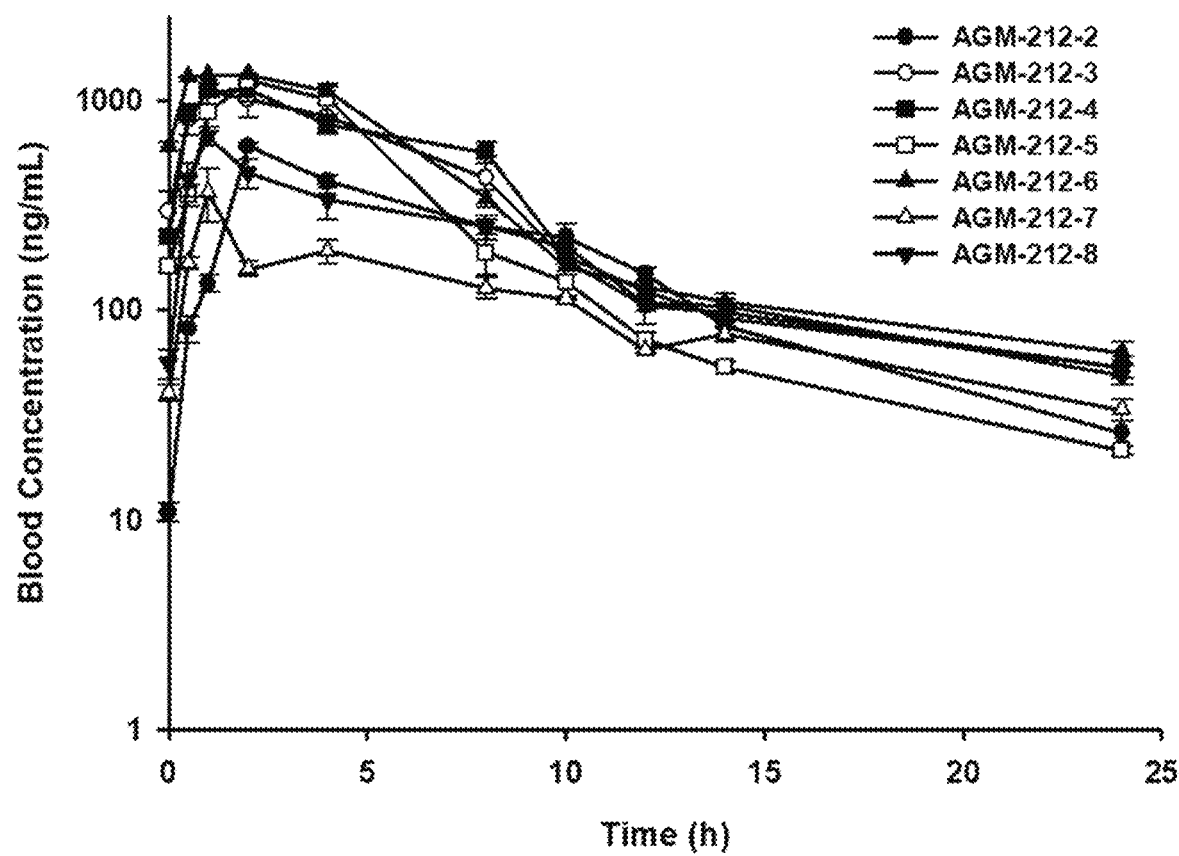
FIG. 9B shows the results of analyzing the pharmacokinetics evaluation test in wild-type mouse animal models by subcutaneous administration of analogs according to an exemplary embodiment of the present disclosure.

The analogs prepared in Examples 1 to 8 were tested for pharmacokinetics. After each analog at 50 nmole/kg was subcutaneously administered to wild-type C57BL/6J mice (male, 5-6 weeks old, n=5), blood was extracted 0, 0.5, 1, 2, 4, 8, 10, 12, 14, 24 hours, respectively. The plasma was separated from the extracted blood, and subjected to quantitative analysis using Exendin-4 EIA. As for the result analysis, the pharmacokinetics parameters were determined using the winnonlin program, and the results are shown in FIGS. 9A and 9B.

TABLE 10

| Parameter | Ex4 | AGM-212 | AGM-212-2 | AGM-212-3 | AGM-212-4 |
| --- | --- | --- | --- | --- | --- |
| t1/2 (h) | 0.56 ± 0.03 | 3.68 ± 0.35 | 4.85 ± 0.278 | 4.86 ± 0.3 | 4.77 ± 0.33 |
| Tmax (h) | 0.5 | 4 | 2 | 1 ± 0.4 | 1.5 ± 0.28 |
| Cmax (ng/mL) | 107.38 ± 12.48 | 750.67 ± 107.7 | 605.15 ± 19.03 | 1219.06 ± 66.12 | 1190.2 ± 84.8 |
| AUC (ng h/mL) | 171.5 ± 7.15 | 6698.8 ± 621 | 4414.9 ± 226.38 | 7647.23 ± 548.3 | 8365.12 ± 71.5 |
| Vd (ml/kg) | 1004.9 ± 81.51 | 334.8 ± 38.35 | 993 ± 54.15 | 440.3 ± 55.9 | 783.6 ± 93.4 |
| Cl (mL/h/kg) | 1236.9 ± 52.4 | 63.36 ± 5.93 | 133.9 ± 7.19 | 62.1 ± 4.22 | 55.5 ± 1.67 |

| Parameter | AGM-212-5 | AGM-212-6 | AGM-212-7 | AGM-212-8 |
| --- | --- | --- | --- | --- |
| t1/2 (h) | 3.72 ± 0.06 | 4.69 ± 0.18 | 5.82 ± 0.1 | 5.84 ± 0.23 |
| Tmax (h) | 2.5 ± 0.5 | 1.13 ± 0.32 | 1.75 ± 0.75 | 1 |
| Cmax (ng/mL) | 1250 ± 83.3 | 1333.3 | 715.6 ± 81.1 | 675.1 ± 65.4 |
| AUC (ng h/mL) | 7229.2 ± 741.3 | 9684.1 ± 294.1 | 4608.4 ± 383.02 | 4658.1 ± 130.77 |
| Vd (ml/kg) | 453.3 ± 54.5 | 403.5 ± 12.9 | 822.2 ± 61.7 | 805.5 ± 43.9 |
| Cl (mL/h/kg) | 84.2 ± 8.9 | 59.73 ± 2 | 97.8 ± 7.15 | 95.4 ± 2.01 |

As can be confirmed in FIGS. 9A and 9B and Table 10, all the analogs showed a significantly increased half-time compared with Ex4, and specifically, AGM-212-1, AGM-212-2, AGM-212-3, AGM-212-4, AGM-212-5, AGM-212-6, AGM-212-7, and AGM-212-8 showed an approximately 1- to 1.5-fold increased half-time level compared with AGM-212. These results indicate that the exenatide dimer analogs have significantly improved in vivo stability through a particular linkage, such as a disulfide linkage.

Experimental Example 5: Investigation on Body Weight and Dietary Control Ability of Analogs in Obesity Disease Animal Models The analogs prepared in Example 3 were tested and evaluated for body weight reduction and dietary control ability in obesity disease animal models. Obesity disease animal models were fabricated by inducing C57BL/6 mice to take in a high-fat diet containing 60% or more fat to have both obesity and hyperglycemia. AGM-212-3 and AGM-212-4 were subcutaneously administered to 16-week-old obesity disease mice at 50 nmole/kg once a day for 9 weeks. The results are shown in FIGS. 10A to 10C and Table 11.

TABLE 11

| Group | Body weight change (%) |
|---|---|
| Vehicle | 17.17 ± 0.56 |
| Ex4 | −2.63 ± 1.06 |
| AGM-212 | 11.71 ± 2.40 |
| Glucagon | −8.67 ± 1.76 |
| AGM-212 + glucagon | −12.36 ± 2.11 |
| AGM-212-3 | −21.95 ± 1.83 |
| AGM-212-4 | −20.04 ± 2.21 |

Figure 10A:
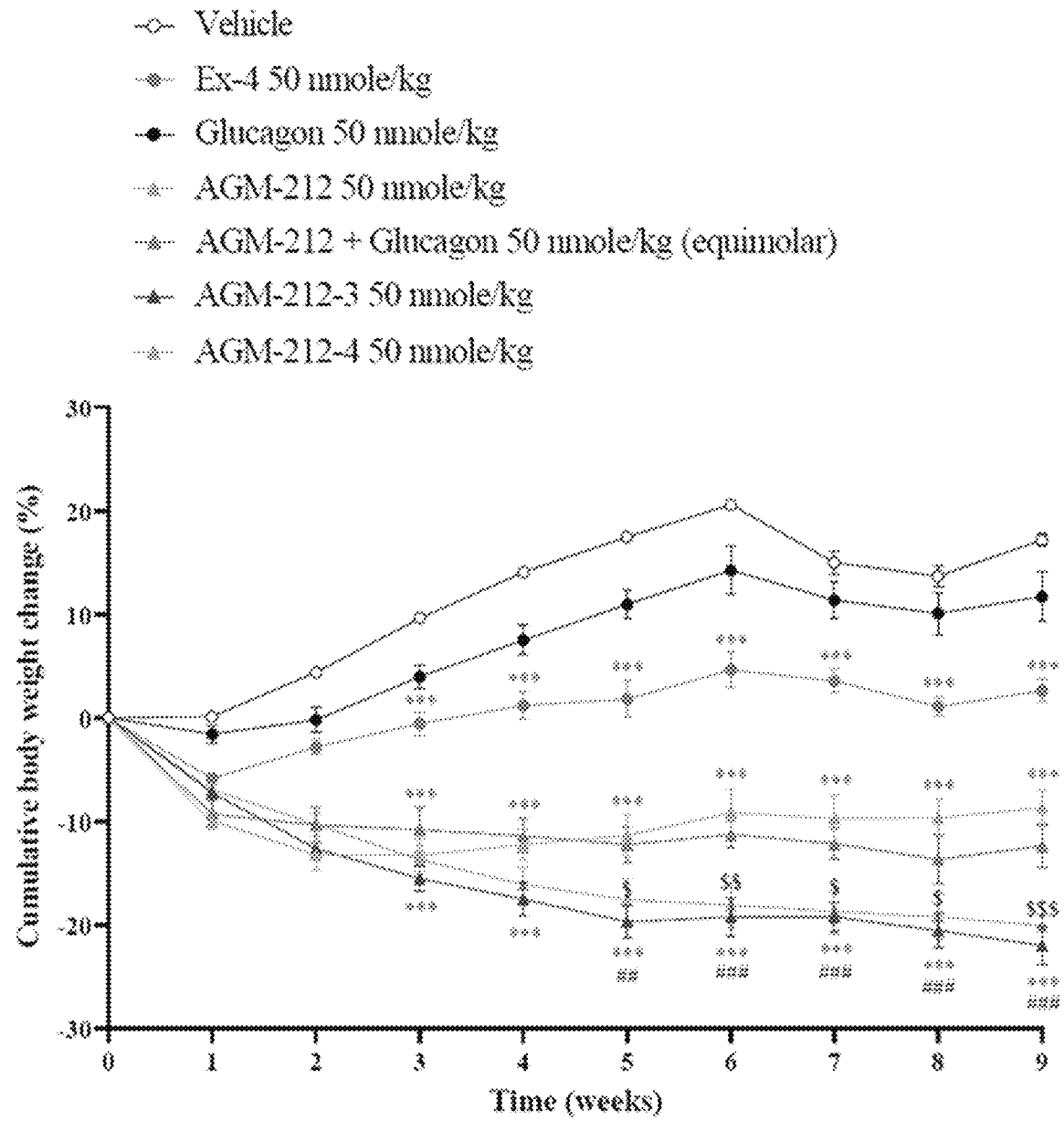
FIG. 10A shows the test results of dietary control ability of analogs according to an exemplary embodiment of the present disclosure.
Figure 10B:
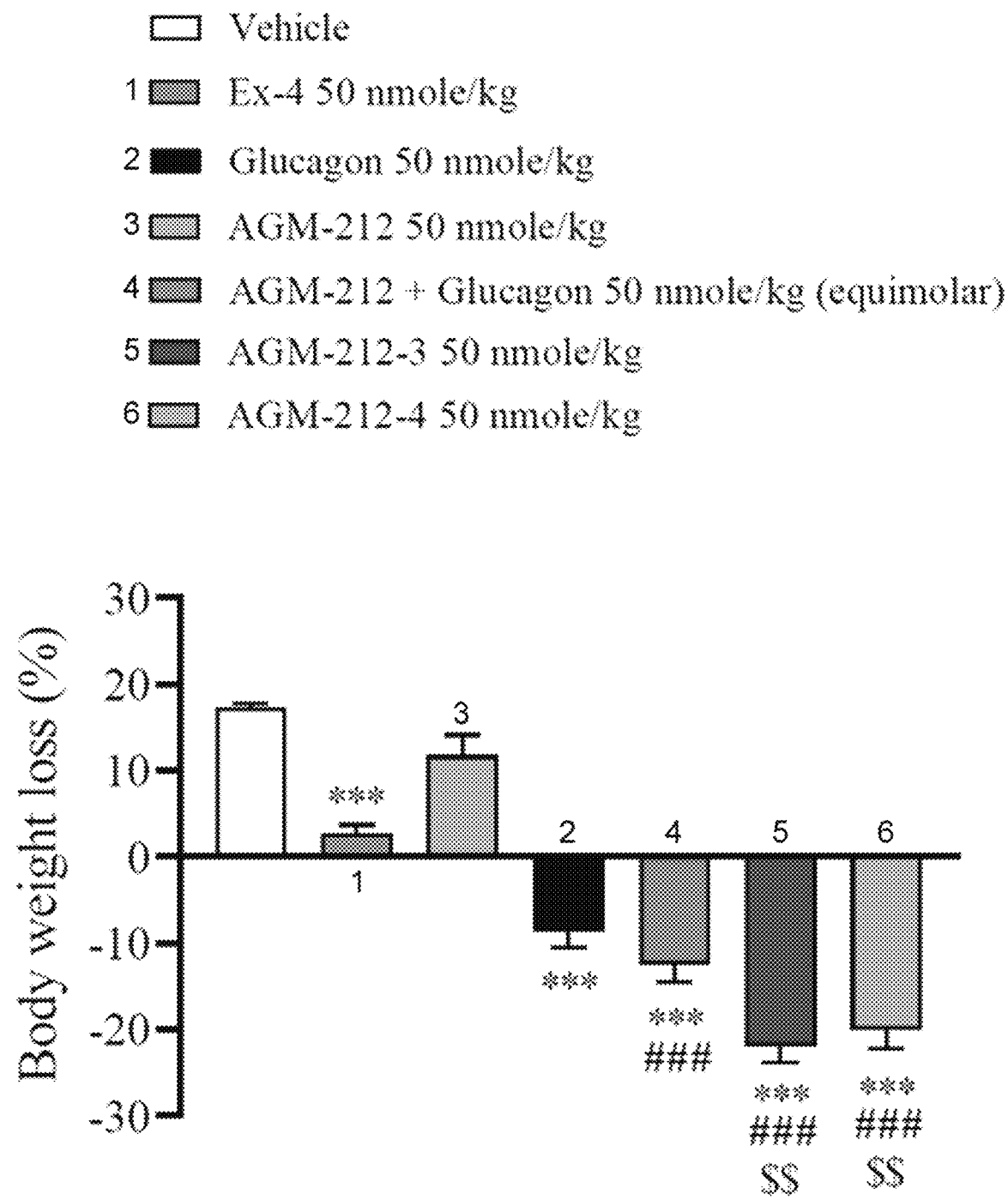
FIG. 10B shows the test results of dietary control ability of analogs according to an exemplary embodiment of the present disclosure.
Figure 10C:
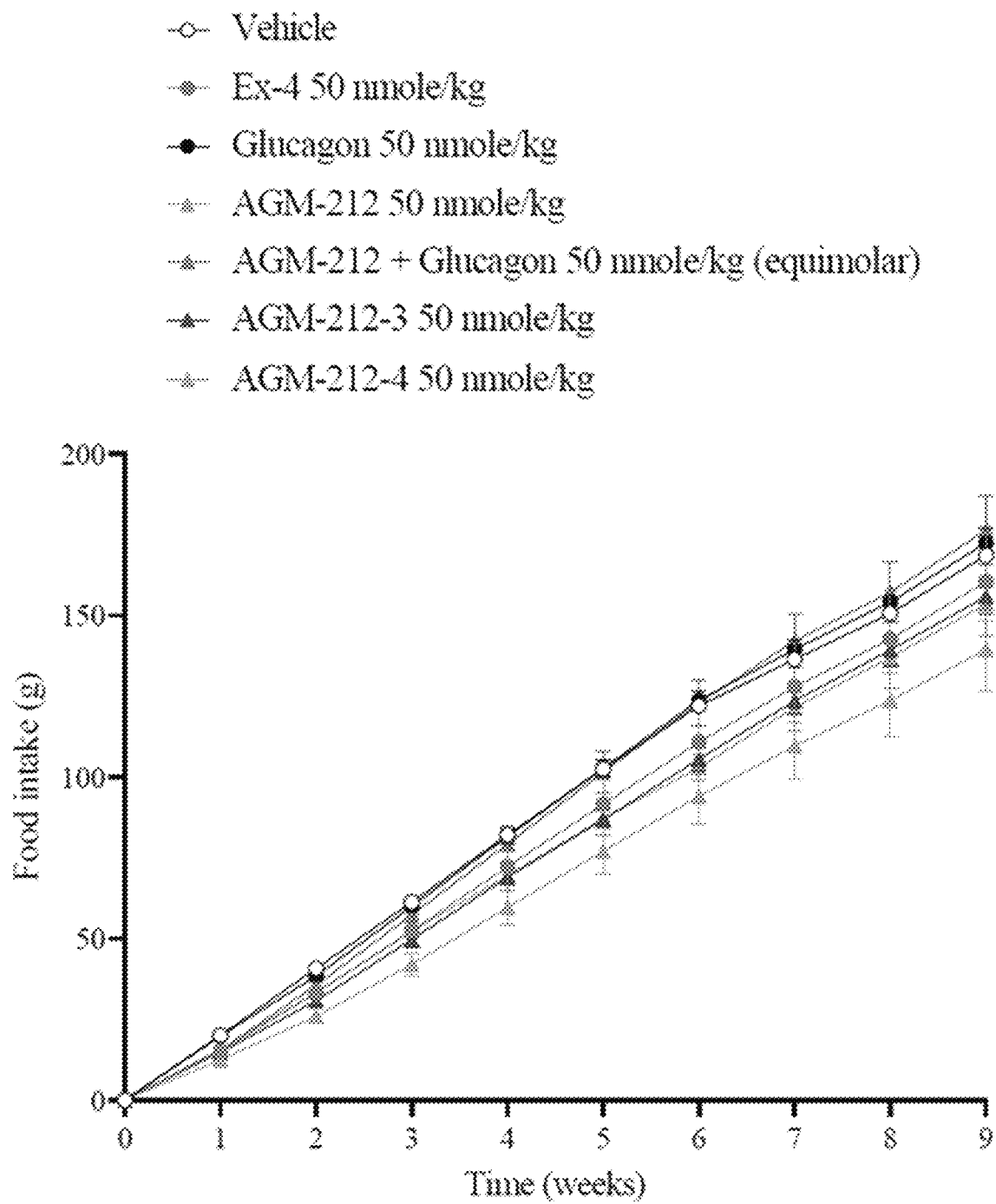
FIG. 10C shows the test results of dietary control ability of analogs according to an exemplary embodiment of the present disclosure.

As can be confirmed in FIGS. 10A to 10C and Table 11, the body weight of the group administered each analogue was significantly reduced from the 3rd week, and there was a significant difference compared with the group administered AGM-212 or co-administered AGM-212 and glucagon from the 5th week. At the 9th week when the experiment ended, the food intake of the groups administered AGM-212-3 and AGM-212-4 was also significantly reduced.

Figure 11A:
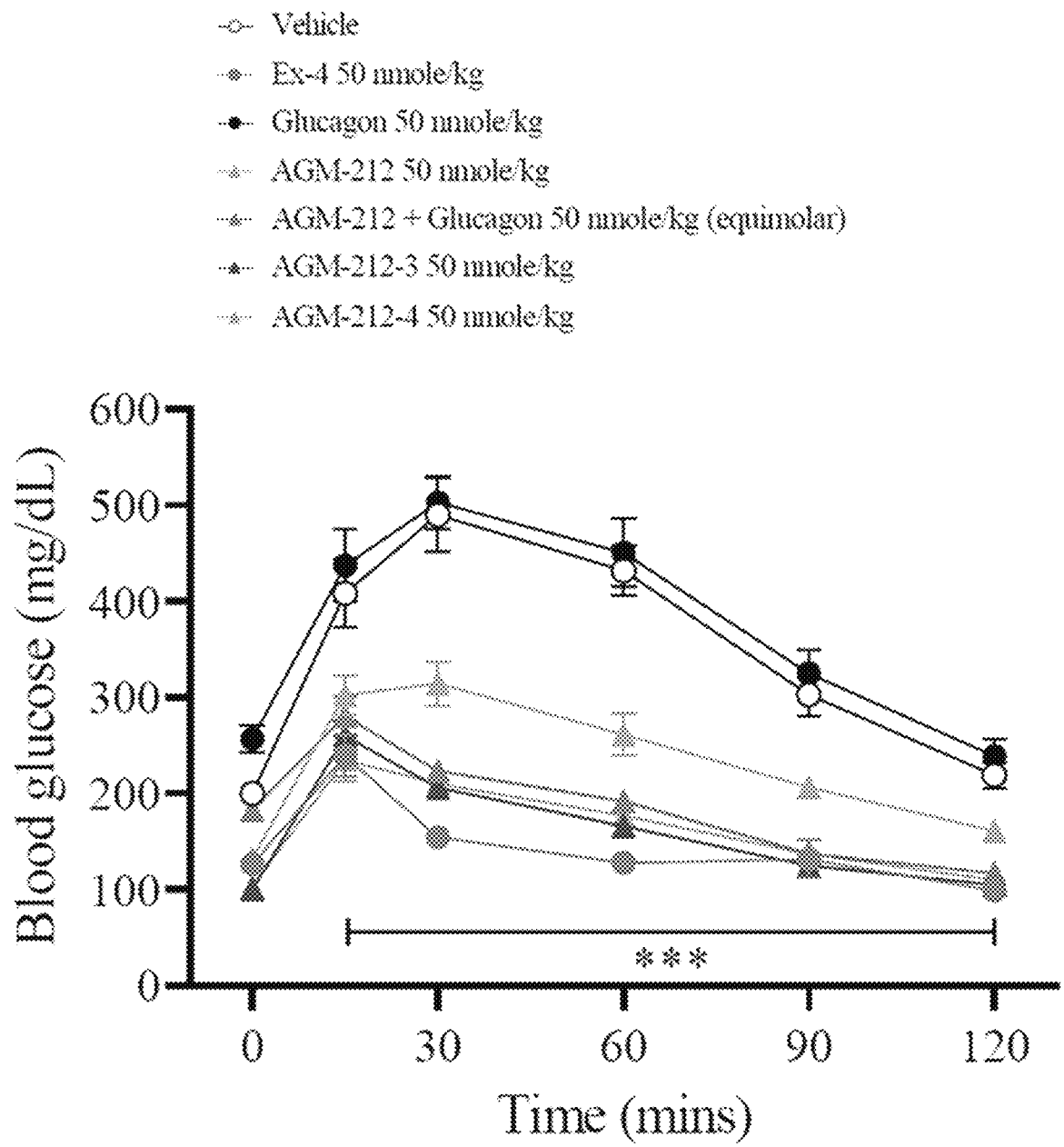
FIG. 11A shows the test results of glucose tolerance improvement of analogs according to an exemplary embodiment of the present disclosure.
Figure 11B:
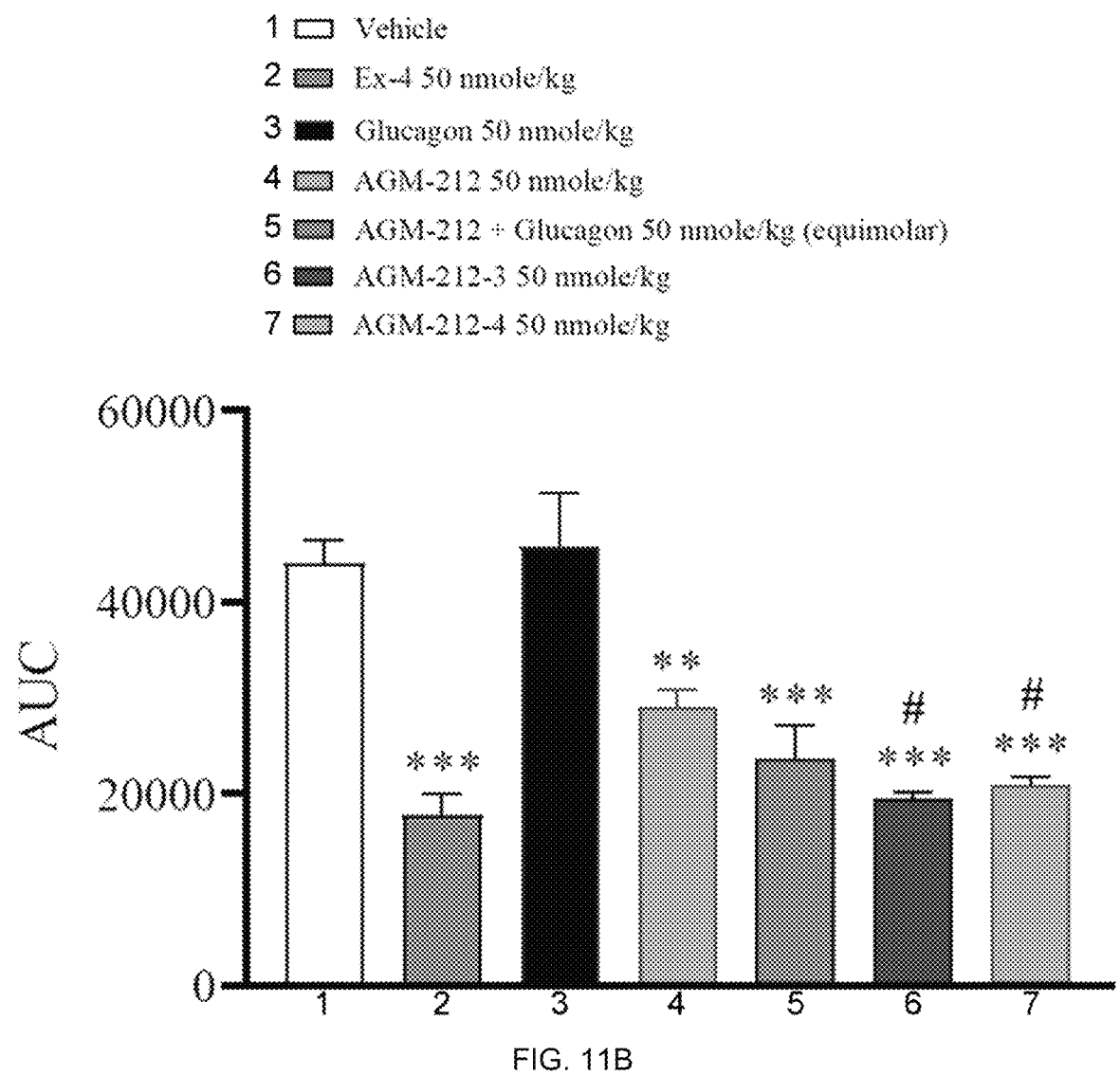
FIG. 11B shows the test results of glucose tolerance improvement of analogs according to an exemplary embodiment of the present disclosure.

Experimental Example 6: Investigation on Glucose Tolerance Improvement Effect of Analogs in Obesity Disease Animal Models During the period corresponding to the 7th week in the experimental procedure of Example 5, the glucose tolerance improvement effect by AGM-212-3 was investigated. Specifically, the same obesity disease mice on the 7th week of the experiment were fasted for 16 hours, and each analog was subcutaneously administered at 10 nmole/kg, and after 30 minutes, glucose (1.5 g/kg) was administered intraperitoneally. The blood glucose was measured for 120 minutes by a blood glucose meter (accu-check, Roche, Germany) for blood extracted from the tail vein of the mice at 0, 15, 30, 45, 60, 90, and 120 minutes. The results are shown in FIGS. 11A and 11B and Table 12.

TABLE 12

| Group | Blood glucose (Area under curve) |
|---|---|
| Vehicle | 43957.5 ± 2483.8 |
| Ex4 | 17795.0 ± 2137.4 |

TABLE 12-continued

| Group | Blood glucose (Area under curve) |
|---|---|
| AGM-212 | 45846.2 ± 5538.1 |
| Glucagon | 29029.5 ± 1784.5 |
| AGM-212 + glucagon | 23687.5 ± 3393.1 |
| AGM-212-3 | 19545 ± 623.1 |
| AGM-212-4 | 20936.2 ± 837.3 |

As can be confirmed in FIGS. 11A and 11B and Table 12, the mouse group administered each analog showed reduced blood glucose and showed a significant blood glucose reduction in each blood glucose measurement time compared with the control group. The above results indicate that the glucose tolerance of the obesity disease mice was improved by long-term administration of the analogs.

Experimental Example 7: Investigation on Insulin Resistance Improvement Effect of Analogs in Obesity Disease Animal Models It has been reported that the increased fat accumulation in the body due to obesity increases the lipotoxicity on the pancreatic islet beta cells that produce insulin, thereby reducing insulin production, and inhibits insulin consumption of blood glucose, increased after a meal, in the liver and muscle as tissues that absorb and store blood glucose, thereby inducing hyperinsulinemia and reduced insulin functions, so that the fat accumulation is a main cause of an insulin resistance increase that mainly causes hyperglycemia symptoms.

During the period corresponding to the 8th week of the long-term administration experiment using the obesity disease mice at the 9th week of Experimental Example 5, the insulin resistance test was conducted to investigate insulin sensitivity due to the long-term administration of a drug. After the end of the long-term experiment, the mouse blood was extracted and analyzed for the blood insulin level through the mouse insulin ELISA to investigate whether insulin resistance was improved.

Figure 12A:
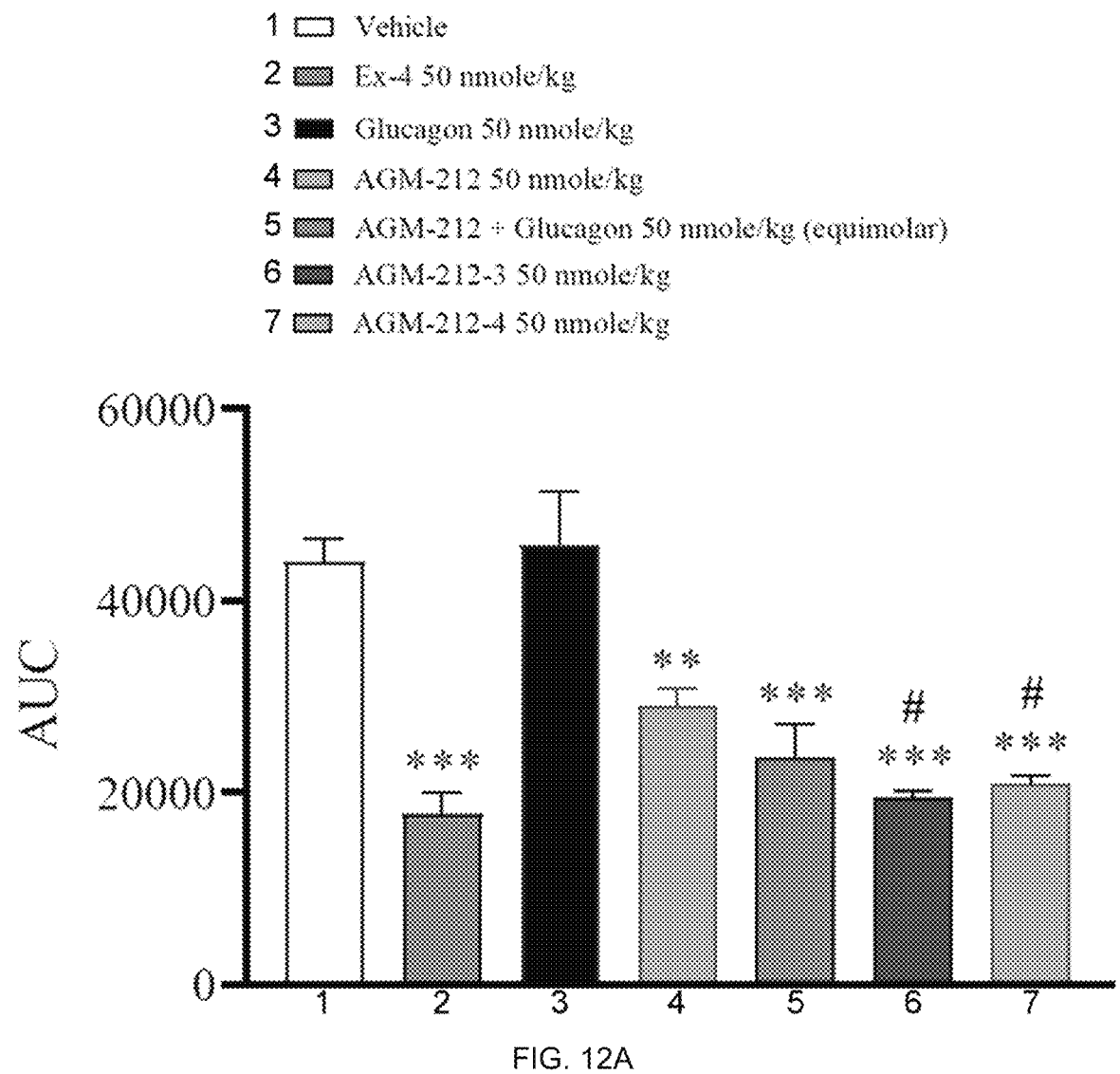
FIG. 12A shows the test results of insulin resistance improvement results of analogs according to an exemplary embodiment of the present disclosure.
Figure 12B:
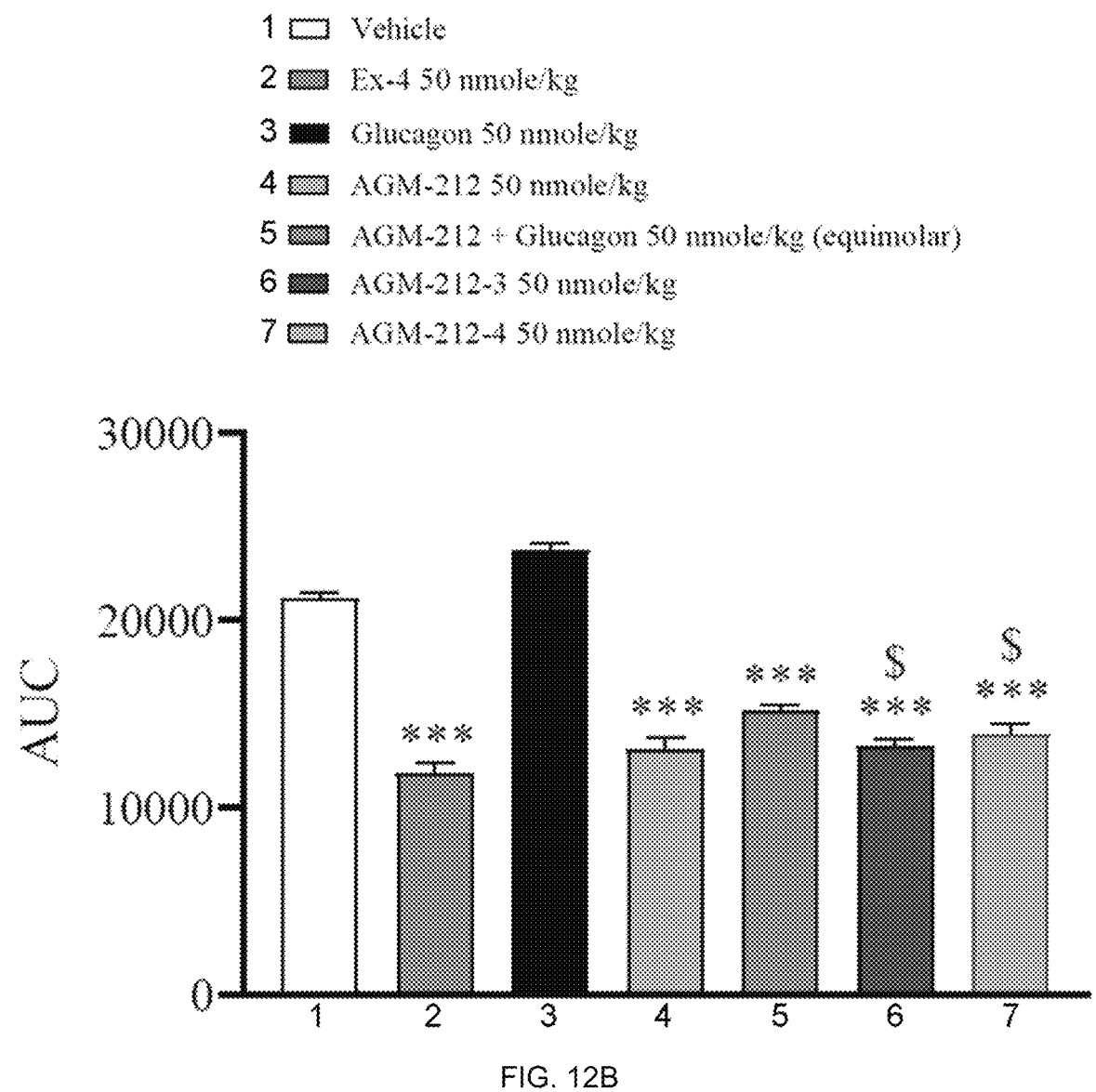
FIG. 12B shows the test results of insulin resistance improvement results of analogs according to an exemplary embodiment of the present disclosure.

Specifically, the obesity disease mice at the 8th week of the long-term administration experiment were fasted for 6 hours, and each analog was subcutaneously administered at 1 nmole/kg, and after 30 minutes, glucose (1 unit/kg) was administered intraperitoneally. The blood was extracted from the tail of the mice at 0, 15, 30, 60, 90, and 120 minutes, and measured for blood glucose through a blood glucose meter (accu-check, Roche, Germany) to analyze insulin sensitivity. The results are shown in FIGS. 12A and 12B and Tables 13 and 14.

TABLE 13

| Group | Blood glucose (Area under curve) |
|---|---|
| Vehicle | 21231.2 ± 293.4 |
| Ex4 | 11847.0 ± 582.7 |
| AGM-212 | 23749.5 ± 387.6 |
| Glucagon | 13102.5 ± 638.8 |
| AGM-212 + glucagon | 15222.0 ± 263.6 |
| AGM-212-3 | 13288.5 ± 409.1 |
| AGM-212-4 | 13966.2 ± 504.1 |

TABLE 14

| Group | Insulin (ng/ml) | Leptin (pg/ml) | Triglyceride (nmol/ul) | Cholesterol (ug/ul) |
|---|---|---|---|---|
| Vehicle | 241.72 ± 56.27 | 669.92 ± 30.47 | 56.25 ± 2.11 | 205.92 ± 7.19 |
| Ex4 | 67.52 ± 12.33 | 341.41 ± 43.10 | 48.64 ± 1.94 | 156.17 ± 8.56 |
| AGM-212 | 44.77 ± 12.21 | 212.52 ± 23.92 | 40.51 ± 1.28 | 134.28 ± 5.06 |
| Glucagon | 86.08 ± 21.43 | 463.09 ± 44.22 | 43.01 ± 1.38 | 161.43 ± 7.55 |
| AGM-212 + glucagon | 44.46 ± 9.17 | 175.21 ± 40.57 | 34.51 ± 0.85 | 111.23 ± 1.62 |
| AGM-212-3 | 26.90 ± 6.86 | 95.81 ± 10.10 | 31.76 ± 1.81 | 92.83 ± 3.00 |

As can be confirmed in FIGS. 12A and 12B and Table 13, in the experimental group administered each analog, the blood glucose showed high sensitivity to the intraperitoneally administered insulin and was promptly reduced.

As can be confirmed in Table 14, the blood insulin level was significantly reduced in the mouse groups administered the analogs after the end of the experiment.

The results indicate that the long-term administration of AGM-212-3 and AGM-212-4 improved insulin sensitivity and hyperinsulinemia, thereby inducing the recovery of insulin functions in obesity disease mice.

Experimental Example 8: Investigation on Amount of Hepatic Fat Accumulation Changed by Analogs in Obesity Disease Animal Models It is known that overweight and obesity due to high-fat diet intake increases fat accumulation in the metabolic tissue liver, lipid synthesis in hepatocytes, and the like, thereby causing an increase in incidence of non-alcoholic fatty liver disease, a metabolic disease. To investigate whether weight loss in obesity disease mice according to the long-term administration of AGM-212-3 influenced the alleviation of symptoms of fatty liver as a related metabolic disease, the amount of lipid in the liver tissue was analyzed through Oil Red 0 staining, which is a staining method for lipid confirmation, and the liver tissue was lysed to determine the amount of triglyceride as a form of intracellular lipid storage.

Specifically, after the end of the 9-week long-term administration experiment in Experimental Example 5, the mouse liver was extracted and divided into respective lobes, some of which were then placed in 4% formaldehyde and fixed, and then a paraffin block was prepared and sliced. Thereafter, the prepared slide was stained with Oil Red O, a staining reagent for lipid confirmation, and then observed through a microscope. For the measurement of the amount of triglyceride in liver tissue, the isolated liver tissue was lysed using a 70-μm cell strainer, centrifuged at 14,000 rpm, and the resulting supernatant containing triglyceride was diluted at a certain ratio and then analyzed using triglyceride ELISA. The results are shown in FIGS. 13A to 13B.

TABLE 15

| Group | Hepatic triglyceride (mg/g) |
|---|---|
| Vehicle | 39.38 ± 4.08 |
| AGM-212 | 7.50 ± 1.01 |
| AGM-212-3 | 3.58 ± 0.12 |

Figure 13A:
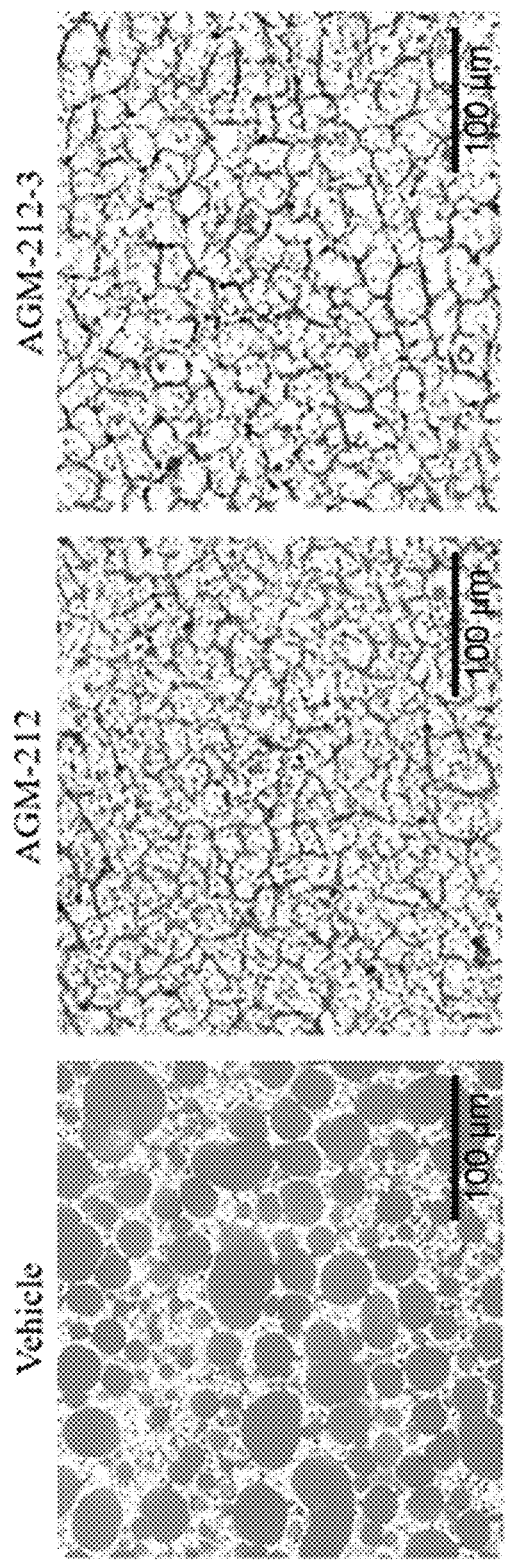
FIG. 13A shows the test results of hepatic fat accumulation amounts by analogs according to an exemplary embodiment of the present disclosure.
Figure 13B:
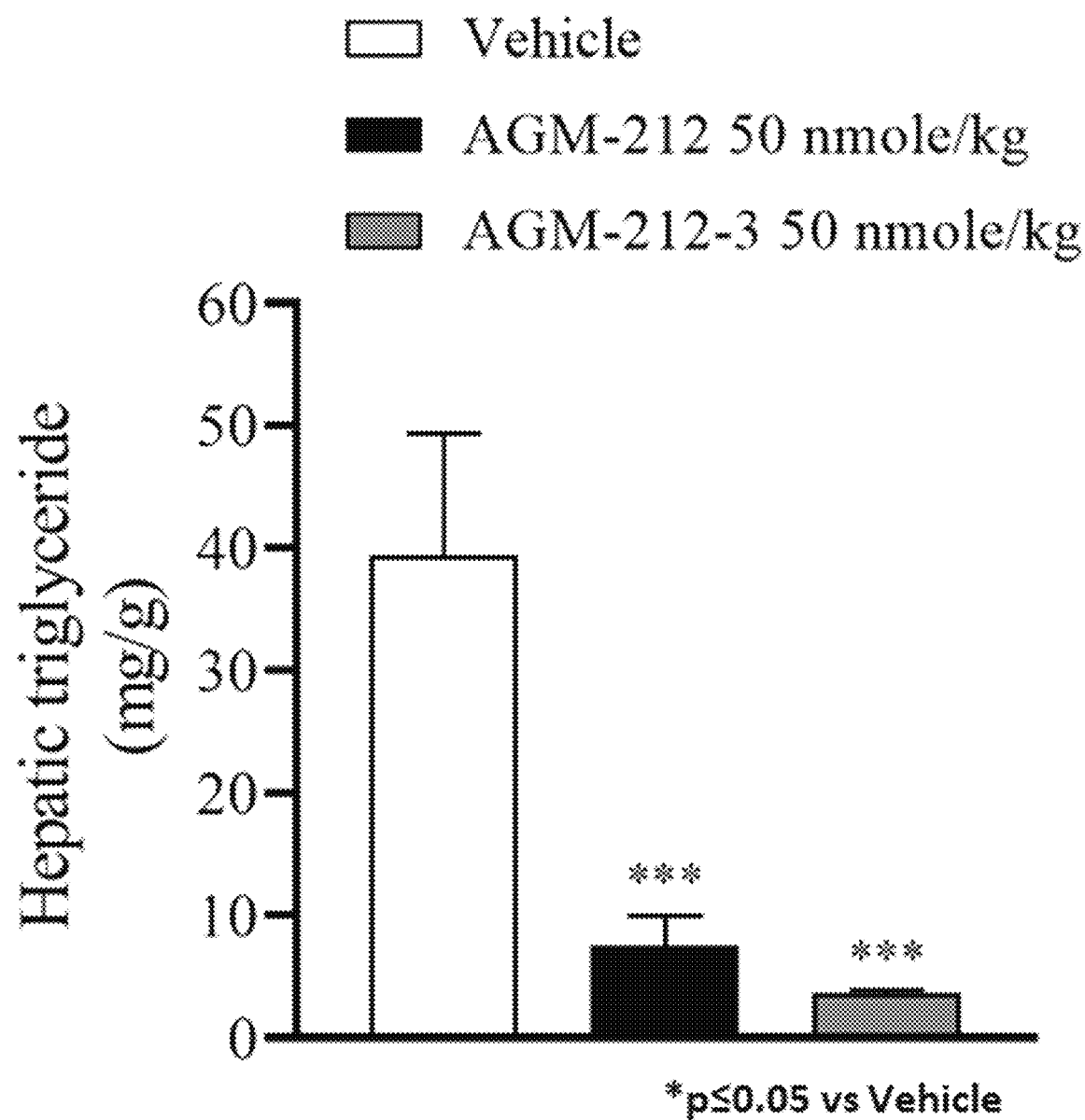
FIG. 13B shows the test results of hepatic fat accumulation amounts by analogs according to an exemplary embodiment of the present disclosure.

As can be confirmed in FIGS. 13A and 13B and Table 15, in the mice administered AGM-212-3, the lipid range stained with Oil Red 0 in the liver was decreased and the amount of triglyceride in liver tissue was also significantly decreased.

The above results indicate that the body weight reduction by the long-term administration of AGM-212-3 has an effect of reducing the risk of fatty liver disease due to high-fat diet intake in obesity disease mice.

Experimental Example 9: Investigation on Changes in Levels of Blood Metabolic Parameters by in Obesity Disease Animal Models The levels of the blood glucose control hormone insulin and the dietary control hormone leptin in the blood are higher than normal levels due to the resistance to each hormone in the tissue when Type 2 diabetes and obesity occur, and these symptoms are called hyperinsulinemia and hyperleptinemia, respectively, which are used as diagnostic markers for metabolic diseases. The increases in the levels of lipids, such as cholesterol and triglyceride, in the blood, that is, hyperlipidemia, is a representative symptom of overweight and obesity. As such, those are representative mark for determining the degree of obesity.

To investigate whether the alleviation of metabolic abnormality symptoms, such as insulin, leptin resistance, and degree of obesity, were induced by long-term administration of AGM-212-3 in Experimental Example 5, the mouse blood was collected after the end of the experiment, and the levels of blood metabolic parameters were analyzed through ELISA examinations corresponding to respective parameters to be examined. The results are shown in Table 14.

As can be confirmed in Table 14, the mouse group administered AGM-212-3 showed significant decreases in the levels of insulin and leptin in the blood, and also showed significant diseases in the levels of lipids, such as cholesterol and triglyceride.

The results indicate that the improvements in hyperlipidemia and metabolic hormone resistances caused by intake of a high-fat diet in the obesity disease mice were induced by the administration of AGM-212-3.

Experimental Example 10: Investigation on Thermogenesis Increasing Effect of Analogs in Obesity Disease Animal Models It has been reported that the increase in thermogenesis induced by the interaction of glucagon and glucagon receptor in brown adipose tissue increases the expression of the protein Uncoupling protein 1 (UCP-1) in mitochondria to prevent the use of hydrogen, generated during oxidation and reduction of Acetyl CoA generated by oxidation of a fatty acid, to oxidative phosphorylation, that is, respiration and to pass UCP1 therethrough, and the energy generated herein is released as heat to increase the consumption of the fat accumulated in the body and thus plays a major role in body weight reduction.

To investigate the thermogenesis increasing effect of AGM-212-3, 16-week-old obesity disease mice (Diet induced obese C57BL/6) were subcutaneously administered once a day for 5 weeks, and then the amount of thermogenesis, amount of motion, respiratory quotient, and rectal temperature were measured.

Specifically, while mice subjected to long-term administration for 5 weeks were bred for 24 hours in a metabolic cage connected to an indirect calorimetry system, which is an energy metabolism analysis device, the amount of oxygen consumed and the amount of carbon dioxide emitted through respiration were measured at 1-hour intervals, thereby analyzing the respiratory quotient, which is an index to identify the amount of thermogenesis and the preference of nutrients consumed in the body. After 24 hours, the mice were taken out of the metabolic cage and a thermal probe was inserted through the anus to measure the rectal temperature. The results are shown in FIGS. 14A to 14B.

TABLE 16

| Group | Energy expenditure (kcal/day/kg$^{0.75}$) | |
|---|---|---|
| | Dark | Light |
| Vehicle | 161.76 ± 3.49 | 145.56 ± 2.58 |
| AGM-212 | 189.30 ± 3.53 | 158.01 ± 3.43 |
| AGM-212-3 | 201.78 ± 3.33 | 175.39 ± 3.20 |

Figure 14A:
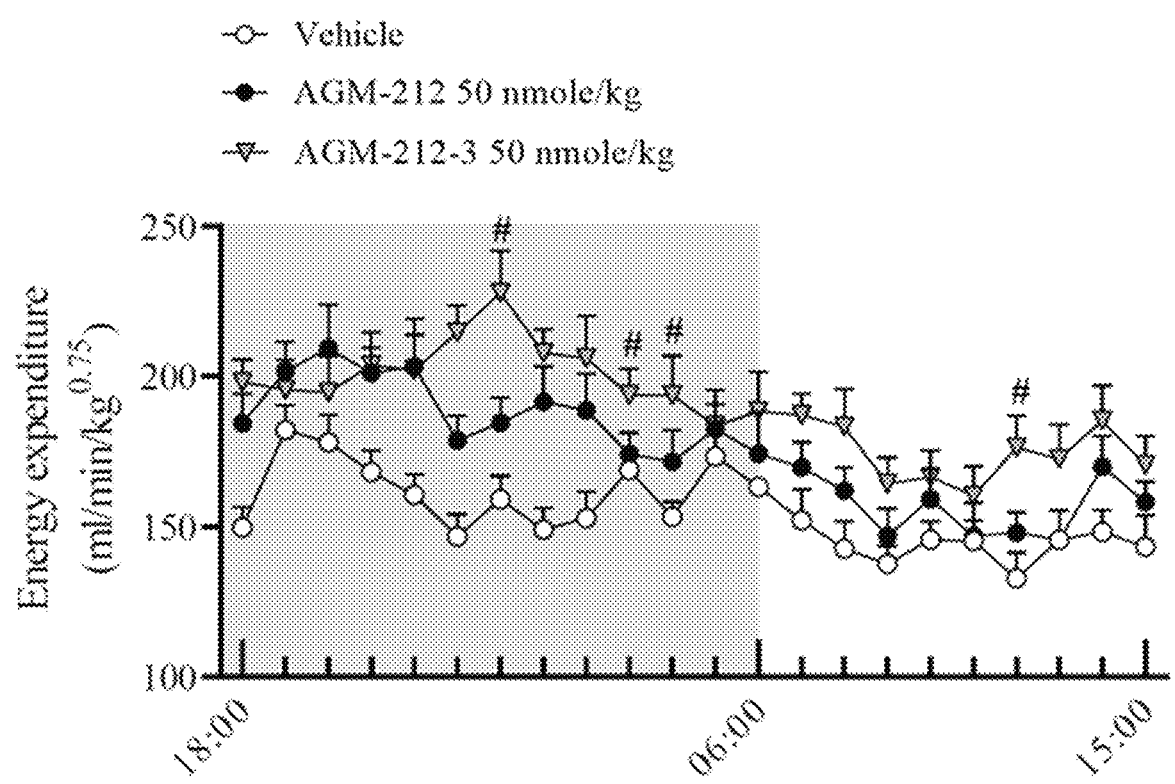
FIG. 14A shows the test results of heat energy increasing effects of analogs according to an exemplary embodiment of the present disclosure.
Figure 14B:
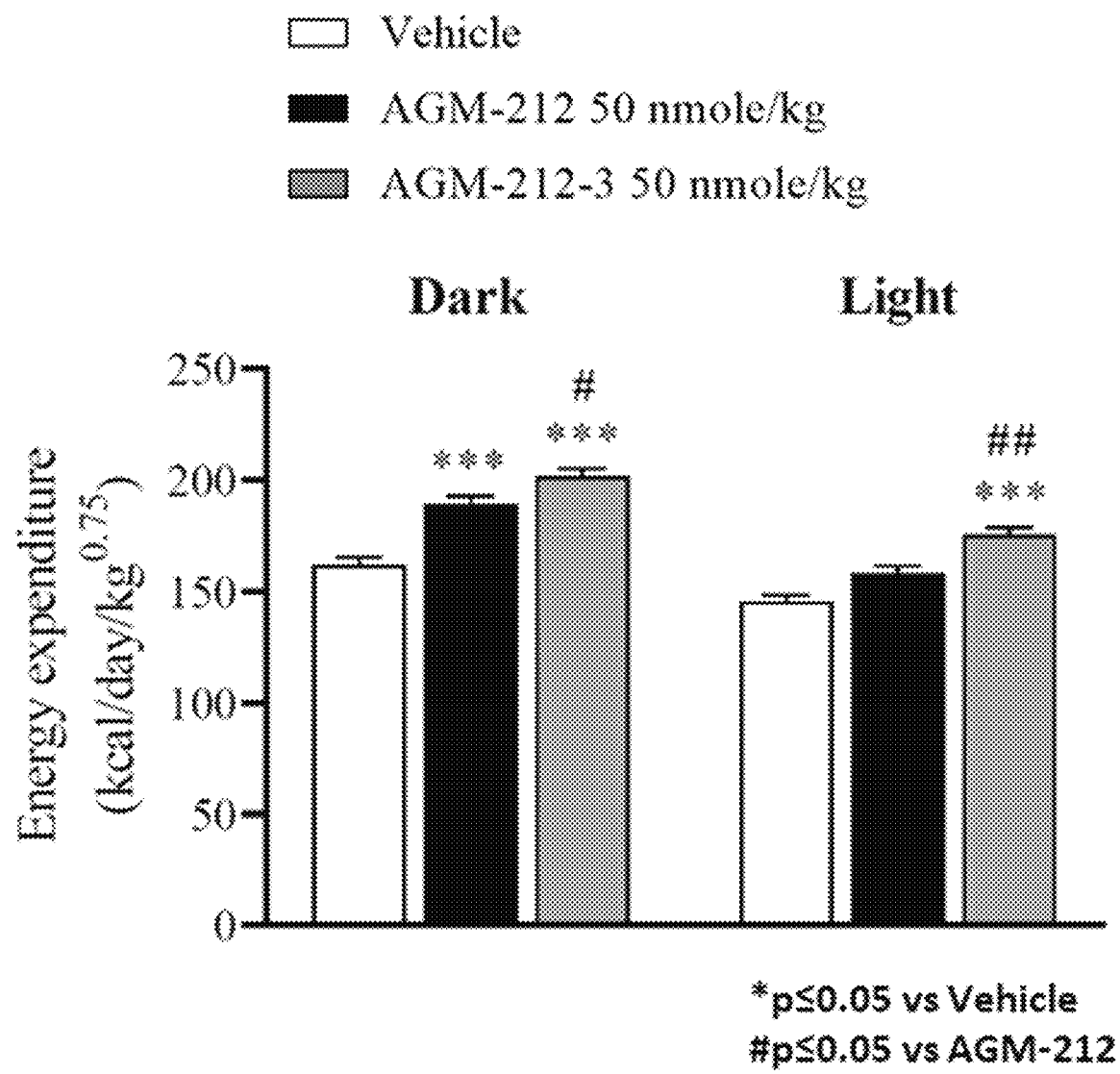
FIG. 14B shows the test results of heat energy increasing effects of analogs according to an exemplary embodiment of the present disclosure.

As can be confirmed in FIGS. 14A and 14B and Table 16, the energy expenditure and the rectal temperature were significantly increased in only the mouse group administered AGM-212-3 in the 12-hr light and 12-hr dark conditions. However, it was identified that compared with the control group, no significant change in total amount of motion was not made whereas the motion pattern was changed. The respiratory quotient was a significant decrease, close to 0.7, in both the light and dark conditions.

The results indicate that regardless of the amount of motion in the obesity disease mice, the thermogenesis that consumes fat was increased through the long-term maintained glucagon activity by the analog, and thus plays a main role in body weight reduction.

Figure 15A:
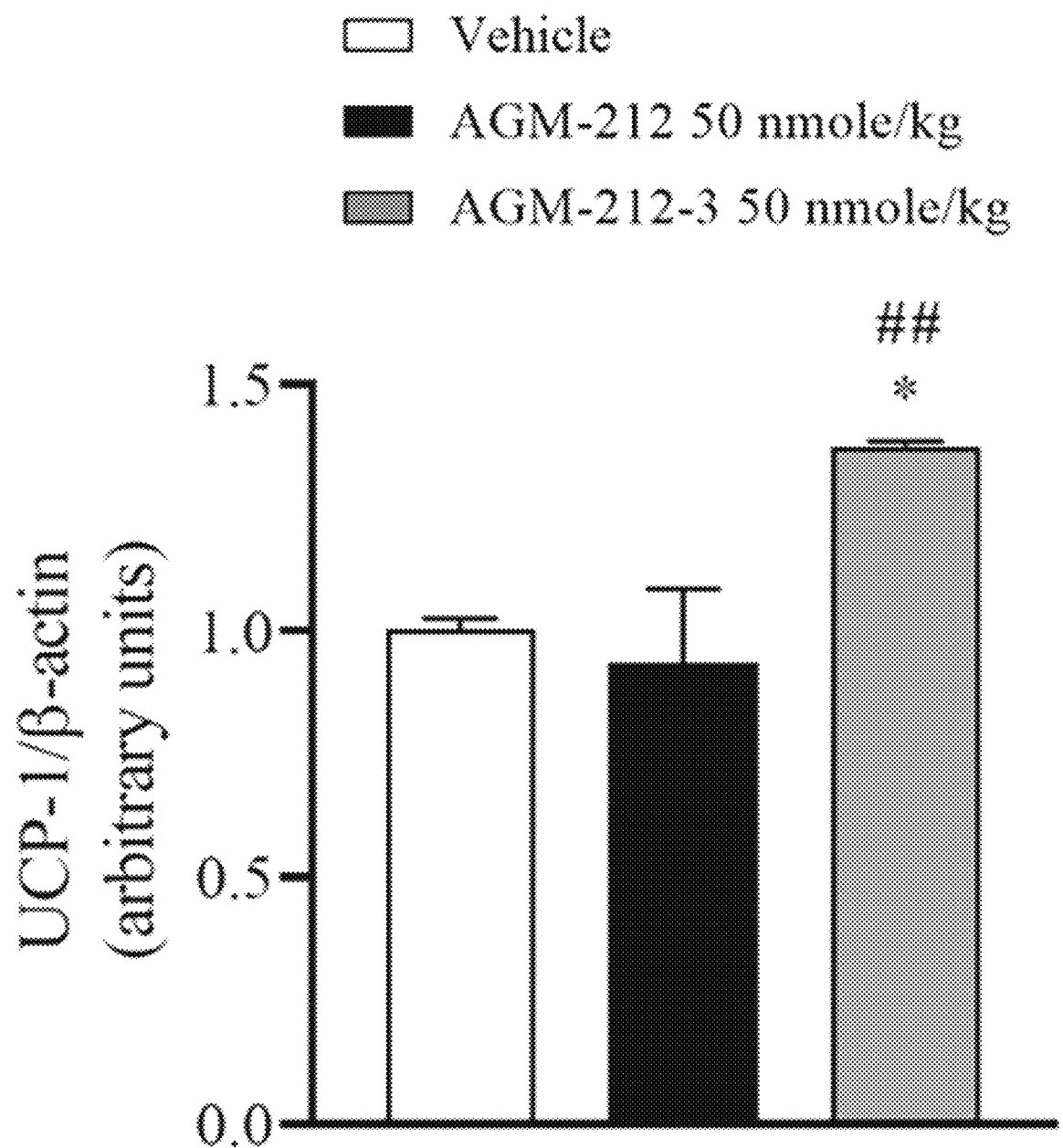
FIG. 15A shows the test results of thermogenesis-related components of analogs according to an exemplary embodiment of the present disclosure.
Figure 15B:
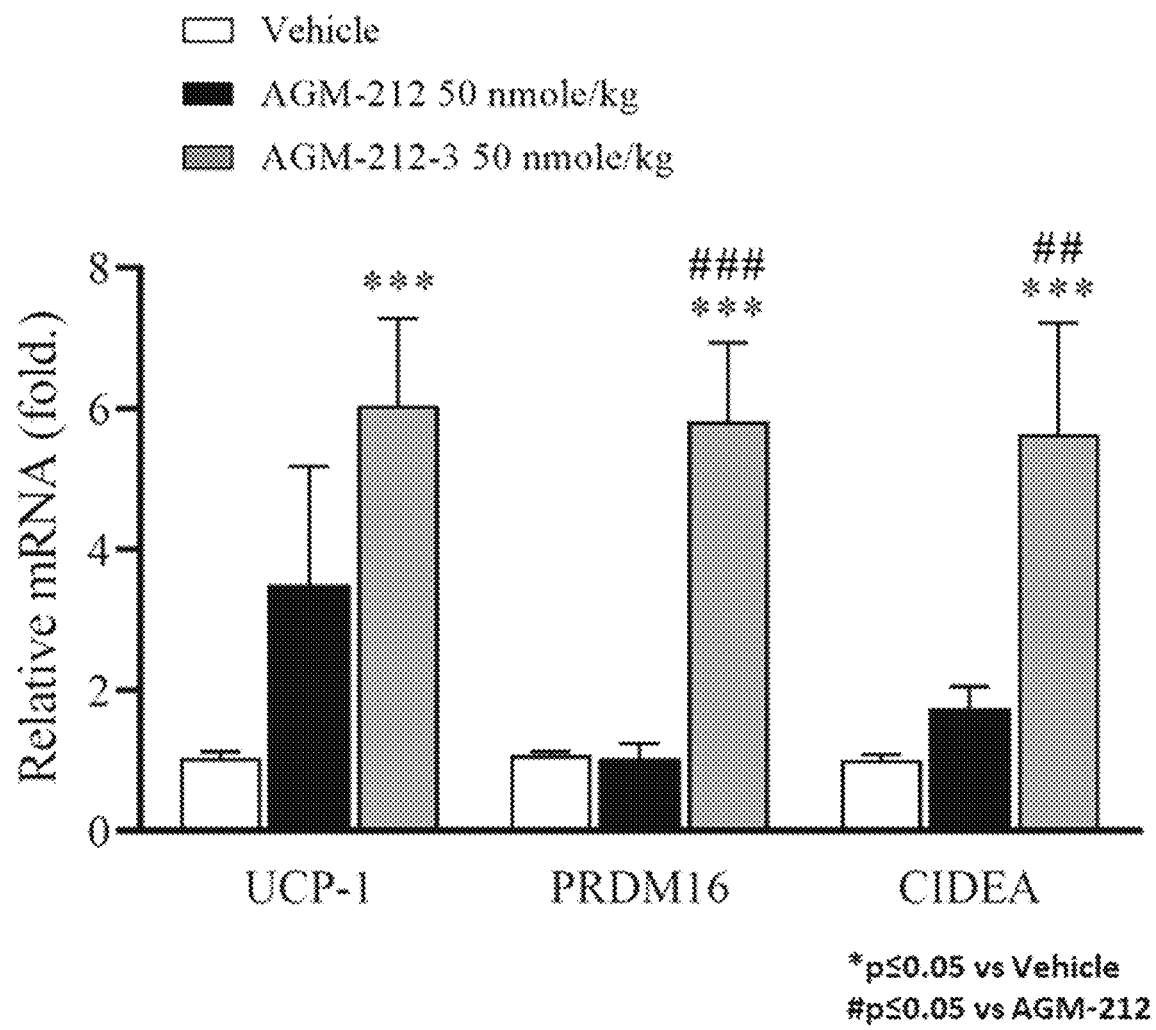
FIG. 15B shows the test results of thermogenesis-related components of analogs according to an exemplary embodiment of the present disclosure.
Figure 16A:
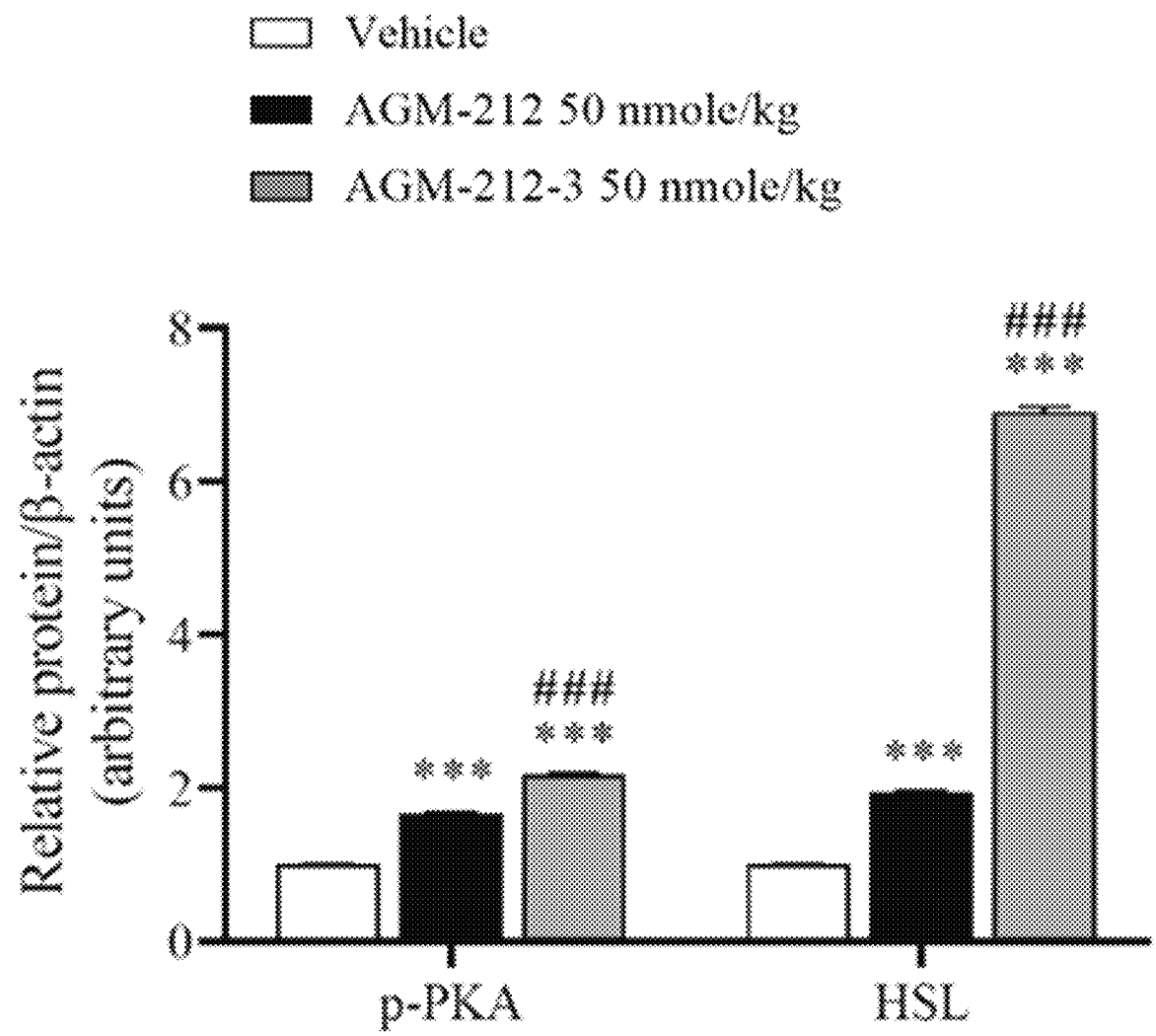
FIG. 16A shows the test results of lipolytic ability of analogs according to an exemplary embodiment of the present disclosure.
Figure 16B:
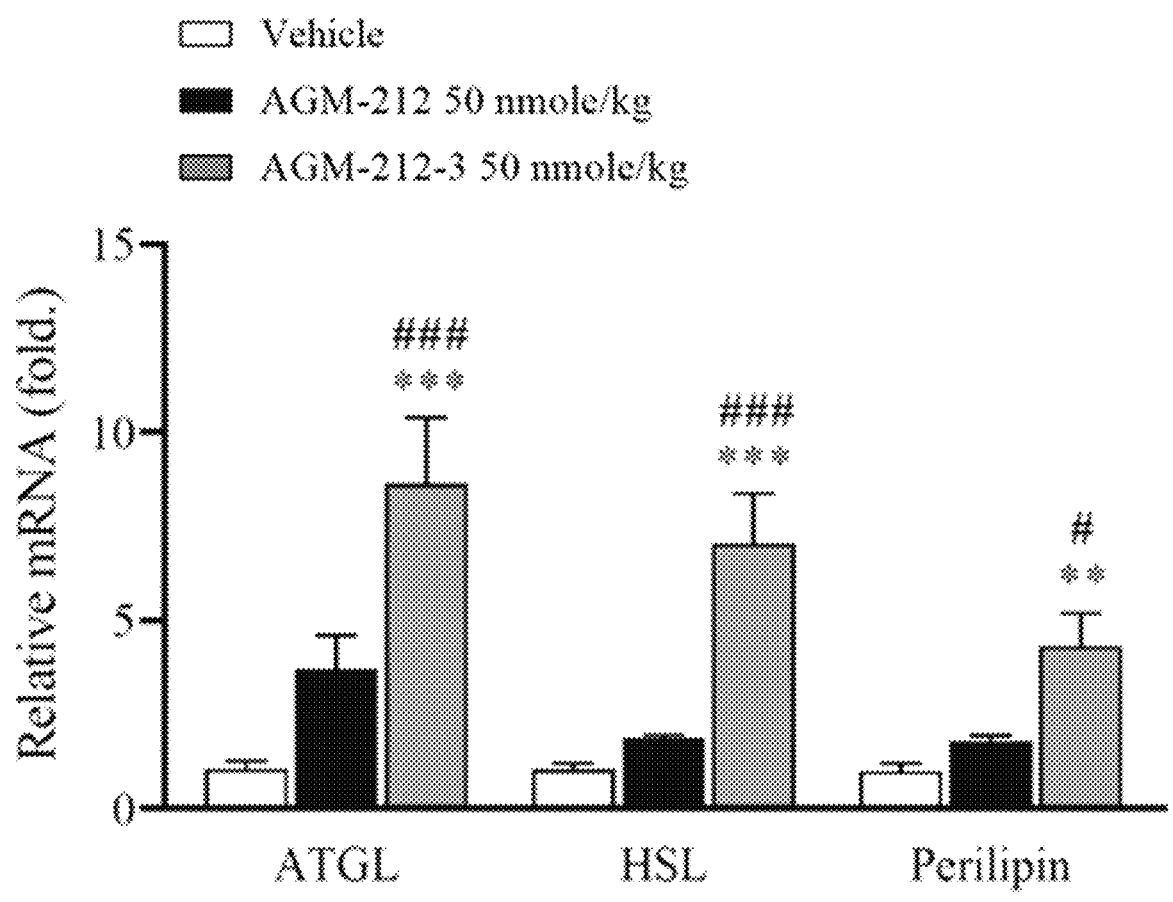
FIG. 16B shows the test results of lipolytic ability of analogs according to an exemplary embodiment of the present disclosure.
Figure 16C:
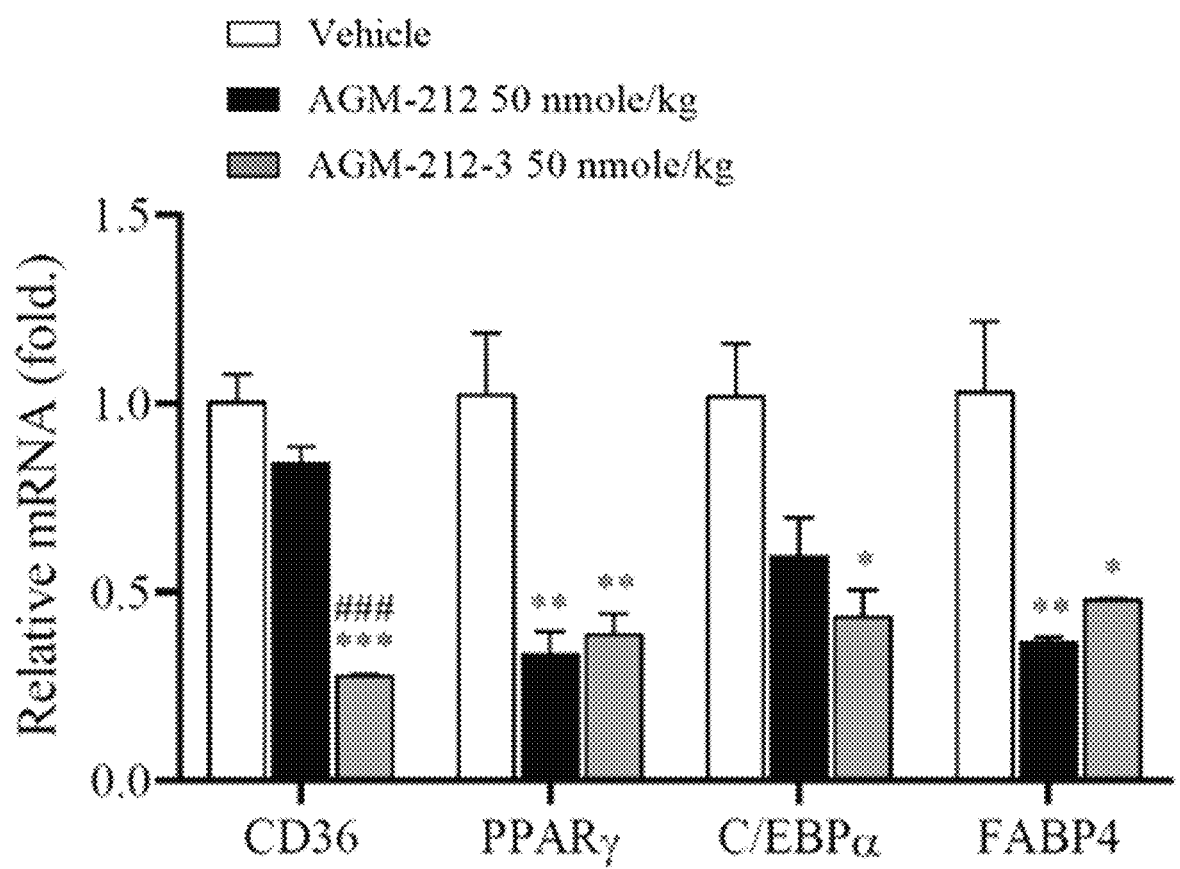
FIG. 16C shows the test results of lipolytic ability of analogs according to an exemplary embodiment of the present disclosure.
Figure 16D:
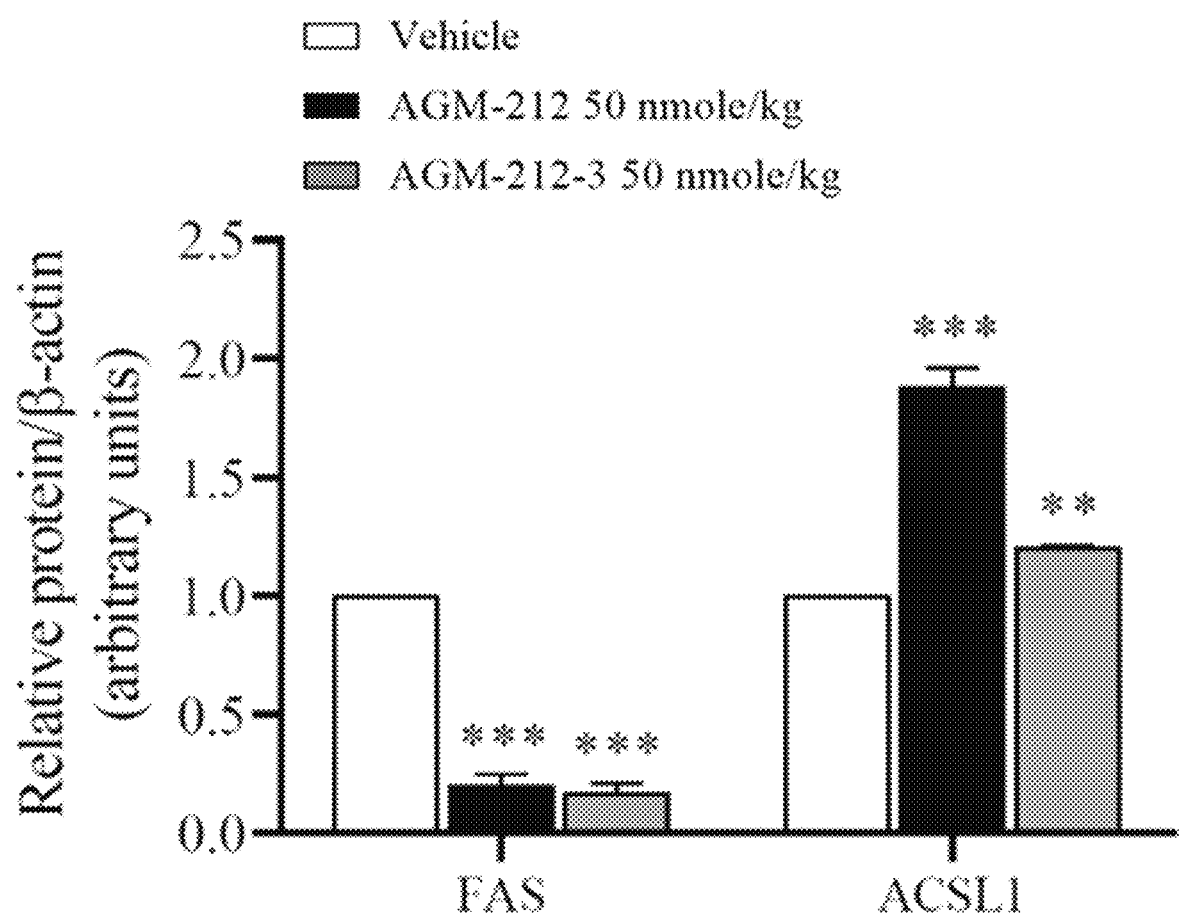
FIG. 16D shows the test results of lipolytic ability of analogs according to an exemplary embodiment of the present disclosure.
Figure 16E:
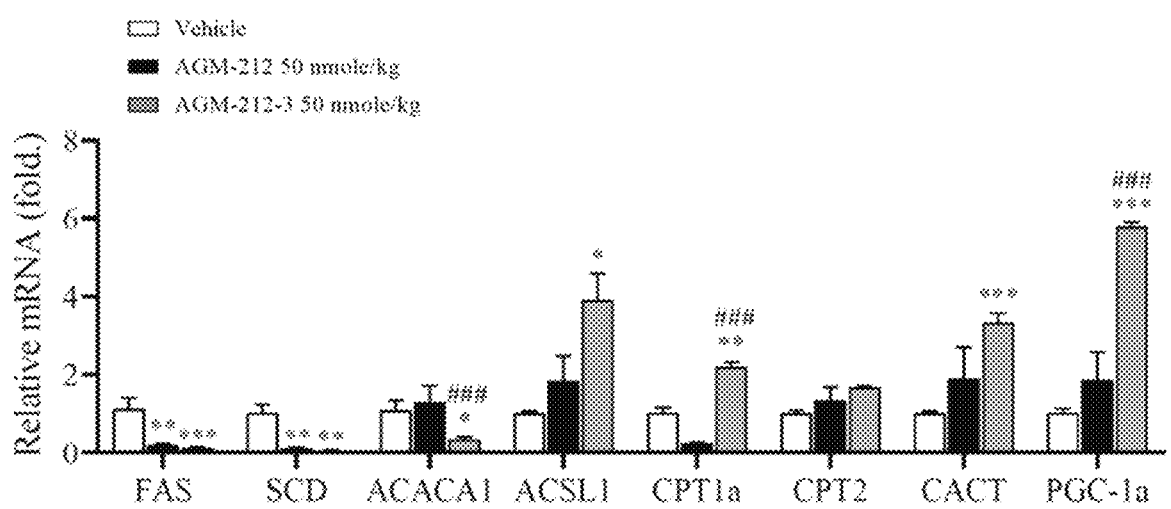
FIG. 16E shows the test results of lipolytic ability of analogs according to an exemplary embodiment of the present disclosure.

Experimental Example 11: Investigation on Changes in Levels of Thermogenesis-Related Components in Obesity Disease Animal Models To verify the thermogenesis increasing mechanism of AGM-212-3 in Experimental Example 10, the mouse brown adipose tissue was isolated after the 5-week long-term administration experiment, and the expression levels of UCP1, PRDM16, and CIDEA, which are major components for the thermogenesis mechanism, were analyzed by Western blotting and quantitative real time polymerase chain reaction (qRT-PCR). In addition, the brown adipose tissue fixed in 4% paraformaldehyde was treated with an antibody having specific affinity for UCP1 to observe the expression level of UCP1 in the brown adipose tissue. The results are shown in FIGS. 15A to 15B.

TABLE 17

| Group | UCP-1/β-actin expression ratio (arbitrary units) |
|---|---|
| Vehicle | 1.00 ± 0.02 |
| AGM-212 | 0.93 ± 0.15 |
| AGM-212-3 | 1.37 ± 0.01 |

TABLE 18

| | mRNA expression (fold.) | | |
|---|---|---|---|
| Group | UCP-1 | PRDM16 | CIDEA |
| Vehicle | 1.02 ± 0.10 | 1.06 ± 0.05 | 1.00 ± 0.08 |
| AGM-212 | 3.47 ± 1.69 | 1.01 ± 0.23 | 1.73 ± 0.31 |
| AGM-212-3 | 6.03 ± 1.24 | 5.81 ± 1.12 | 5.63 ± 1.58 |

As can be confirmed in FIGS. 15A and 15B and Tables 17 and 18, the expression level of UCP1 protein in the brown adipose tissue and the mRNA expression levels of UCP-1, PRDM16, and CIDEA were all significantly increased in the group administered with the analog compared with control group. It was also confirmed in the immunohistochemistry (IHC) images that the amount of UCP1 in the brown adipose tissue was increased compared with that of the control group.

The results indicate that AGM-212-3 activated the glucagon receptor in the brown adipose tissue to increase the generation of signaling pathways regulating the expression thermogenesis-related components.

Experimental Example 12: Investigation on Lipolytic Ability of Analog

To investigate the reduction in adipose tissue and the changes in expression levels of major components for the lipid synthesis/lysis mechanisms in the tissue according to the long-term administration of AGM-212-3, the testicular and groin white adipose tissue after the end of the long-term administration experiment of Example 11, and subcutaneous brown adipose tissue were isolated, followed by size measurement for each tissue, and then the changes in expression levels of the respective metabolic components were analyzed through Western blotting and qRT-PCR. The results are shown in FIGS. 16A to 16E.

As can be confirmed in FIGS. 16A to 16E, it was confirmed through the Western blotting that the protein expression of protein kinase A, an important component for lipolysis signaling, and HSL, a lipolytic enzyme, were significantly increased in the testicular white adipose tissue of mice in the experimental group.

It was also confirmed through qRT-PCR that the mRNA expression levels of ATGL and HSL, lipolytic enzymes, and Perilipin, a major component for lipolysis, were significantly increased, and the mRNA expression levels of CD36, PPARr, C/EBPa, and FABP4, involved in lipid synthesis and intracellular fatty acid uptake, were significantly reduced.

It was also confirmed through Western blotting and qRT-PCR that the protein expression levels of FAS and the mRNA expression levels of SCD and ACACA1, which are major components for lipid synthesis signaling, but the protein expression level of ACSL1 and the protein and mRNA expression levels of CPT1a, CPT2, CACT, and PGC-1a, which are major components for fatty acid beta-oxidation signaling, were significantly increased in the groin white adipose tissue of the experimental group mice.

Experimental Example 13: Investigation on Intramyocellular Lipolytic Ability and Thermogenesis Effect of Analogs Skeletal muscles are a main organ responsible for the basal metabolic rate, and skeletal muscles have been reported to play an important role in body weight control by increasing thermogenesis through the same mechanism as brown adipocytes.

Hence, to verify whether AGM-212-3 can increase thermogenesis in the muscle, the changes in expression levels of metabolic components related to lipid synthesis and lysis and fatty acid transport signaling in the myoblast cell line C2C12 were analyzed through Western blotting and qRT-PCR. The results are shown in FIGS. 17A to 17C.

Figure 17A:
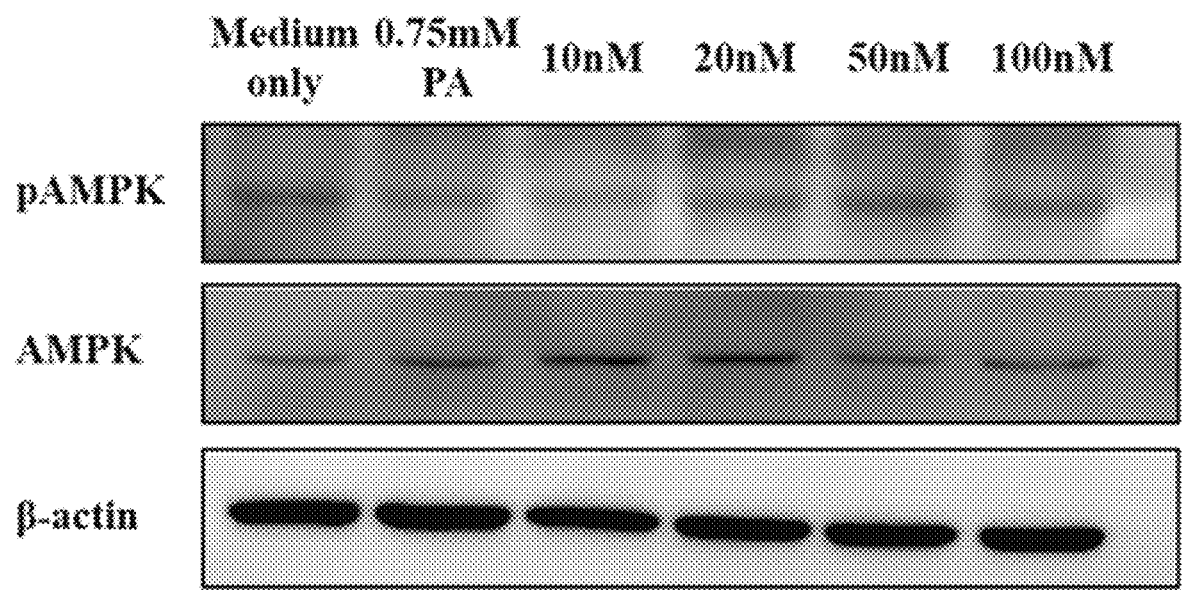
FIG. 17A shows the test results of intramyocellular lipolytic ability and thermogenesis effect of analogs according to an exemplary embodiment of the present disclosure.
Figure 17B:
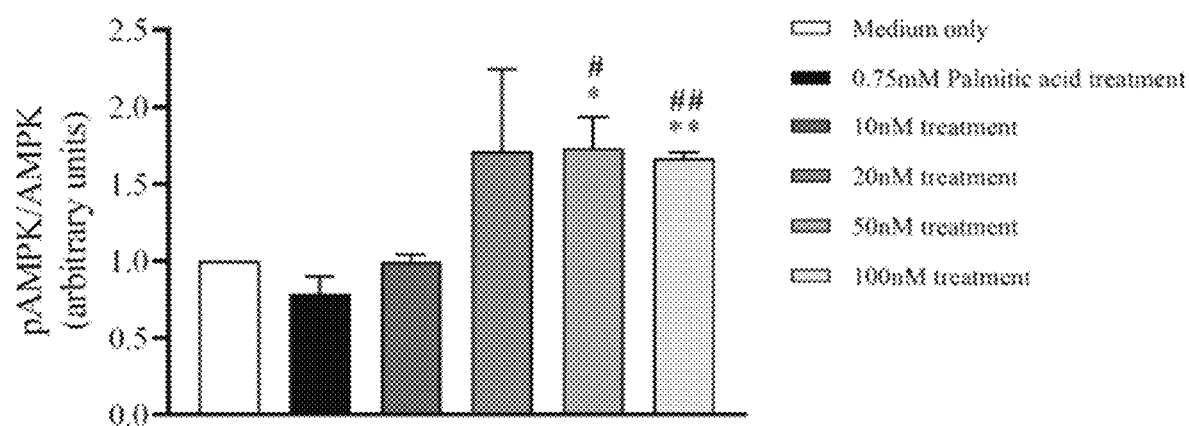
FIG. 17B shows the test results of intramyocellular lipolytic ability and thermogenesis effect of analogs according to an exemplary embodiment of the present disclosure.
Figure 17C:
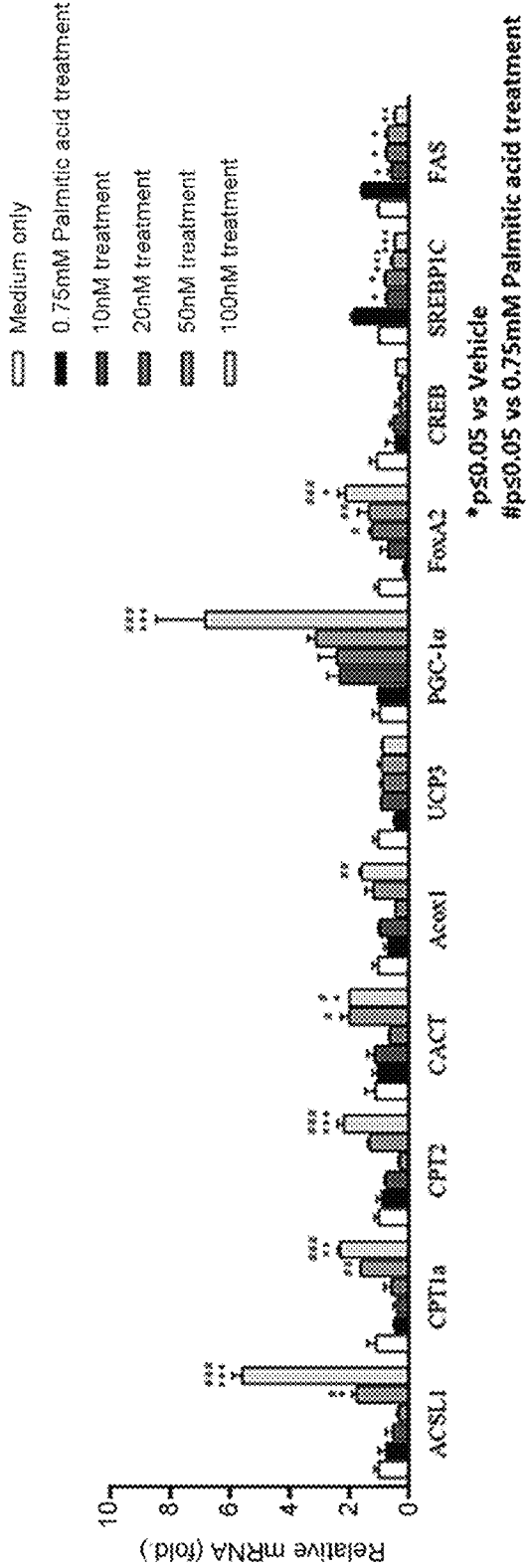
FIG. 17C shows the test results of intramyocellular lipolytic ability and thermogenesis effect of analogs according to an exemplary embodiment of the present disclosure.

As can be confirmed in FIGS. 17A to 17C, it was confirmed through Western blotting that the phosphorylation of AMPK, a major signaling transmitter for thermogenesis signaling pathways in C2C12 cells, tended to decrease in the fatty acid palmitic acid (0.75 mM) treatment compared with the control group, but the phosphorylation of AMPK was significantly increased in a dose-dependent manner in the treatment with the analog at different concentrations (10 nM, 20 nM, 50 nM, 100 nM).

It was also confirmed through qRT-PCR that the mRNA expression levels of the components (ACSL1, CPT1a, CPT2, and CACT), involved in the fatty acid metabolism and fatty acid transport, and the fatty acid beta oxidation signaling components (Acox1, PGC-1a, and FoxA2) in the mitochondria matrix in C1C12 cells were significantly increased in a dose-dependent manner of the conjugate, but the mRNA expression levels of lipid synthesis signaling components (FAS and SREBP-1c) were reduced in a dose-dependent manner of the conjugate.

The above results indicate that GM-212-3 can increase thermogenesis and inhibit lipid synthesis in the skeletal muscle like brown fat and has effective weight reduction ability.

INDUSTRIAL APPLICABILITY

The present disclosure relates to glycosylated exenatide analogs and uses thereof and exenatide dimer analogs and uses thereof.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52 (e).

What is claimed is:

1. An exenatide dimer analog, comprising:
a first body composed of an exenatide analog comprising:
  a deletion of 7 amino acids from the C-terminus in the amino acid sequence of exenatide,
  a substitution of Glu17 with Cys,
  a substitution of Glu24 with Cys and a conjugation of a bromoacetyl glycan to the substituted Cys24,
  a substitution of Asn28 with Cys, and a conjugation of a capric acid at the C-terminus via a Lys linker; and
a second body composed of an exenatide analog comprising a deletion of 7 amino acids from the C-terminus in the amino acid sequence of exenatide,
  a substitution of Glu17 with Cys,
  a substitution of Glu24 with Cys and a conjugation of a bromoacetyl glycan to the substituted Cys24,
  a substitution of Asn28 with Cys, and a conjugation of a capric acid at the C-terminus via a Lys linker;
wherein the first body and the second body are linked via a disulfide bond between the Cys17 residues of each body.

2. A composition for alleviation or treatment of type 2 diabetes, the pharmaceutical composition containing the exenatide dimer analog of claim 1.

3. A method for alleviation or treatment of type 2 diabetes or obesity, or suppression of appetite, comprising: administering to a subject in need thereof a therapeutically effective amount of the exenatide dimer analog of claim 1.

\* \* \* \* \*

```
SEQUENCE LISTING

<160> NUMBER OF SEQ ID NOS: 2

<210> SEQ ID NO 1
<211> LENGTH: 39
<212> TYPE: PRT
<213> ORGANISM: Artificial Sequence
<220> FEATURE:
<223> OTHER INFORMATION: Ex4

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 29
<212> TYPE: PRT
<213> ORGANISM: Artificial Sequence
<220> FEATURE:
<223> OTHER INFORMATION: Glucagon

<400> SEQUENCE: 2

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```